US011253852B2

(12) United States Patent
Low et al.

(10) Patent No.: US 11,253,852 B2
(45) Date of Patent: Feb. 22, 2022

(54) DEVICES, SYSTEMS, AND METHODS FOR PERFORMING OPTICAL ASSAYS

(71) Applicant: Abbott Point of Care Inc., Princeton, NJ (US)

(72) Inventors: Michael Louie Low, Kendall Park, NJ (US); Barry Bass, Bridgewater, NJ (US); Sergey Gershtein, Skillman, NJ (US)

(73) Assignee: Abbott Point of Care Inc., Princeton, NJ (US)

( * ) Notice: Subject to any disclaimer, the term of this patent is extended or adjusted under 35 U.S.C. 154(b) by 544 days.

(21) Appl. No.: 16/104,232

(22) Filed: Aug. 17, 2018

(65) Prior Publication Data
US 2019/0056329 A1 Feb. 21, 2019

Related U.S. Application Data

(60) Provisional application No. 62/546,713, filed on Aug. 17, 2017.

(51) Int. Cl.
*B01L 3/00* (2006.01)
*G01N 21/31* (2006.01)
(Continued)

(52) U.S. Cl.
CPC ... *B01L 3/502715* (2013.01); *B01L 3/502753* (2013.01); *B01L 3/545* (2013.01);
(Continued)

(58) Field of Classification Search
CPC ........ B01L 2200/0605; B01L 2200/10; B01L 2200/143; B01L 2300/021;
(Continued)

(56) References Cited

U.S. PATENT DOCUMENTS 4,954,087 A 9/1990 Lauks et al.
5,096,669 A 3/1992 Lauks et al.
(Continued)

FOREIGN PATENT DOCUMENTS

WO 2010148252 12/2010
WO 2014121388 8/2014
(Continued)

OTHER PUBLICATIONS

Kim et al., "Development of Optical Sensing System for Detection of Fe ions Using Conductive Polymer Actuator Based Microfluidic Pump", IEEE Sensors, Oct. 26, 2008, pp. 1155-1158.
(Continued)

*Primary Examiner* — Melanie Brown
(74) *Attorney, Agent, or Firm* — Kilpatrick Townsend & Stockton LLP

(57) ABSTRACT

This present invention relates generally to devices, systems, and methods for performing optical and electrochemical assays and, more particularly, to devices and systems having universal channel circuitry configured to perform optical and electrochemical assays, and methods of performing the optical and electrochemical assays using the universal channel circuitry. The universal channel circuitry is circuitry that has electronic switching capabilities such that any contact pin, and thus any sensor contact pad in a testing device, can be connected to one or more channels capable of taking on one or more measurement modes or configurations (e.g., an amperometric measurement mode or a current drive mode).

40 Claims, 27 Drawing Sheets

(51) Int. Cl.
| | |
|---|---|
| *G01N 33/49* | (2006.01) |
| *G01N 33/487* | (2006.01) |
| *G01N 27/327* | (2006.01) |
| *G01N 33/53* | (2006.01) |
| *G01N 21/78* | (2006.01) |
| *G01N 27/416* | (2006.01) |
| *G01N 33/50* | (2006.01) |

(52) U.S. Cl.
CPC ......... *G01N 21/3151* (2013.01); *G01N 21/78* (2013.01); *G01N 27/3273* (2013.01); *G01N 27/416* (2013.01); *G01N 33/48785* (2013.01); *G01N 33/492* (2013.01); *G01N 33/50* (2013.01); *G01N 33/5302* (2013.01); *B01L 2200/0605* (2013.01); *B01L 2200/10* (2013.01); *B01L 2200/143* (2013.01); *B01L 2300/021* (2013.01); *B01L 2300/0645* (2013.01); *B01L 2300/087* (2013.01); *B01L 2300/0816* (2013.01); *B01L 2400/0481* (2013.01); *B01L 2400/0487* (2013.01); *B01L 2400/0683* (2013.01); *B01L 2400/0688* (2013.01)

(58) Field of Classification Search
CPC ....... B01L 2300/0816; B01L 2300/087; B01L 2400/0481; B01L 2400/0487; B01L 2400/0683; B01L 2400/0688; B01L 3/502715; B01L 3/502753; B01L 3/545; B01L 2300/0645; G01N 21/3151; G01N 21/78; G01N 27/416; G01N 33/48785; G01N 33/492; G01N 33/50; G01N 33/5302; G01N 27/3273
USPC ..................................................... 435/287.2
See application file for complete search history.

(56) References Cited

U.S. PATENT DOCUMENTS

| | | | |
|---|---|---|---|
| 5,200,051 A | 4/1993 | Cozzette et al. | |
| 5,321,975 A | 6/1994 | Levine et al. | |
| 5,821,399 A | 10/1998 | Zelin | |
| 6,002,474 A * | 12/1999 | Thomas | B04B 5/0407 356/244 |
| 6,235,536 B1 | 5/2001 | Wardlaw | |
| 6,350,613 B1 | 2/2002 | Wardlaw et al. | |
| 7,682,833 B2 | 3/2010 | Miller et al. | |
| 7,850,916 B2 | 12/2010 | Wardlaw | |
| 8,216,529 B2 | 7/2012 | Ade et al. | |
| 8,797,527 B2 | 8/2014 | Hukari et al. | |
| 9,041,790 B2 | 5/2015 | Fine et al. | |
| 9,194,859 B2 | 11/2015 | Emeric et al. | |
| 9,559,240 B1 | 1/2017 | Astier et al. | |
| 11,060,994 B2 | 7/2021 | Low et al. | |
| 11,067,526 B2 | 7/2021 | Low et al. | |
| 2002/0004878 A1* | 1/2002 | Norman | G06F 3/0679 711/103 |
| 2002/0141155 A1* | 10/2002 | Pinneo | C23C 16/272 361/688 |
| 2005/0023152 A1 | 2/2005 | Surridge et al. | |
| 2005/0121325 A1 | 6/2005 | Updyke et al. | |
| 2008/0006535 A1* | 1/2008 | Paik | B01L 3/502792 204/600 |
| 2008/0281471 A1 | 11/2008 | Smith et al. | |
| 2009/0021728 A1* | 1/2009 | Heinz | G01N 1/44 356/244 |
| 2009/0239257 A1 | 9/2009 | Levine et al. | |
| 2010/0276303 A1 | 11/2010 | Fujiwara et al. | |
| 2011/0251075 A1 | 10/2011 | Mcdevitt et al. | |
| 2012/0034647 A1 | 2/2012 | Herzog et al. | |
| 2012/0282602 A1* | 11/2012 | Drader | G01N 27/3273 435/6.1 |
| 2013/0161190 A1 | 6/2013 | Ewart et al. | |
| 2013/0169948 A1 | 7/2013 | Xie et al. | |
| 2014/0017709 A1* | 1/2014 | Lowe | G01N 33/54366 435/7.92 |
| 2014/0318987 A1 | 10/2014 | Guthrie et al. | |
| 2015/0041316 A1 | 2/2015 | Miki et al. | |
| 2015/0204785 A1 | 7/2015 | Kim et al. | |
| 2015/0260713 A1* | 9/2015 | Ghaffari | B01L 3/502715 435/5 |
| 2016/0041104 A1 | 2/2016 | Emeric et al. | |
| 2016/0091455 A1* | 3/2016 | Taylor | B01L 3/5027 435/287.1 |
| 2016/0091510 A1* | 3/2016 | Di Tullio | B01L 3/502715 435/13 |
| 2016/0091512 A1 | 3/2016 | Collier et al. | |
| 2016/0356999 A1 | 12/2016 | Fine | |
| 2017/0059563 A1 | 3/2017 | Smith et al. | |
| 2018/0280973 A1* | 10/2018 | Haeberle | C25D 21/12 |
| 2018/0290139 A1* | 10/2018 | Kurkowski | B01L 3/502761 |

FOREIGN PATENT DOCUMENTS

| | | |
|---|---|---|
| WO | 2015089632 | 6/2015 |
| WO | 2016049545 | 3/2016 |
| WO | 2016049552 | 3/2016 |
| WO | 2016049557 | 3/2016 |
| WO | 2016105548 | 6/2016 |

OTHER PUBLICATIONS

Li et al., "On-Chip Integrated Lensless Microscopy Module for Optical Monitoring of Adherent Growing Mammalian Cells", 32nd Annual International Conference of the IEEE EMBS, Aug. 31, 2010, pp. 1012-1015.
"International Search Report and Written Opinion" issued in PCT/IB2018/056227, dated Nov. 20, 2018, 16 pages.
"International Search Report and Written Opinion" issued in PCT/IB2018/056229, dated Nov. 22, 2018, 14 pages.
"International Search Report and Written Opinion" issued in PCT/IB2018/056232, dated Nov. 20, 2018, 15 pages.
"International Search Report and Written Opinion" issued in PCT/IB2018/056234, dated Dec. 3, 2018, 18 pages.
"International Search Report and Written Opinion" issued in PCT/IB2018/056235, dated Nov. 21, 2018, 15 pages.
"International Search Report and Written Opinion" issued in PCT/IB2018/056236, dated Dec. 5, 2018, 18 pages.
"International Search Report and Written Opinion" issued in PCT/IB2018/056237, dated Dec. 3, 2018, 14 pages.
International Application No. PCT/IB2018/056227, "International Preliminary Report on Patentability", dated Feb. 27, 2020, 11 pages.
International Application No. PCT/IB2018/056229, "International Preliminary Report on Patentability", dated Feb. 27, 2020, 10 pages.
International Application No. PCT/IB2018/056232, "International Preliminary Report on Patentability", dated Feb. 27, 2020, 10 pages.
International Application No. PCT/IB2018/056234, "International Preliminary Report on Patentability", dated Feb. 27, 2020, 13 pages.
International Application No. PCT/IB2018/056235, "International Preliminary Report on Patentability", dated Feb. 27, 2020, 10 pages.
International Application No. PCT/IB2018/056236, "International Preliminary Report on Patentability", dated Feb. 27, 2020, 13 pages.
International Application No. PCT/IB2018/056237, "International Preliminary Report on Patentability", dated Feb. 27, 2020, 10 pages.
U.S. Appl. No. 16/104,204, Non-Final Office Action, dated Oct. 20, 2020, 28 pages.
U.S. Appl. No. 16/104,213, Non-Final Office Action, dated Oct. 21, 2020, 38 pages.
European Application No. EP18770083.6, Office Action, dated Jul. 2, 2021, 6 pages.
European Application No. EP18770084.4, Office Action, dated Jul. 9, 2021, 6 pages.
European Application No. EP18780220.2, Office Action, dated Jul. 9, 2021, 5 pages.

(56) References Cited

OTHER PUBLICATIONS

U.S. Appl. No. 16/104,204, Notice of Allowance, dated Mar. 8, 2021, 13 pages.
U.S. Appl. No. 16/104,213, Notice of Allowance, dated Mar. 4, 2021, 11 pages.
European Application No. EP18770085.1, Office Action, dated Dec. 9, 2021, 6 pages.

* cited by examiner

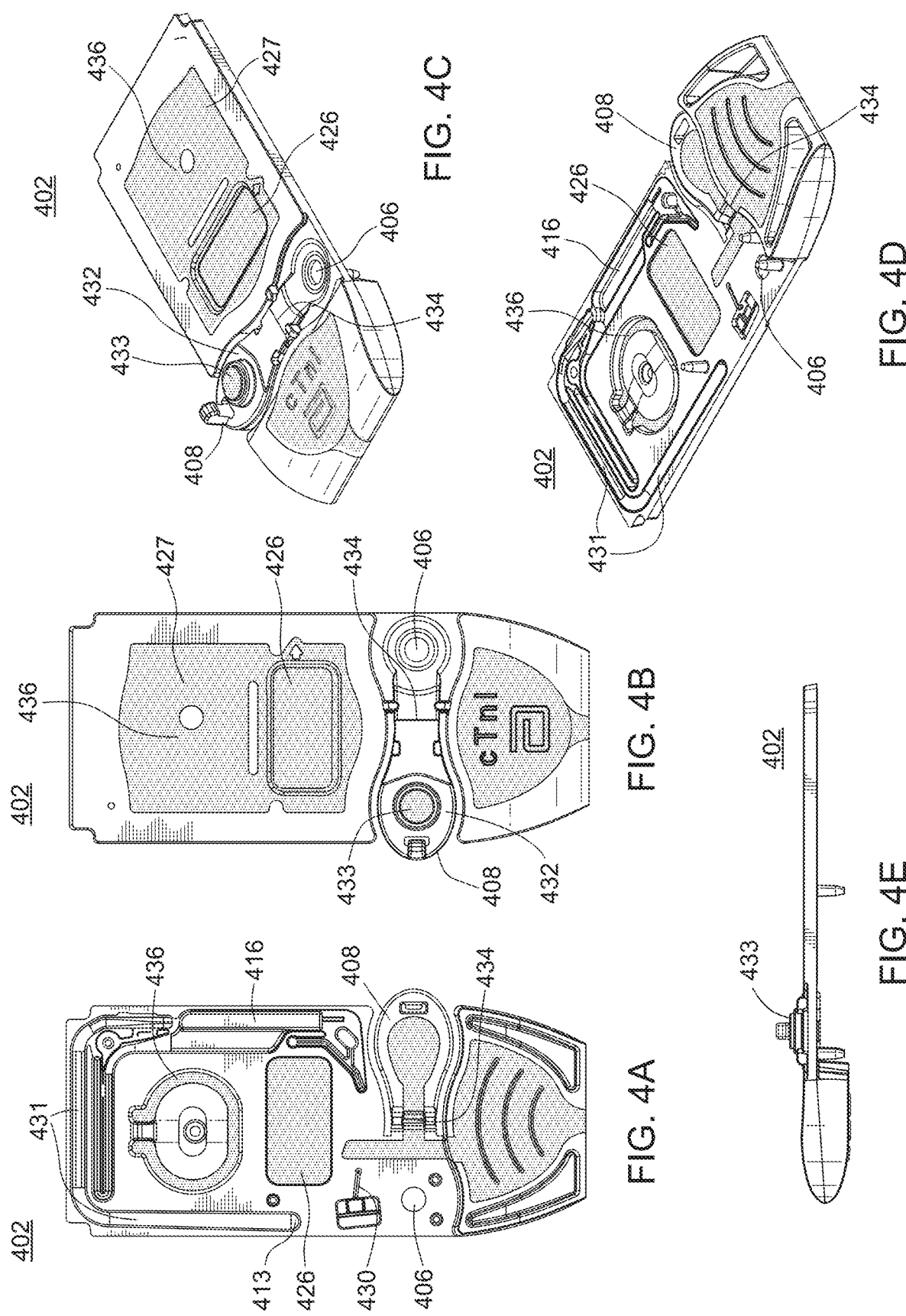

DEVICES, SYSTEMS, AND METHODS FOR PERFORMING OPTICAL ASSAYS

CROSS-REFERENCE TO RELATED APPLICATIONS

This application claims priority to U.S. Provisional Application No. 62/546,713 filed on Aug. 17, 2017, the entirety of which is incorporated herein by reference.

FIELD OF THE INVENTION

This present invention relates generally to devices, systems, and methods for performing optical and electrochemical assays and, more particularly, to devices and systems having universal channel circuitry configured to perform optical and electrochemical assays, and methods of performing the optical and electrochemical assays using the universal channel circuitry.

BACKGROUND OF THE INVENTION

Point-of-care (POC) sample analysis systems are typically based on one or more re-usable hand-held analyzers (i.e., instruments or reading apparatus) that perform sample tests using a single-use disposable testing device, e.g., a cartridge or strip that contains analytical elements, e.g., electrodes or optics for sensing analytes such as pH, oxygen and glucose. The disposable testing device may include fluidic elements (e.g., conduits for receiving and delivering the sample to sensing electrodes or optics), calibrant elements (e.g., aqueous fluids for standardizing the electrodes with a known concentration of analyte), and dyes with known extinction coefficients for standardizing optics. The instrument or reading apparatus may contain electrical circuitry and other components for operating the electrodes or optics, making measurements, and performing computations. The instrument or reading apparatus may also have the ability to display results and communicate those results to laboratory and hospital information systems (LIS and HIS, respectively), for example, via a computer workstation or other data management system. Communication between the instrument or reading apparatus and a workstation, and between the workstation and a LIS or HIS, may be via, for example, an infrared link, a wired connection, wireless communication, or any other form of data communication that is capable of transmitting and receiving electrical information, or any combination thereof. A notable point-of-care system (The i-STAT® System, Abbott Point of Care Inc., Princeton, N.J.) is disclosed in U.S. Pat. No. 5,096,669, which is incorporated herein by reference in its entirety. The i-STAT® System comprises one or more disposable testing devices, operating in conjunction with a hand-held analyzer, for performing a variety of measurements on biological specimens such as blood.

One benefit of point-of-care sample testing systems is the elimination of the time-consuming need to send a sample to a central laboratory for testing. Point-of-care sample testing systems allow a nurse or doctor (user or operator), at the bedside of a patient, to obtain a reliable quantitative analytical result, comparable in quality to that which would be obtained in a laboratory. In operation, the nurse selects a testing device with the required panel of tests, draws a biological sample from the patient, dispenses the biological sample into the testing device, optionally seals the testing device, and inserts the testing device into the instrument or reading apparatus. While the particular order in which the steps occur may vary between different point-of-care systems and providers, the intent of providing rapid sample test results close to the location of the patient remains the same. The instrument or reading apparatus then performs a test cycle, i.e., all the other analytical steps required to perform the tests. Such simplicity gives the doctor quicker insight into a patient's physiological status and, by reducing the turnaround time for diagnosis or monitoring, enables a quicker decision by the doctor on the appropriate treatment, thus enhancing the likelihood of a successful patient outcome.

As discussed herein, point-of-care sample testing systems typically include an instrument or reading apparatus configured to perform sample tests using single-use disposable testing device for the determination of analytes in biological samples. The type of sample tests performed may vary and can be implemented using one or more testing devices including, for example, a qualitative or semi-quantitative testing device (e.g., lateral flow or microarray assays), a quantitative testing device (e.g., an electrochemical assay), or a combined qualitative or semi-quantitative testing device and a quantitative testing device (e.g., a testing device with both lateral flow or microarray assays and an electrochemical assay). In order to perform the one or more tests the instrument or reading apparatus may include an optical sensor configured to process a signal from the qualitative or semi-quantitative testing device and/or an electrical connector configured to process a signal from the quantitative testing device (see, e.g., U.S. Pat. No. 9,194,859, which is incorporated herein by reference in its entirety). In particular, the instrument or reading apparatus may include a first set of circuitry that hardwires a specific set of pins on the electrical connector of the instrument or reading apparatus to a specific means of operation and amplification for processing the signal from the qualitative or semi-quantitative testing device, and/or a second set of circuitry that hardwires a different set of pins on the electrical connector of the instrument or reading apparatus to a different means of operation and amplification for processing the signal from the quantitative testing device.

However, the general use of independent hardwired circuitry in instruments or reading apparatus for each type of testing device, has limited the flexibility in positioning different sensors within the testing device and limited the ability of instruments or reading apparatus to perform multiple types of assays without hardware changes. Hardware changes are typically expensive to implement and can be difficult to manage from generation to generation of instruments or reading apparatus. Accordingly, the need exists for devices, systems, and methods that are capable of performing multiple types of tests or measurements (e.g., optical and electrochemical assays) without having to use independent hardwired circuitry to perform each type of test or measurement.

SUMMARY OF THE INVENTION

In various embodiments, a system is provided for performing an optical assay on a biological sample. The system comprises an analyzer comprising: a port, a multi-terminal connector, a processor, memory coupled to the processor, and universal channel circuitry. The universal channel circuitry is electrically connected to the multi-terminal connector. The system further comprises a test cartridge comprising a plurality of discrete connector contacts, a sample receiving chamber fluidically connected to a conduit, and an analyte assay region comprising: a portion of the conduit, a light emitter, and a light detector. The test cartridge is insertable into the port such that the multi-terminal connector is in electrical contact with the plurality of discrete connector contacts. The memory is encoded with a set of instructions configured to perform the optical assay and at least one of: an amperometric analyte assay, a potentiometric analyte assay, and a conductometric assay. In order to perform the optical assay, (i) the universal channel circuitry is electrically connected to the light emitter via at least one of the plurality of discrete connector contacts and the multi-terminal connector, (ii) the universal channel circuitry is electrically connected to the light detector via at least one of the plurality of discrete connector contacts and the multi-terminal connector, (iii) the universal channel circuitry is configured to drive the light emitter to generate light projected into the portion of the conduit, (iv) the light detector is configured to convert light received from the portion of the conduit to an output signal, and (v) the universal channel circuitry is configured to convert the output signal of the light detector to an analyte signal proportional to the light received from the portion of the conduit. In order to perform at least one of: the amperometric analyte assay, the potentiometric analyte assay, and the conductometric assay, the universal channel circuitry is electrically connectable to at least one of: an amperometric electrode, a potentiometric electrode, and conductometric electrode.

In some embodiments, the light emitter is a light emitting diode (LED) and the light detector is a photodiode (PD), and the test cartridge comprises a plurality of LEDs and a plurality of PDs. In other embodiments, the light emitter is a light emitting diode (LED) and the light detector is a photodiode (PD), and the test cartridge comprises a plurality of paired LEDs and PDs. Optionally, the plurality of paired LEDs and PDs are located at discrete positions with respect to the conduit. Each pair of LEDs and PDs may be substantially optically isolated from the other pairs of LEDs and PDs.

In some embodiments, the processor is configured to determine a qualitative, semi-quantitative, or quantitative value proportional to an amount of a target analyte in the biological sample based on the analyte signal. Optionally, the target analyte is selected from the group consisting of: human chorionic gonadotropin, glucose, lactate, creatinine, urea, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac troponin (cTnI), human chorionic gonadotrophin, troponin T, troponin C, myoglobin, neutrophil gelatinase-associated lipocalin (NGAL), galectin-3, prostate-specific antigen (PSA), parathyroid hormone (PTH), galectin-3, aspartate aminotransferase (AST), alanine aminotransferase (ALT), albumin, total protein, bilirubin, and alkaline phosphatase (ALP).

In some embodiments, the test cartridge further comprises a mirrored reflector that reflects light from the light emitter through the conduit to the light detector. The mirrored reflector may be at least a portion of a surface of the conduit.

In some embodiments, the test cartridge further comprises a filter between the sample receiving chamber and the conduit, and the filter is configured to retain blood cells from the biological sample and permit passage of plasma. The light emitter may emit the light at a wavelength or range of wavelengths selected in the range of 405 nm to 850 nm. Alternatively, the light detector may detect the light at a wavelength or range of wavelengths selected in the range of 400 nm to 1000 nm. Alternatively, the test cartridge further comprises a neutral density light filter.

In some embodiments, the universal channel circuitry comprises a first channel electrically connected to the light emitter via the at least one of the plurality of discrete connector contacts and the multi-terminal connector, and a second channel electrically connected to the light detector via the at least one of the plurality of discrete connector contacts and the multi-terminal connector. Optionally, the first channel includes circuitry configured in a current driver mode and the second channel includes circuitry configured in a current measurement mode. The circuitry of the first channel may comprise a first amplifier connected to a contact of the light emitter, and the circuitry of the second channel comprises a second amplifier connected to a contact of the light detector. The universal channel circuitry may further comprise a third channel electrically connected to the light emitter and/or the light detector via the at least one of the plurality of discrete connector contacts and the multi-terminal connector, the third channel includes circuitry configured in a feedback mode and/or a ground mode, and the circuitry of the third channel comprises a one or more resistors connected to the light emitter and/or ground connected to the light emitter and/or the light detector.

In various embodiments, a system is provided for performing an optical assay for a target analyte in a biological sample. The system comprises an analyzer comprising: a port, a multi-terminal connector, a processor, memory coupled to the processor, and universal channel circuitry. The universal channel circuitry comprises a first channel and a second channel. The system further comprises a test cartridge comprising a sample receiving chamber and a sensor region comprising: a conduit fluidically connected to the sample receiving chamber, a light emitter connected to a first contact, and a light detector connected to a second contact. The memory is encoded with a set of instructions configured to perform the optical assay and at least one of: an amperometric analyte assay, a potentiometric analyte assay, and a conductometric assay. The first contact is electrically connected to a first pin of the multi-terminal connector and the second contact is electrically connected to a second pin of the multi-terminal connector. The first pin is electrically connected to the first channel and the second pin is electrically connected to the second channel. The first channel comprises circuitry including switches that are arranged such that the first channel is configured in a current driver mode. The second channel comprises circuitry including switches that are arranged such that the second channel is configured in a current measurement mode. The switches of the circuitry in the first channel are arrangeable such that the first channel is configured in at least one of: an amperometric measurement mode, a potentiometric measurement mode, and a conductometric measurement mode.

In some embodiments, the first channel is configured to drive the light emitter to generate light projected into a portion of the conduit, the light detector is configured to convert light received from the portion of the conduit to a current output; and the second channel is configured to convert the current output of the light detector to a measurable voltage proportional to the light received from the portion of the conduit. The processor may be configured to determine a qualitative, semi-quantitative, or quantitative value proportional to an amount of target analyte in the biological sample based on the measurable voltage.

In some embodiments, the universal channel circuitry further comprises a third channel, the light emitter and/or the light detector is connected to a third contact, the third contact is electrically connected to a third pin of the multi-terminal connector, the third pin is electrically connected to the third channel, and the third channel comprises circuitry including switches that are arranged such that the third channel is configured in a feedback mode and/or a ground mode.

In various embodiments, a system is provided for performing an optical analyte assay on a biological sample. The system comprises an analyzer comprising: a multi-terminal connector, a processor, and universal channel circuitry, and a test cartridge comprising: a plurality of discrete connector contacts, a sample receiving chamber fluidically connected to a conduit, and an analyte assay region comprising: a portion of the conduit, a light emitter, and a light detector. The universal channel circuitry comprises a first channel connected to a first pin of the multi-terminal connector and a second channel connected to a second pin of the multi-terminal connector. The light emitter is connectable to a first contact of the plurality of discrete connector contacts and the light detector is connectable to a second contact of the plurality of discrete connector contacts and the light detector. The first channel of the analyzer is connectable to: (i) the light emitter to drive the light emitter to generate light projected into the portion of the conduit, (ii) an amperometric electrode, (iii) a potentiometric electrode, or (iv) a conductometric electrode. The second channel of the analyzer is connectable to: (i) the light detector to convert an output signal of the light detector to an analyte signal proportional to the light received from the portion of the conduit, (ii) a reference electrode, or (iii) a conductometric electrode.

In some embodiments, the cartridge further comprises at least one reagent for dissolving into the biological sample. The cartridge may further comprise at least one reagent for dissolving into the biological sample and reacting with an analyte in the biological sample and causing a change in optical absorbance. The light emitter is a light emitting diode (LED) and the light detector is a photodiode (PD), and the LED and PD are mounted on a silicon substrate. Alternatively, the light emitter is a light emitting diode (LED) and the light detector is a photodiode (PD), and the LED and PD are mounted on a transparent plastic substrate. Alternatively, the light emitter is a light emitting diode (LED) and the light detector is a photodiode (PD), and the LED and PD are mounted on a polyester substrate. Alternatively, the light emitter is a light emitting diode (LED) and the light detector is a photodiode (PD), and the LED and PD are mounted a polyimide substrate or printed circuit board.

In some embodiments, the portion of the conduit includes a uniform width dimension in the range of about 0.1 mm to about 4 mm. In other embodiments, the portion of the conduit includes a uniform height dimension in the range of about 0.1 mm to about 4 mm. The cartridge may further comprise a fluid pouch connected to the conduit. Optionally, the fluid pouch comprises a wash fluid, a calibration fluid, or a sample dilution fluid.

In some embodiments, the first channel comprises circuitry including switches that are arranged such that the first channel is configured in a current driver mode, and the second channel comprises circuitry including switches that are arranged such that the second channel is configured in a current measurement mode.

In some embodiments, the universal channel circuitry further comprises a third channel, the light emitter and/or the light detector is connected to a third contact, the third contact is electrically connected to a third pin of the multi-terminal connector, the third pin is electrically connected to the third channel, and the third channel comprises circuitry including switches that are arranged such that the third channel is configured in a feedback mode and/or a ground mode.

In some embodiments, the analyzer is portable or stationary. The analyzer may further comprise a thermal controller for controlling a temperature of the biological sample in the portion of the conduit. The analyzer may be battery powered or line powered.

In various embodiments, an analyzer is provided for performing an optical assay on a biological sample. The analyzer comprises a multi-terminal connector; a processor; memory coupled to the processor; and universal channel circuitry. The universal channel circuitry is electrically connected to the multi-terminal connector. The analyzer further comprises a port for receiving a test cartridge comprising: a plurality of discrete connector contacts connectable to the multi-terminal connector. The memory is encoded with a set of instructions configured to perform the optical assay and at least one of: an amperometric analyte assay, a potentiometric analyte assay, and a conductometric assay. To perform the optical assay, (i) the universal channel circuitry is electrically connected to a light emitter via at least one of the plurality of discrete connector contacts and the multi-terminal connector, (ii) the universal channel circuitry is electrically connected to a light detector via at least one of the plurality of discrete connector contacts and the multi-terminal connector, (iii) the universal channel circuitry is configured to drive the light emitter to generate light projected into a portion of a conduit of the test cartridge, (iv) the light detector is configured to convert light received from the portion of the conduit to an output signal, and (v) the universal channel circuitry is configured to convert the output signal of the light detector to an analyte signal proportional to the light received from the portion of the conduit. To perform at least one of: the amperometric analyte assay, the potentiometric analyte assay, and the conductometric assay, the universal channel circuitry is electrically connectable to at least one of: an amperometric electrode, a potentiometric electrode, and conductometric electrode.

In some embodiments, the processor is configured to determine a qualitative, semi-quantitative, or quantitative value proportional to an amount of a target analyte in the biological sample based on the analyte signal. Optionally, the target analyte is selected from the group consisting of: human chorionic gonadotropin, glucose, lactate, creatinine, urea, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac troponin (cTnI), human chorionic gonadotrophin, troponin T, troponin C, myoglobin, neutrophil gelatinase-associated lipocalin (NGAL), galectin-3, prostate-specific antigen (PSA), parathyroid hormone (PTH), galectin-3, aspartate aminotransferase (AST), alanine aminotransferase (ALT), albumin, total protein, bilirubin, and alkaline phosphatase (ALP).

BRIEF DESCRIPTION OF THE DRAWINGS

The present invention will be better understood in view of the following non-limiting figures.

FIGS. 3 and 4A-4J show a testing device or cartridge in accordance with various embodiments;

DETAILED DESCRIPTION OF THE INVENTION

Introduction

Figure 1:
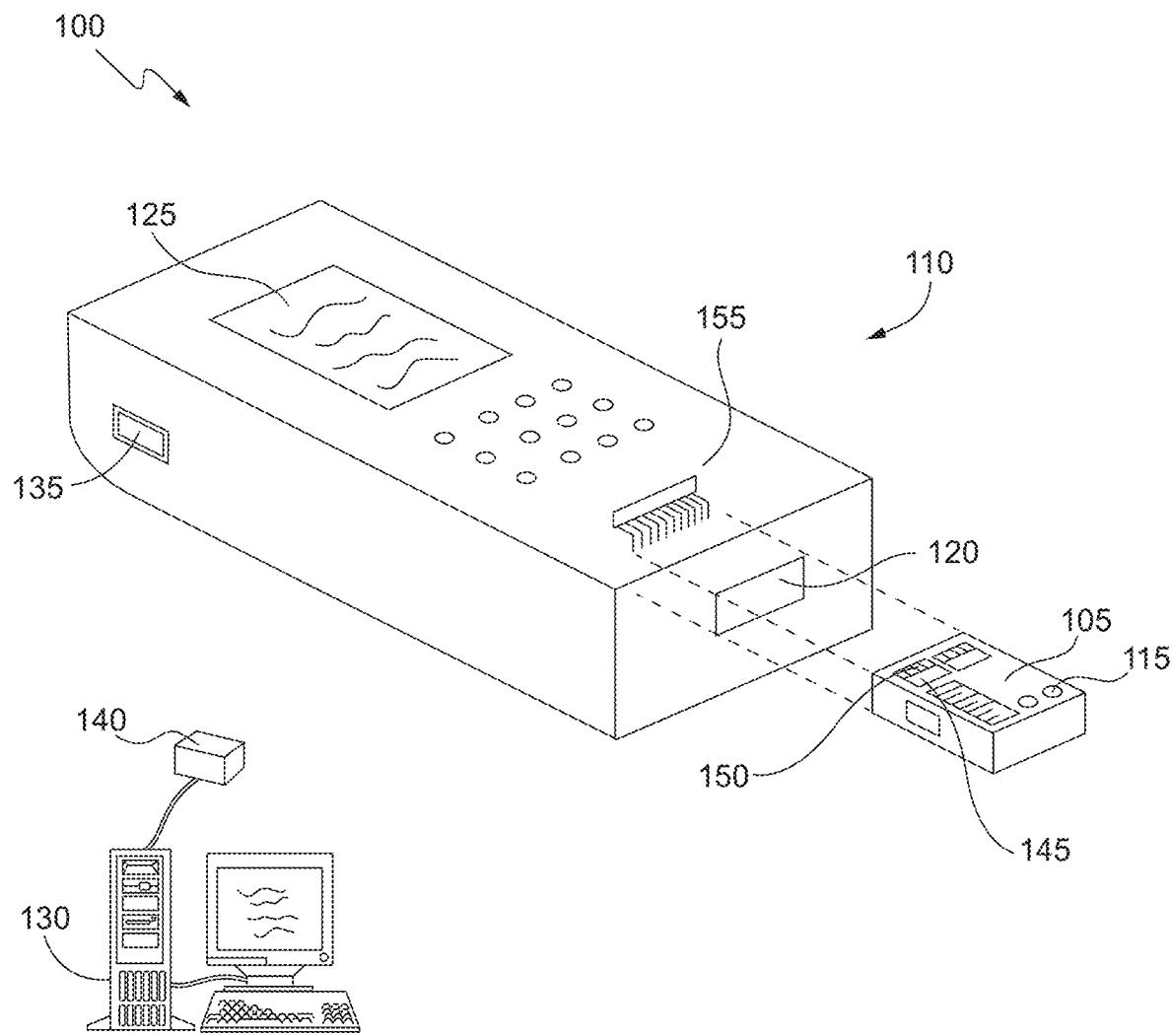
FIG. 1 shows a disposable testing device and instrument in accordance with various embodiments.

Various embodiments of the present invention are directed to devices, systems, and methods for performing optical and electrochemical assays. For example, FIG. 1 shows an exemplary system 100 that may comprise a self-contained disposable testing device or cartridge 105 and an instrument or reading apparatus 110 (e.g., an analyzer) that is portable or stationary and battery powered or line powered. In some embodiments, the testing device 105 is a single-use device configured to be disposable after the single-use. A fluid sample (e.g., whole blood) to be measured is drawn into a sample receiving chamber via a sample entry orifice 115 in the testing device 105, and the testing device 105 may be inserted into the analyzer 110 through a port 120. The analyzer 110 may comprise a processor configured to perform processes including the measurement of analyte concentrations, the measurement of resistances, the control of a temperature of a biological sample, the conversion of current output to a measurable voltage, and the identification of analytes or sets of analytes that a chip is configured to measure. Measurements and determinations performed by the analyzer 110 may be output to a display 125 or other output device, such as a printer or data management system 130 via a port 135 on the analyzer 110 to a computer port 140. Transmission can be via wired or wireless communication such as a telephone network, Internet connection, Wi-Fi, Bluetooth link, infrared and the like. The sensors 145 (e.g., an electrochemical sensor and/or an optical sensor) in the testing device 105 include a plurality of discrete connector contacts 150 that make electrical contact with the analyzer 110 via a multi-terminal connector 155 when the testing device 105 is inserted into the port 120. For example, the multi-terminal connector 155 may be of the design disclosed in U.S. Pat. No. 4,954,087, which is incorporated herein by reference in its entirety. The analyzer 110 may also be configured to perform a method for automatic fluid flow compensation in the testing device 105, as disclosed in U.S. Pat. No. 5,821,399, which is also incorporated herein by reference in its entirety.

In conventional instruments or reading apparatus, the multi-terminal connector has a linear array of pins, which mate with a linear array of discrete connector contacts in the testing device. A problem associated with these conventional instruments or reading apparatus is that each pin is hardwired to an assigned function, and thus there is limited flexibility in positioning the different sensors within a cartridge. For example, the connector pad of a potassium electrode on a testing device needs to be aligned to one of the potentiometric working electrode pins on the connector. Another limitation of the conventional instruments or reading apparatus is that they only have a limited number of measurement pins (e.g., amperometric pins), and future testing devices may need to perform multiple tests or measurements. For example, a dual immunoassay cartridge, each with its own immuno-reference sensor, may need four amperometric channels. Consequently, the limitations imposed by the hardwired design of the conventional instruments or reading apparatus adversely affects the capability of the instruments or reading apparatus to perform multiple tests or measurements without hardware changes.

To address these problems, various embodiments described herein are directed to devices and systems having universal channel circuitry configured to perform optical and electrochemical assays (e.g., amperometric analyte assays, potentiometric analyte assays, or conductometric assays), and methods of performing the optical and electrochemical assays using the universal channel circuitry. The universal channel circuitry is distinct in that it is not hard wired in certain aspects. Instead, the "universal channel circuitry", as used herein, is defined as circuitry that has electronic switching capabilities such that any contact pin, and thus any sensor contact pad in a testing device, can be connected to one or more channels capable of taking on one or more measurement modes or configurations (e.g., twelve potentiometric channels, four amperometric channels, one of two conductometric channels, etc.). In particular and in accordance with various aspects of the present invention, hardwired circuitry typically configured to operate amperometric, potentiometric, and conductometric sensors independently has been further developed to operate amperometric, potentiometric, and conductometric sensors universally, and additionally operate light emitting diodes (LED) and photodiodes (PD) for performing optical assays in testing devices, as discussed in further detail herein.

In one embodiment, a system is provided for performing an optical assay on a biological sample. The system includes (i) an analyzer comprising: a port, a multi-terminal connector, a processor, memory coupled to the processor, and universal channel circuitry, where the universal channel circuitry is electrically connected to the multi-terminal connector, and (ii) a test cartridge comprising a plurality of discrete connector contacts, a sample receiving chamber fluidically connected to a conduit, and an analyte assay region comprising: a portion of the conduit, a light emitter such as a light emitting diode (LED), and a light sensor or detector such as a photodiode (PD). The test cartridge is insertable into the port such that the multi-terminal connector is in electrical contact with the plurality of discrete connector contacts. The memory is encoded with a set of instructions configured to perform the optical analyte assay and at least one of: an amperometric analyte assay, a potentiometric analyte assay, and a conductometric assay. In order to perform the optical analyte assay, (i) the universal channel circuitry is electrically connected to the light emitter via at least one of the plurality of discrete connector contacts and the multi-terminal connector, (ii) the universal channel circuitry is electrically connected to the light detector via at least one of the plurality of discrete connector contacts and the multi-terminal connector, (iii) the universal channel circuitry is configured to drive the light emitter to generate light projected into the portion of the conduit, (iv) the light detector is configured to convert light received from the portion of the conduit to an output signal, and (v) the universal channel circuitry is configured to convert the output signal of the light detector to an analyte signal proportional to the light received from the portion of the conduit. In order to perform at least one of: the amperometric analyte assay, the potentiometric analyte assay, and the conductometric assay, the universal channel circuitry is electrically connectable to at least one of: an amperometric electrode, a potentiometric electrode, and conductometric electrode.

Advantageously, these approaches provide devices, systems, and methods with greater flexibility in testing device design including: (i) the combination of tests in any give testing device, (ii) the combination of tests on any given sensor chip, (iii) the position of sensors within the testing device, (iv) extending utility of the analyzers to perform various types of assays without hardware changes, and (v) increasing the point-of-care testing opportunities. In addition, these approaches may also reduce the number of different testing device bases (which accommodate the sensor chips) used to manufacture all the different testing devices for the various test.

System Environment

Figure 2:
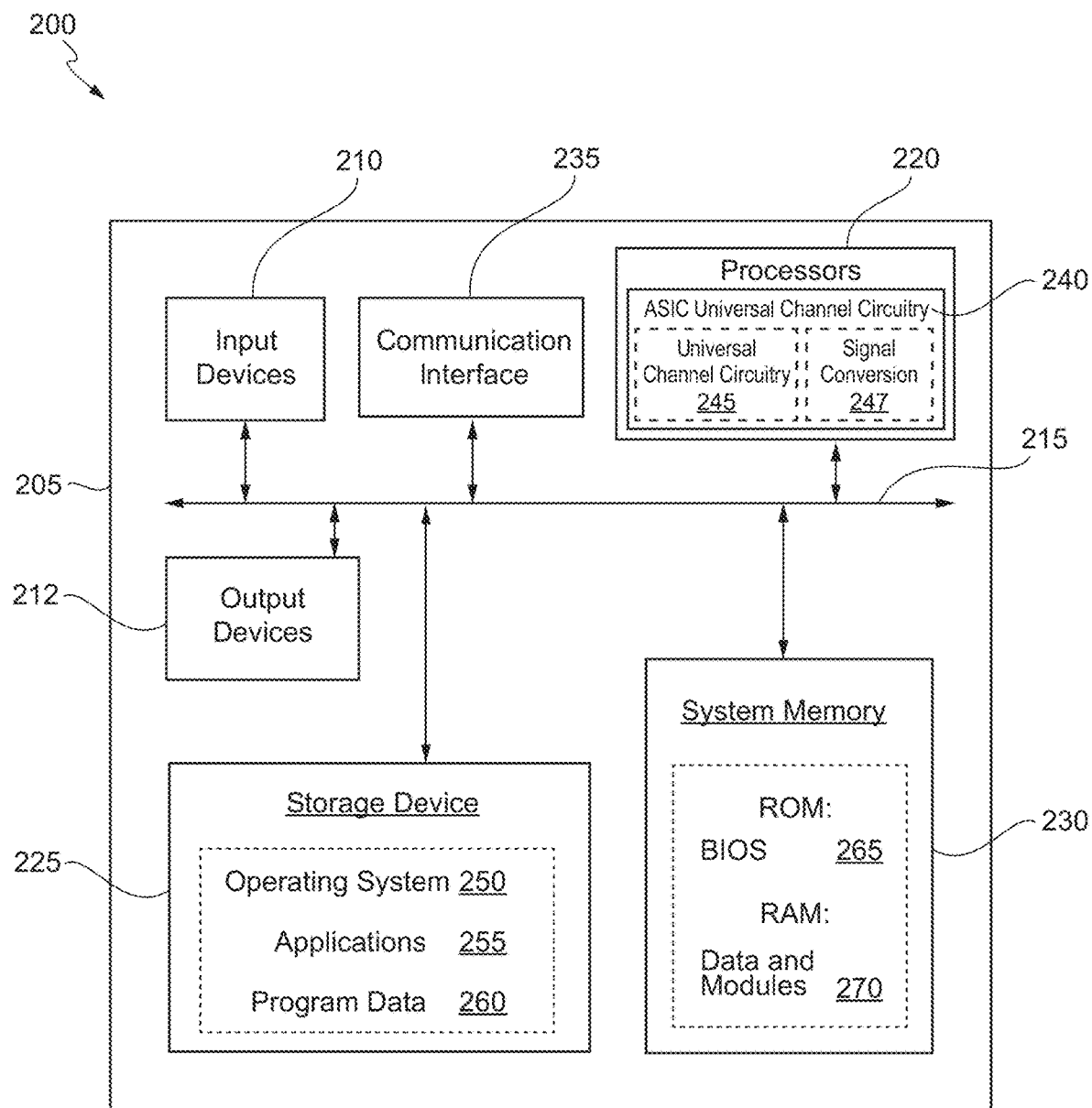
FIG. 2 shows an illustrative architecture of a computing system implemented in accordance with various embodiments.

FIG. 2 is an illustrative architecture of a computing system 200 implemented in various embodiments. The computing system 200 is only one example of a suitable computing system and is not intended to suggest any limitation as to the scope of use or functionality of the various embodiments. Also, computing system 200 should not be interpreted as having any dependency or requirement relating to any one or combination of components illustrated in computing system 200.

As shown in FIG. 2, computing system 200 includes a computing device 205. The computing device 205 can be resident on a network infrastructure such as within a cloud environment, or may be a separate independent computing device (e.g., a computing device implemented within the environment of an analyzer such as analyzer 110 as described with respect to FIG. 1)). The computing device 205 may include one or more input devices 210, one or more output devices 212, a bus 215, processor 220, a storage device 225, a system memory (hardware device) 230, and a communication interface 235.

The one or more input devices 210 may include one or more mechanisms that permit an operator to input information to computing device 205, such as, but not limited to, a touch pad, dial, click wheel, scroll wheel, touch screen, one or more buttons (e.g., a keyboard), mouse, game controller, track ball, microphone, camera, proximity sensor, light detector, motion sensors, biometric sensor, and combinations thereof. The one or more output devices 212 may include one or more mechanisms that output information to an operator, such as, but not limited to, audio speakers, headphones, audio line-outs, visual displays, antennas, infrared ports, tactile feedback, printers, or combinations thereof.

The bus 215 permits communication among the components of computing device 205. For example, bus 215 may be any of several types of bus structures including a memory bus or memory controller, a peripheral bus, and a local bus using any of a variety of bus architectures to provide one or more wired or wireless communication links or paths for transferring data and/or power to, from, or between various other components of computing device 205.

The processor 220 may be one or more integrated circuits, printed circuits, controllers, microprocessors, or specialized dedicated processors that include processing circuitry operative to interpret and execute computer readable program instructions, such as program instructions for controlling the operation and performance of one or more of the various other components of computing device 205 for implementing the functionality, steps, and/or performance of the embodiments discussed herein. In certain embodiments, processor 220 interprets and executes the processes, steps, functions, and/or operations, which may be operatively implemented by the computer readable program instructions. For example, processor 220 can receive a signal indicative of a type of test cartridge; determine, based on the type of test cartridge, that the test cartridge has a first contact connected to a light emitter and a second contact connected to a light detector; assign a first channel to the light emitter via the first contact and a corresponding first pin; assign a second channel to the light detector via the second contact and a corresponding second pin; switch the circuitry of the first channel to a current driver mode; switch the circuitry of the second channel to an current measurement mode; apply, using the first channel, a drive current to the light emitter; convert, using the second channel, an output signal received from the light detector to a measurable voltage or analyte signal proportional to an amount of light detected by the light detector; and determine a qualitative, semi-quantitative, or quantitative value proportional to an amount of target analyte in the biological sample or specimen based on the measurable voltage or the analyte signal. In some embodiments, the information obtained or generated by the processor 220, e.g., type of test cartridge, circuit configurations for the channels including whether each switching element should be switched on/off, a tally for various operations, output current, look-up tables, potential to be applied, etc., can be stored in the storage device 225. In certain embodiments, the processor 220 may comprise a thermal controller for controlling a temperature of the biological sample or specimen in a portion of a conduit.

In various embodiments, the processor 220 comprises an application-specific integrated circuit 240 that includes the universal channel circuitry 245, and analog to digital signal converter 247. In other embodiments, the processor 220 is in communication with the application-specific integrated circuit 240 that includes the universal channel circuitry 245. The application-specific integrated circuit 240 is an integrated circuit (IC) customized for performing a number of functions including an analog to digital signal interface, current to voltage conversion, multiplexing, resistor selection, signal amplification, potential and conductance generation and/or measurement, and the performance of multiple types of assays. The universal channel circuitry 245 includes circuitry that can be implemented in conjunction with computer readable program instructions, data structures, program modules and other data to switch between various modes or configurations (e.g., a potentiometric mode, an amperometric mode, a conductance mode, an optical mode, etc.) and contribute to the performance of multiple types of assays.

The storage device 225 may include removable/non-removable, volatile/non-volatile computer readable media, such as, but not limited to, non-transitory machine readable storage medium such as magnetic and/or optical recording media and their corresponding drives. The drives and their associated computer readable media provide for storage of the computer readable program instructions, data structures, program modules and other data for operation of computing device 205. In various embodiments, storage device 225 may store operating system 250, application programs 255, and/or program data 260. In some embodiments, the application programs 255, and/or program data 260 may include a database, index, or table, and algorithms, for example, qualitative, semi-quantitative, or quantitative value algorithms that include components for determining a presence and/or amount of target analyte in a biological specimen or sample, a position determining algorithm for determining the location of a biological sample within a test device based on detected conductance, and a hematocrit determination algorithm for determining a hematocrit of a biological sample based on detected conductance across a biological sample, which provide the instructions for execution of processor 220.

The system memory 230 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system 265 (BIOS) including the basic routines that help to transfer information between the various other components of computing device 205, such as during start-up, may be stored in the ROM. Additionally, data and/or program modules 270, such as at least a portion of operating system 250, application programs 255, and/or program data 260, that are accessible to and/or presently being operated on by processor 220, may be contained in the system memory 230.

The communication interface 235 may include any transceiver-like mechanism (e.g., a network interface, a network adapter, a modem, or combinations thereof) that enables computing device 205 to communicate with remote devices or systems, such as other analyzers, a hospital information system, a mobile device or other computing devices such as, for example, a server in a networked environment, e.g., cloud environment. For example, computing device 205 may be connected to remote devices or systems via one or more local area networks (LAN) and/or one or more wide area networks (WAN) using communication interface 235.

As discussed herein, computing system 200 may be configured to perform one or more analytical tests (e.g., an optical assay and/or an electrochemical assay). In particular, computing device 205 may perform tasks (e.g., process, steps, methods and/or functionality) in response to processor 220 executing program instructions contained in non-transitory machine readable storage medium, such as system memory 230. The program instructions may be read into system memory 230 from another computer readable medium (e.g., non-transitory machine readable storage medium), such as data storage device 225, or from another device via the communication interface 235 or server within or outside of a cloud environment. In some embodiments, hardwired circuitry of computing system 200 may be used in place of or in combination with the program instructions to implement the tasks, e.g., steps, methods and/or functionality, consistent with the different aspects discussed herein. Thus, the steps, methods and/or functionality disclosed herein can be implemented in any combination of hardware circuitry and software.

Testing Device or Cartridge

Figure 3:
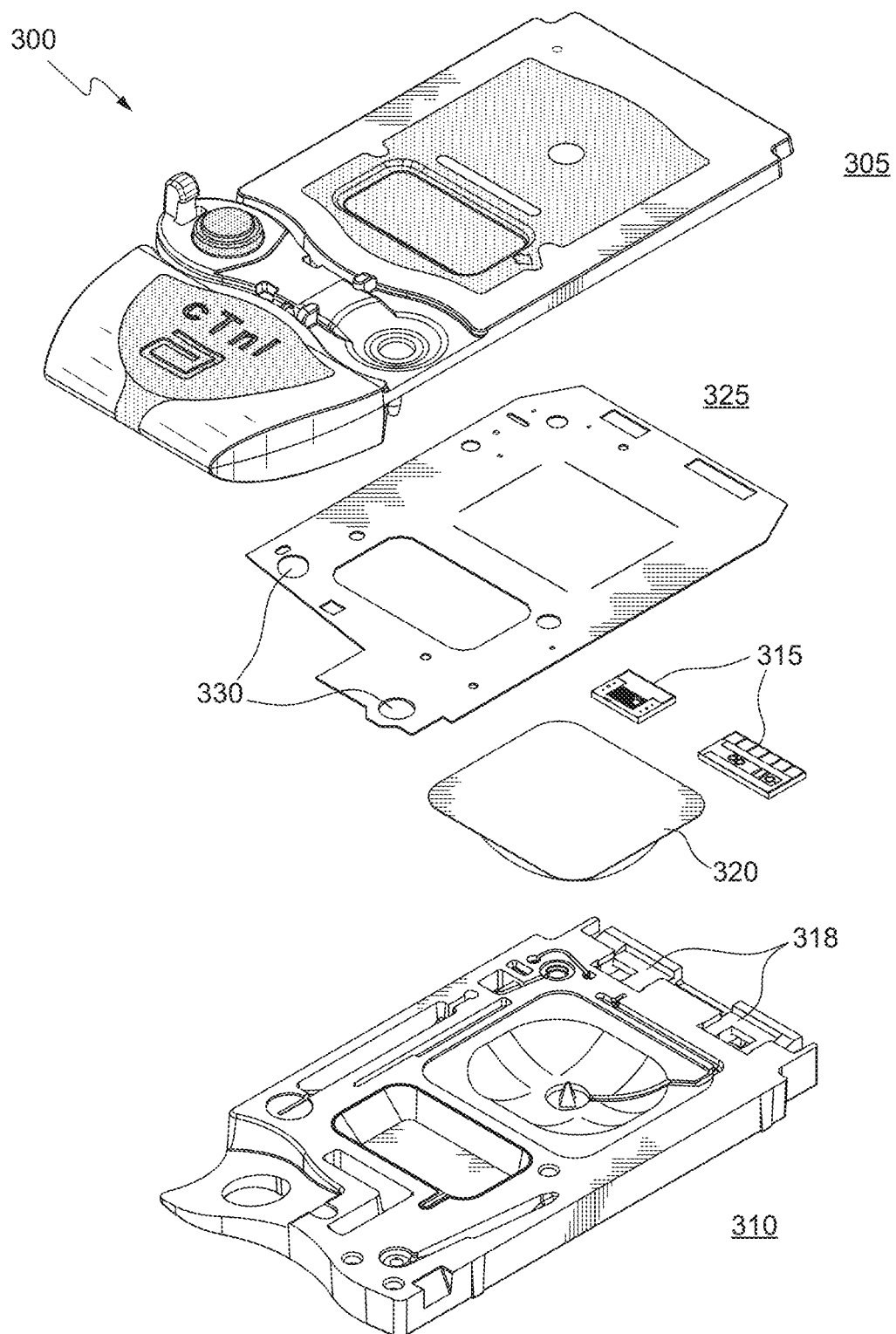
Figure 4H:
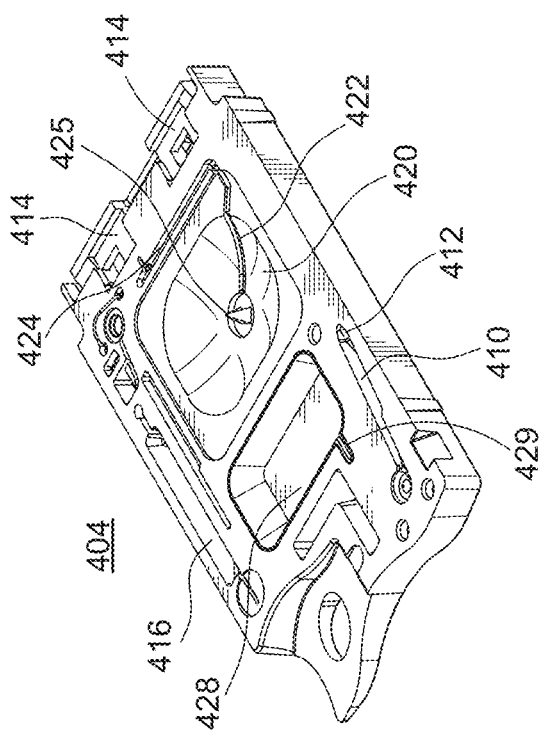
Figure 4I:
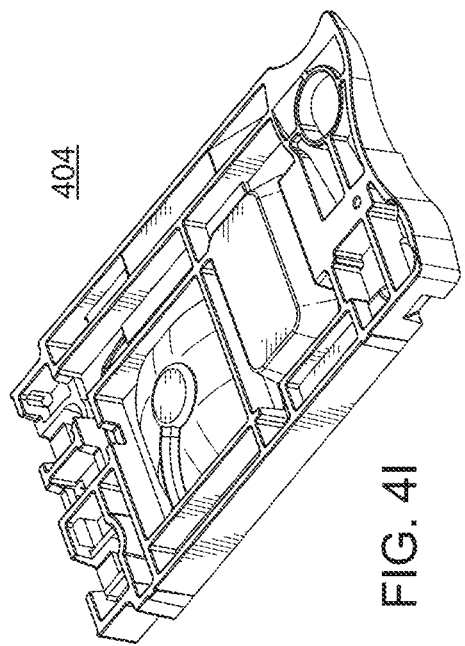
Figure 4G:
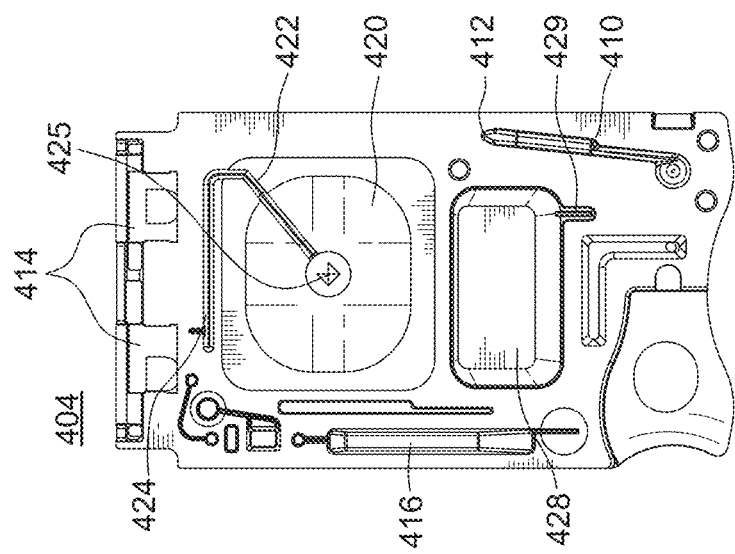
Figure 4F:
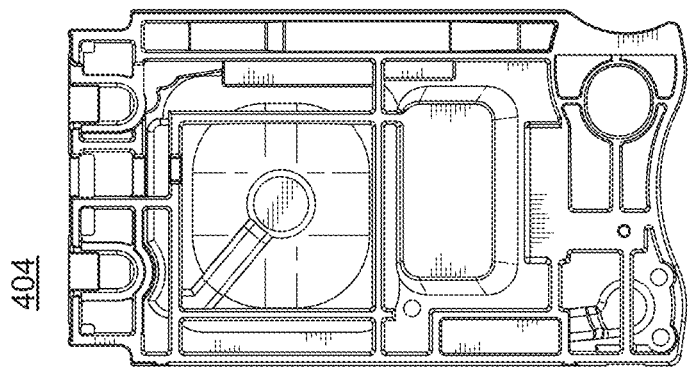
Figure 4J:

In one embodiment, as shown in FIG. 3, a testing device or cartridge 300 (e.g., testing device 105 as described with respect to FIG. 1) comprises a top portion 305 (e.g., a cover) and a bottom portion 310 (e.g., a base) in which are mounted at least one microfabricated sensor chip 315 with electrical contacts and a pouch 320 containing a fluid, e.g., a calibrant fluid, a diluent fluid and/or a wash fluid. The at least one sensor chip 315 may be positioned in recessed region 318 and configured to generate electric signals based on a concentration of specific chemical species in a fluid sample, e.g., a blood sample from a patient. In some embodiments, the composition of the fluid in the pouch 320 is selected from the group consisting of water, calibrant fluid, reagent fluid, control fluid, wash fluid and combinations thereof. A gasket 325 may be situated between the top portion 305 and the bottom portion 310 to bond them together, and to define and seal several cavities and conduits within the cartridge 300. The gasket 325 may cover substantially the entire area between the top portion 305 and the bottom portion 310 of the cartridge 300, as shown in FIG. 3, or may be localized over and between only predetermined structural features, e.g., at least one sensor chip 315 of the cartridge 300 (not shown). The gasket 325 may include apertures 330 to enable physical, fluidic and/or gaseous communication between structural features of the top portion 305 and the bottom portion 310. The gasket 325 may or may not have an adhesive surface, and may have an adhesive surface on both sides thereof, i.e., forming a double-sided adhesive layer.

As shown in FIGS. 4A-4J, in some embodiments, the testing device or cartridge 400 (e.g., cartridge 300 as described with respect to FIG. 3) has a housing that comprises a top portion 402 (e.g., a cover) and a bottom portion 404 (e.g., a base) formed of rigid and flexible zones of material. As shown in FIGS. 4A-4J, the rigid zones (non-shaded portions) of the cover 402 and the base 404 respectively are preferably each a single contiguous zone; however, the molding process can provide a plurality of non-contiguous substantially rigid zones. The flexible zones (shaded portions) of the cover 402 and the base 404 respectively are preferably a set of several non-contiguous zones. For example, the flexible zone around a displaceable membrane may be separate and distinct from the flexible zone at a closeable sealing member. Alternatively, the flexible zones may comprise a single contiguous zone.

The sensing device or cartridge 400 further comprises a sealable sample entry port 406 and a closable sealing member 408 for closing the sample entry port 406, a sample receiving chamber 410 located downstream of the sample entry port 406, a capillary stop 412, an optional filter 413 between the sample receiving chamber 410 and a sensor region 414 (i.e., analyte assay region), and a waste chamber 416 located downstream of the sensor region 414. The filter 413 may be configured to retain blood cells from a biological sample and permit passage of plasma into the sensor region 414. Preferably, the cross-sectional area of a portion of the sample receiving chamber 410 decreases distally with respect to the sample entry port 406. A pouch (e.g., the pouch 320 described with respect to FIG. 3) may be disposed in a recessed region 420 and in fluid communication with a conduit 422 leading to the sensor region 414, optionally via conduit 424. The pouch may be of the design described in U.S. Pat. No. 5,096,669 or, more preferably, in U.S. Pat. No. 8,216,529, both of which are incorporated herein by reference in their entireties. Recessed region 420 preferably includes a spike 425 configured to rupture the pouch, upon application of a force upon the pouch, for example, by reader or analyzer (e.g., analyzer 110 as described with respect to FIG. 1). Once the pouch is ruptured, the system is configured to deliver the fluid contents from the pouch into conduit 422. Movement of the fluid into the conduit 422 and to the sensor region 414 and/or within the conduit 424 may be effected by a pump, e.g., a pneumatic pump connected to the conduit(s) 422 or 424. Preferably, the pneumatic pump comprises a displaceable membrane 426 formed by a portion of a flexible zone 427 of the housing formed over a recessed region or air bladder 428. In the embodiment shown in FIGS. 4A-4J, upon repeatedly depressing the displaceable membrane 426, the device pumps via conduits 429 and 430 causing fluid from the ruptured pouch to flow through the conduit 422, optionally into the conduit 424, and over the sensor region 414 via conduit 431.

The closable sealing member 408, in some embodiments, includes a portion of the rigid zone that forms a sealing member 432, and a portion of the flexible zone that forms a seal 433. The sealing member 408 can rotate about hinge 434 and engage the seal 433 with the sample entry port 406 when in a closed position, thus providing an air-tight seal. Alternatively, an air-tight seal may be formed by contact of two flexible materials, e.g., a thermoplastic elastomer (TPE) on TPE. Optionally, the sealable sample entry port 406 also includes a vent hole (not shown). In an alternative embodiment, a portion of the rigid zone forms a sealing member, and a portion of the flexible zone forms a perimeter seal around the sample entry port, whereby the sealing member can rotate about a hinge and engage the perimeter seal when in a closed position, thus providing an air-tight seal. Alternatively, the perimeter seal may be formed by contact of two flexible materials. In yet another embodiment, the sealing member may include a slidable closure element as described in pending U.S. Pat. No. 7,682,833, the entirety of which is incorporated herein by reference.

The sensor region 414, in some embodiments, contains a sensor array comprising one or more sensors for one or more different analytes (or blood tests). For example, the sensor array may include an electrochemical sensor and/or an optical sensor for one or more different analytes (or blood tests). The electrochemical sensor may include a base sensor or sensing electrode on a substantially planar chip (e.g., a microfabricated sensor chip such as the at least one sensor chip 315 described with respect to FIG. 3) where the sensing electrode is positioned in conduit 431 for receiving a sample mixed with a reagent. The optical sensor may include one or more light emitters (e.g., LEDs) and one or more light detectors (e.g., PDs) on a substantially planar chip (in some embodiments the same sensor chip that includes the electrochemical sensor) where the one or more light emitters and one or more light detectors are positioned near the conduit 431 for transmitting and receiving light through the conduit 431 comprising a sample optionally mixed with reagent. In alternative embodiments, the sensor array comprises a plurality of sensors for a plurality of different analytes (or blood tests). Accordingly, the cartridge 400 may have one or more sensor regions 414 each with at least one sensor.

Preferably, at least a portion of the conduit 431 includes a uniform width dimension in the range of about 0.1 mm to about 4 mm, and a uniform height dimension in the range of about 0.1 mm to about 4 mm. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent.

In various embodiments, the sensor recess 414 comprises a plurality of LEDs and a plurality of PDs. The plurality of LEDs and the plurality of PDs may be paired up such that the sensor recess 414 comprises a plurality of paired LEDs and PDs. The plurality of LEDs and PDs or plurality of paired LEDs and PDs may be located at discrete positions with respect to the conduit 431. In certain embodiments, each pair of LEDs and PDs is substantially optically isolated from the other pairs of LEDs and PDs. For example, the pairs of LEDs and PDs may be spaced a predetermined distance from one another and/or include a filtering structure between one another such that each pair of LEDs and PDs is substantially optically isolated from the other pairs of LEDs and PDs.

The analytes/properties to which the sensors respond may be selected from among human chorionic gonadotropin, pH, partial pressure $CO_2$, partial pressure $O_2$, glucose, lactate, creatinine, urea, sodium, potassium, chloride, calcium, magnesium, phosphate, hematocrit, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac troponin (cTnI), human chorionic gonadotrophin, troponin T, troponin C, myoglobin, neutrophil gelatinase-associated lipocalin (NGAL), galectin-3, prostate-specific antigen (PSA), parathyroid hormone (PTH), galectin-3, aspartate aminotransferase (AST), alanine aminotransferase (ALT), albumin, total protein, bilirubin, alkaline phosphatase (ALP), and the like, and combinations thereof. Preferably, the analyte is tested in a liquid sample that is whole blood, however other samples can be used including blood, serum, plasma, urine, cerebrospinal fluid, saliva and amended forms thereof. Amendments can include dilution, concentration, addition of regents such as anticoagulants and the like. Whatever the sample type, it can be accommodated by the sample entry port 406 of the cartridge 400.

The cartridge 400 may further comprise a portion 426 of the flexible zone 436 positioned over the recessed region 420 that is configured for being actuated upon like a pump to apply pressure within the recessed region 420. In some embodiments, the flexible zone 436 may include a generic symbol description to indicate to the user that pressure should not be applied to the flexible zone 436 by the user. For example, the symbol may comprise an embossed circle with a crossbar. The portion of the flexible zone 436 provides a surface that can accommodate an actuator feature of the analyzer (e.g., analyzer 110 as described with respect to FIG. 1) to apply a force and burst the underlying pouch in the recessed region 420. The thickness of the plastic in the flexible zone 436 may be preferably from about 200 to about 800 μm, for example about 400 μm. Essentially, the flexible zone 436 should be sufficiently thin to flex easily, but sufficiently thick to maintain physical integrity and not tear.

Sensor and Chip Designs

In one embodiment, a microfabricated sensor chip (e.g., the at least one sensor chip 315 described with respect to FIG. 3) comprises at least one sensor or transducer (e.g., an electrochemical sensor and/or optical sensor). For example, the microfabricated sensor chip may comprise an electrochemical sensor or an optical sensor. Alternatively, the microfabricated sensor chip may comprise a sensory array including at least a first sensor (e.g., an electrochemical sensor) and a second sensor (e.g., an optical sensor). In some embodiments, the sensors may be fabricated singularly, or as adjacent structures within a sensor array, on a silicon chip, a plastic, polyester, polyimide, or silicon planar substrate, a plastic, polyester, polyimide, or silicon substrate, a transparent plastic, polyester, polyimide, or silicon substrate, a printed circuit board (PCB), and the like.

Figure 5A:
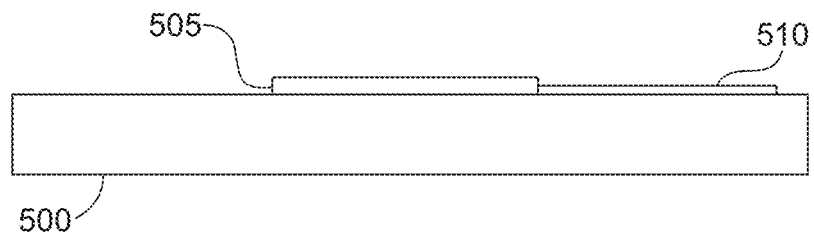
FIG. 5A shows a side view of the fabrication of an electrochemical sensor chip in accordance with various embodiments.

In various embodiments, one or more of the electrochemical sensors may be formed as electrodes with gold surfaces coated with a photo defined polyimide layer that includes openings to define a grid of small gold electrodes (e.g., a gold microarray electrode) at which an electroactive species may be oxidized. For example, wafer-level micro-fabrication of a preferred embodiment of the sensor chip may be achieved as shown in FIG. 5A. A non-conducting substrate 500 having a planar top and bottom surface may be used as a base for the sensor chip. A conducting layer 505 may be deposited on the substrate 500 by conventional means, e.g., screen printing, or micro-fabrication technique known to those of skill in the art to form at least one component (e.g., a microarray electrode). The conducting layer 505 may comprise a noble metal such as gold, platinum, silver, palladium, iridium, or alloys thereof, although other unreactive metals such as titanium and tungsten or alloys thereof may also be used, as many non-metallic electrodes of graphite, conductive polymer, or other materials may also be used. The microfabricated sensor chip may also comprise an electrical connection 510 that connects the electrode to a conductive pin such as a temporary (make and break) electrical connector.

In some embodiments, the one or more of the electrochemical sensors may comprise an array of 5-10 μm noble metal disks, e.g., 7 μm noble metal disks, on 15 μm centers. The array of noble metal disks or electrodes may cover a region, e.g., a circular region, approximately 300 to 900 μm in diameter, optionally 400-800 μm or about 600 μm in diameter, and may be formed by photo-patterning a thin layer of polyimide or photoresist of thickness up to 1.5 μm over a substrate made from a series of layers comprising Si,SiO2,TiW, and/or Au, or combinations thereof. In some embodiments, the electrodes have a working area of about 130,000 to 300,000 sq μm (i.e., a microelectrode), the volume of sample directly over the electrodes may be about 0.1-0.3 μL, and the volume of the sample over the sensor chip may be 1-3 μL. In accordance with these aspects of the present invention, the conduit (e.g., the conduit 431 described with respect to FIG. 4A) in a region of the electrodes (e.g., the one or more sensor recesses 414 described with respect to FIGS. 4A-4J) has a volume to sensor area ratio of less than about 6 μL to about 1 square mm.

Figure 5B:
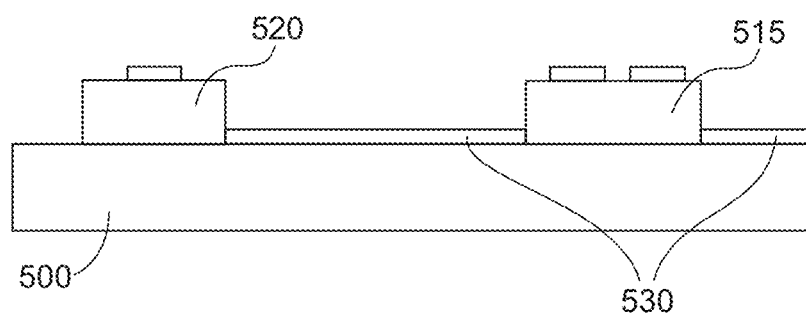
FIG. 5B shows a side view of the fabrication of an optical sensor chip in accordance with various embodiments.

In various embodiments, one or more of the optical sensors may be formed as one or more light emitters (e.g., LEDs) and one or more light detectors (e.g., PDs) on a substantially planar chip (in some embodiments the same sensor chip that includes the electrochemical sensor). For example, wafer-level micro-fabrication of a preferred embodiment of the sensor chip may be achieved as shown in FIG. 5B. A non-conducting substrate 500 having a planar top and bottom surface may be used as a base for the sensor chip. One or more light emitters 515 and one or more light detectors 520 may be provided or formed on the substrate 500 by conventional means, e.g., a micro-fabrication technique known to those of skill in the art to form at least one emitter and detector. The microfabricated sensor chip may also comprise an electrical connection 525 (e.g., an electrical connection comprising a plurality of discrete contacts) that connects the one or more light emitters 515 and the one or more light detectors 520 to one or more conductive pins such as a temporary electrical connector.

In some embodiments, the one or more light emitters 515 are comprised of LEDs. For example, multiple wavelength LEDs, e.g., from 405 nm (near ultra-violet light)-850 nm (near infrared), may be used to cover a variety of tests or a single wavelength LED may be used to increase illumination power. Typical wavelengths for measurements (deltas of absorbance) of various analytes are known and depend on the actual assay design, for example 467 and 550 nm for total bilirubin, 600 and 550 nm for albumin, 550 and 850 nm for total protein, and 400 and 460 nm to distinguish conjugated and unconjugated bilirubin. Selection of wavelengths such as these may be achieved by one of ordinary skill in the art. Alternatively, other light sources with or without filters may be used without departing from the spirit and scope of the present invention. The size of the LEDs may be selected to fit with other components (e.g., the conduits or sensor region) of the testing device, e.g., LEDS available as surface mount (SMD) and chip scale packaging (CSP) may be used to fit a variety of testing devices. Typical low profile chip LEDs have the industry standard 1.6 mm×0.8 mm footprint, which provides high efficiency light projection and low power consumption. LEDs are typically current driven and require voltages greater than 2V and current less than 1 mA to turn on. In accordance with various aspects of the present invention, the drive of the LEDs may be within the range of 1V-5V and 0.1-1.5 mA, for example substantially 3V and 0.5 mA.

In some embodiments, the one or more light detectors 520 are comprised of a PD(s), e.g., a silicon photo PIN diode(s) having an undoped intrinsic semiconductor region sandwiched between a p-type semiconductor region and an n-type semiconductor region. The spectral response of the PIN diode may be in the range of 400 nm to 1000 nm. Alternatively, other light sensors or detectors with or without filters to control wavelengths may be used without departing from the spirit and scope of the present invention This provides the capability to cover a wide spectrum of LED wavelengths. The size of the PIN diode may be selected to fit with other components (e.g., the conduits or sensor region) of the testing device, e.g., the PIN diode available as surface mount (SMD) and chip scale packaging (CSP) may be used to fit a variety of testing devices. Typical a low profile PIN diode has the industry standard 2.0 mm×1.25 mm footprint, which provides high efficiency light detection and low power consumption. In accordance with various aspects of the present invention, the sensitivity of the PIN diode may be within the range of 0.5 uA/cm$^2$-4 uA/cm$^2$, for example substantially 1 uA/cm$^2$.

Micro-fabrication techniques (e.g., photolithography and plasma deposition) may be utilized for construction of the multilayered sensor structures in confined spaces. For example, methods for micro-fabrication of electrochemical sensors on silicon substrates are disclosed in U.S. Pat. No. 5,200,051, which is hereby incorporated by reference in its entirety, and include, for example, dispensing methods, methods for attaching substrates and reagents to surfaces including photoformed layers, and methods for performing electrochemical assays.

Figure 6A:
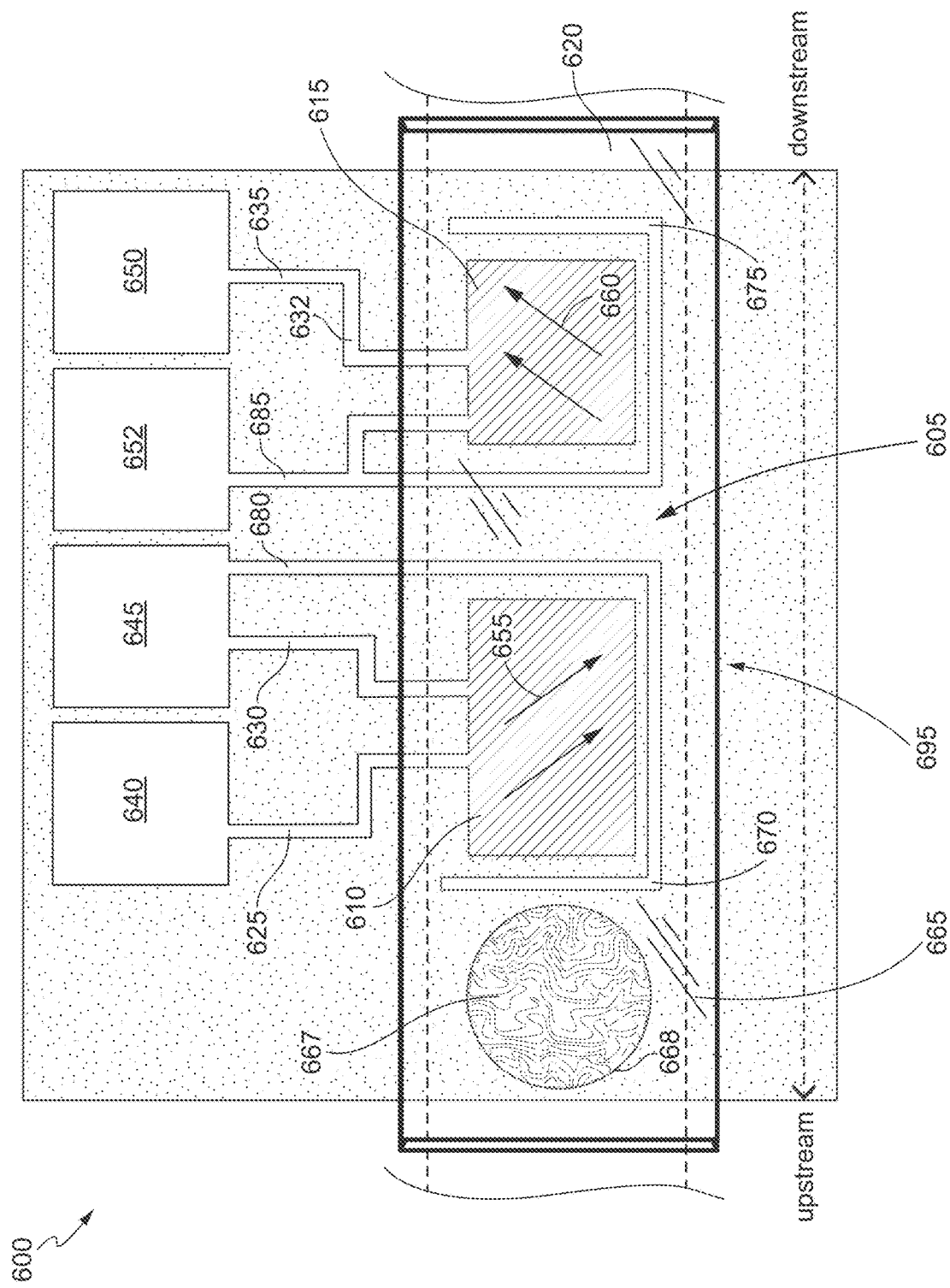
FIG. 6A shows a sensor chip configuration in accordance with various embodiments.

As shown in FIG. 6A, in some embodiments, a microfabricated sensor chip 600 includes sensor 605 (e.g., an optical sensor). The sensor 605 may be constructed of one or more light emitters 610 (e.g., LEDs) and one or more light detectors 615 (e.g., PDs) that are positioned in an area of the sensor chip 600 around a conduit 620. The sensor 605 may be connected via wirings 625, 630, 632, and 635 to a first conductive contact 640, a second conductive contact 645, a third conductive contact 650, and a fourth conductive contact 652 (e.g., temporary electrical connector), respectively. The design and arrangement of one or more light emitters 610, one or more light detectors 615, wirings 625, 630, 632, and 635, and/or conductive contacts 640, 645, 650, and 652 on the sensor chip 600 is preferably selected based on printing and performance characteristics (e.g., minimize interference between multiple sensors, maximize transmission of light through the conduit and biological specimen, avoidance of interfering light, size constraints, etc.). However, it should be understood to those of ordinary skill in the art that any design or arrangement for the components is contemplated without departing from the spirit and scope of the present invention.

In certain embodiments, the sensor 605 is configured to measure the absorption of radiation (i.e., light), as a function of frequency or wavelength, due to the interaction of the radiation with a biological sample in the conduit 620. In accordance with these aspects, the sensor 605 is constructed of the one or more light emitters 610 arranged to transmit incident light 655 of one or more wavelengths into the conduit 620 having the biological sample. Upon the incident light 655 striking the sample, photons that match an energy gap of a target analyte or a chromatic substance related to a presence of the target analyte present in the biological specimen are absorbed. Other photons transmit through the conduit 620 and biological specimen unaffected. The sensor 605 is further constructed of the one or more light detectors 615 arranged to collect the photons of light 660 transmitted through the conduit 620 and the biological sample, and convert the transmitted photons of light 660 into current. By comparing the attenuation of the transmitted light 660 with the incident light 655, an absorption spectrum can be obtained to identify the presence and/or concentration of the target analyte in the biological specimen.

The wirings 625, 630, 632, and 635 may be formed with gold surfaces that are optionally coated with a photo defined polyimide or photoresist layer such that the wirings 625, 630, 632, and 635 are insulated from exposure to the environment of the sensor region (e.g., the biological sample disposed within the conduit 620). The wirings 625, 630, 632, and 635 terminate at the first conductive contact 640, the second conductive contact 645, the fourth conductive contact 652, and the third conductive contact 650, respectively (e.g., the discrete connector contacts 150 as described with respect to FIG. 1), which are used to make electrical contact with a connector (e.g., the multi-terminal connector 155 as described with respect to FIG. 1) in the analyzer (e.g., an i-STAT® cartridge reader as described in U.S. Pat. No. 4,954,087, the entirety of which is incorporated herein by reference).

Figure 6B:
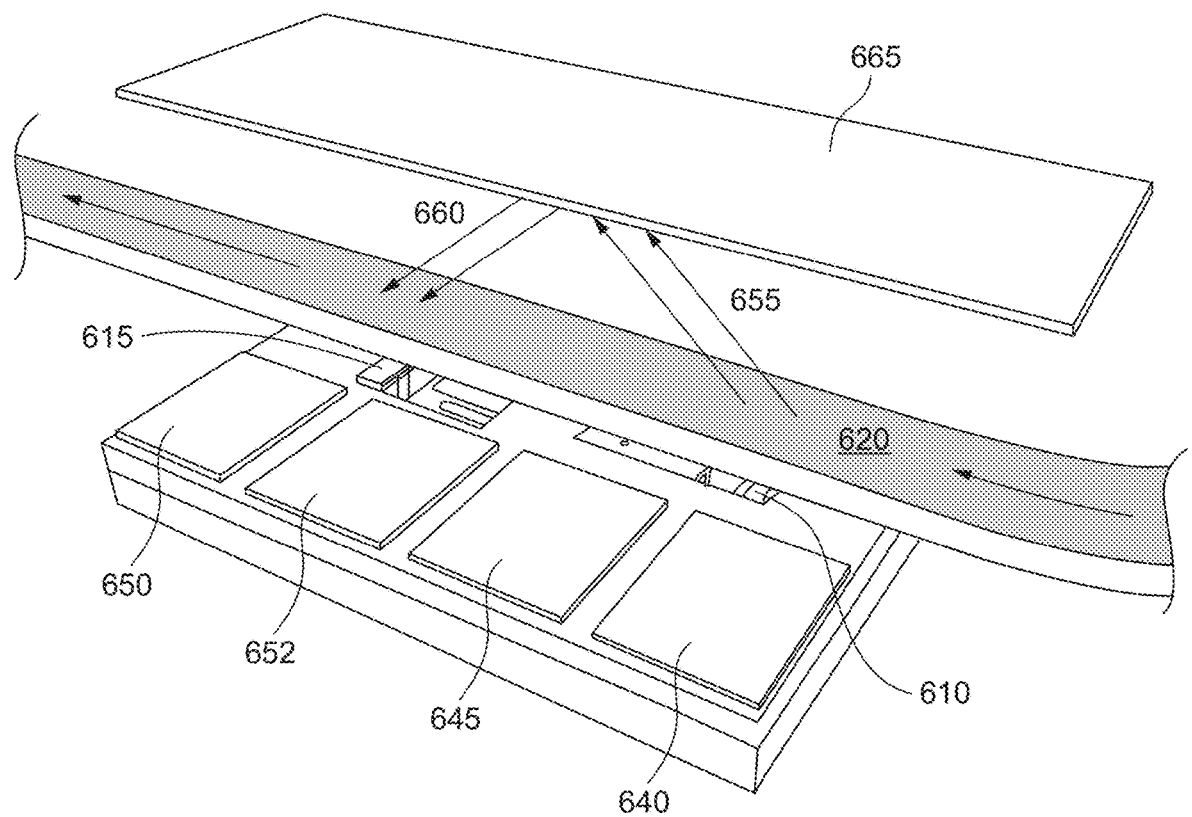
FIG. 6B shows a light shield or reflector in accordance with various embodiments.

As shown in FIGS. 6A and 6B, in some embodiments, a light shield or reflector 665 is provided over and/or around at least a portion of microfabricated sensor chip 600 to reflect the incident light 655 towards the one or more light detectors 615 and/or minimize or substantially block interfering environmental light (e.g., ambient t room light) from being detected by the one or more light detectors 615. In certain embodiments, the light shield or reflector 665 is positioned over and/or around the entirety of the microfabricated sensor chip 600. In other embodiments, the light shield or reflector 665 is positioned over and/or around the region of the sensor 605 and the conduit 620. In yet other embodiments, the light shield or reflector 665 is a surface of the conduit 620. In addition, the cartridge housing described with respect to FIGS. 4A-4J may be made of a black or opaque plastic material, wholly or in part, to minimize stray ambient light reaching the conduit 620 and striking the one or more light detectors 615. Moreover, it should be understood that inserting the cartridge 150 into the port 120 of the analyzer 110, as shown in FIG. 1, may also contribute to assuring that the sensor 605 (e.g., optical sensor) is shielded from stray ambient light.

In some embodiments, a portion of the sensor chip 600 (e.g., a top surface of the substrate), a wall of the conduit 620 (e.g., the conduit 431 described with respect to FIGS. 4A-4J), and/or a wall of the sample chamber (e.g., the sample holding chamber 410 described with respect to FIGS. 4A-4J) can be coated with one or more dry reagents to amend the biological sample. For example, the sensor chip 600 may include a reagent region 667 coated with a reactant and/or substrate for an analyte of interest.

One or more dry reagents that may be used to detect ALP are shown in Equation (1):

$$\text{p-nitrophenylphosphate} + H_2O \xrightarrow{ALP} \text{phosphate} + \text{p-nitrophenyl}; \quad (1)$$

One or more dry reagents that may be used to detect ALT are shown in Equations (2):

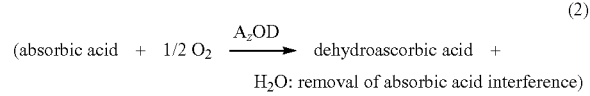
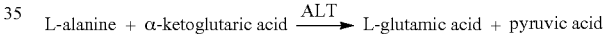
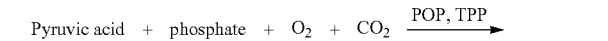
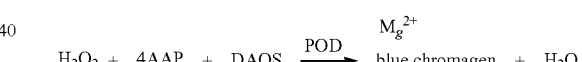
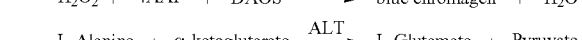
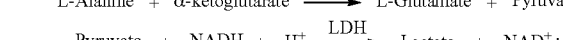

$$\text{(absorbic acid} + 1/2\, O_2 \xrightarrow{A_2OD} \text{dehydroascorbic acid} + H_2O: \text{removal of absorbic acid interference)}$$

$$\text{L-alanine} + \alpha\text{-ketoglutaric acid} \xrightarrow{ALT} \text{L-glutamic acid} + \text{pyruvic acid}$$

$$\text{Pyruvic acid} + \text{phosphate} + O_2 + CO_2 \xrightarrow{POP,\, TPP} \text{acetylphosphoric acid} + H_2O_2$$

$$H_2O_2 + 4AAP + DAOS \xrightarrow[]{\substack{Mg^{2+}\\POD}} \text{blue chromagen} + H_2O$$

$$\text{L-Alanine} + \alpha\text{-ketoglutarate} \xrightarrow{ALT} \text{L-Glutamate} + \text{Pyruvate}$$

$$\text{Pyruvate} + NADH + H^+ \xrightarrow{LDH} \text{Lactate} + NAD^+; \quad (2)$$

One or more dry reagents that may be used to detect AST are shown in Equations (3):

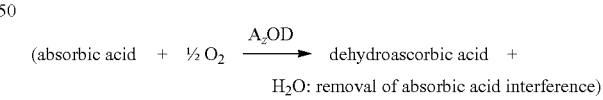
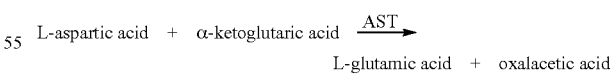
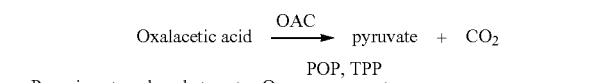
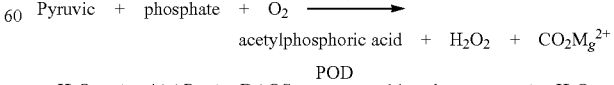
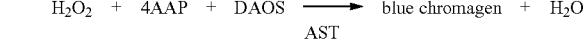

$$\text{(absorbic acid} + \tfrac{1}{2} O_2 \xrightarrow{A_2OD} \text{dehydroascorbic acid} + H_2O: \text{removal of absorbic acid interference)}$$

$$\text{L-aspartic acid} + \alpha\text{-ketoglutaric acid} \xrightarrow{AST} \text{L-glutamic acid} + \text{oxalacetic acid}$$

$$\text{Oxalacetic acid} \xrightarrow{OAC} \text{pyruvate} + CO_2$$

$$\text{Pyruvic} + \text{phosphate} + O_2 \xrightarrow{POP,\, TPP} \text{acetylphosphoric acid} + H_2O_2 + CO_2 Mg^{2+}$$

$$H_2O_2 + 4AAP + DAOS \xrightarrow{POD} \text{blue chromagen} + H_2O$$

$$\text{L-aspartate} + \alpha\text{-ketoglutarate} \xrightarrow{AST} \text{Oxaloacetate} + \text{L-glutamate}$$

-continued

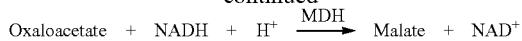

One or more dry reagents that may be used to detect bilirubin are shown in Equations (4):

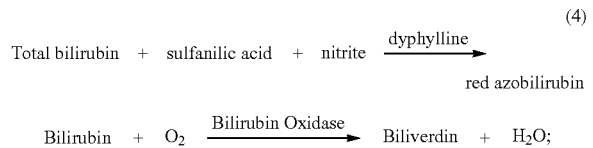

and
One or more dry reagents that may be used to detect total protein are shown in Equations (5):

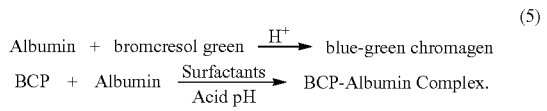

In various embodiments, the reagent region 667 may be defined by a containment ring structure 668. In some embodiments, the containment ring structure 668 is a hydrophobic ring of polyimide or another photolithographically produced layer. A microdroplet or several microdroplets (approximately 5-40 nL in size) or a series of about a 100 nanodroplets (approximately 50 to 1000 pL in size) containing the one or more dry reagents in some form may be dispensed or printed on the surface of the sensor chip 600. The photodefined ring structure 668 contains this aqueous droplet allowing the reagent region 667 to be localized to a precision of a few microns. The reagent region 667 can be made from 0.03 to approximately 2 mm² in size. The upper end of this size is limited by the size of the conduit and sensor chip 700 in present embodiments, and is not a limitation of the invention.

The biological sample or a fluid may be passed at least once over the dry reagent, e.g., the reagent region 667 to dissolve the reagent within the biological sample or fluid. Within a segment of the biological sample or fluid, the reagent can be preferentially dissolved and concentrated within a predetermined region of the segment. This is achieved through control of the position and movement of the segment. Thus, for example, if only a portion of a segment, such as the leading edge, is reciprocated over the reagent, then a high local concentration of the reagent can be achieved close to the leading edge. Alternatively, if a homogenous distribution of the reagent is desired, for example if a known concentration of a reagent is required for a quantitative analysis, then further reciprocation of the sample or fluid will result in mixing and an even distribution.

In certain embodiments, the universal channel circuitry of the analyzer applies a drive current (e.g., a voltage greater than 2V and a current less than 1 mA) via the first conductive contact 640 to the one or more light emitters 610 of the sensor 605, and measures output current from the one or more light emitters 610 via the second conductive contact 645. The output current is channeled from the second conductive contact 645 into the universal channel circuitry. Feedback resistor(s) of the universal channel circuitry set a nominal range of 0.5 mA to 4 mA, for example substantially 2 mA, which can provide over 1 mA at up to 4 V. The feedback resistor(s) are able to establish a constant current to continually drive the one or more light emitters 610 via the first conductive contact 640 for a predetermined period of time. The one or more light detectors 615 channel output current (i.e., the current converted from the photons of light 660 received from the one or more light emitters 610) to the third conductive contact 650. The fourth contact 652 provides a return path. The output current is channeled from the third conductive contact 650 into the universal channel circuitry and converted to a measurable voltage proportional to the amount of light detected by the one or more light detectors 615. The processor (e.g., the processor 220 described with respect to FIG. 2) converts the measurable voltage to a qualitative, semi-quantitative, or quantitative value proportional to an amount of target analyte in the biological specimen.

In various embodiments, the sensor chip 600 may further include a conductometric sensor (e.g., hematocrit sensors). The conductometric sensor is configured to determine biological sample arrival and/or departure at the sensor 605. More specifically, the conductometric sensor lies perpendicular to a length of the conduit 620, and an electrical resistance between pairs of electrodes for the conductometric sensor may be used to monitor a relative position of a fluid front of the biological sample. For example, at the extremes, an open circuit reading may indicate that the biological sample has been pushed off sensor 605 and a closed circuit reading may indicate the sensor 605 is covered with the biological sample.

As shown in FIG. 6A, the conductometric sensor may comprise at least two electrodes 670 and 675 (i.e., electrode pair) positioned downstream and upstream of the one or more light emitters 610 and one or more light detectors 615, respectively. The electrodes 670 and 675 may be connected via wirings 680 and 685 to a first conductive contact such as the second conductive contact 645, which may function as a conductometric low pin, and a second conductive contact such as the fourth conductive contact 652, which may function as an alternating current source or conductometric high pin, respectively. The wirings 680 and 685 may be formed with a gold surface that is coated with a photo defined polyimide or photoresist layer such that the wirings 680 and 685 are insulated from exposure to the biological sample disposed within the conduits. As such, in some embodiments, the biological sample or fluid reaches a sensing region 695 after passing over the electrode 670, then the biological sample subsequently departs the sensing region 695 after passing over the electrode 675.

Figure 7A:
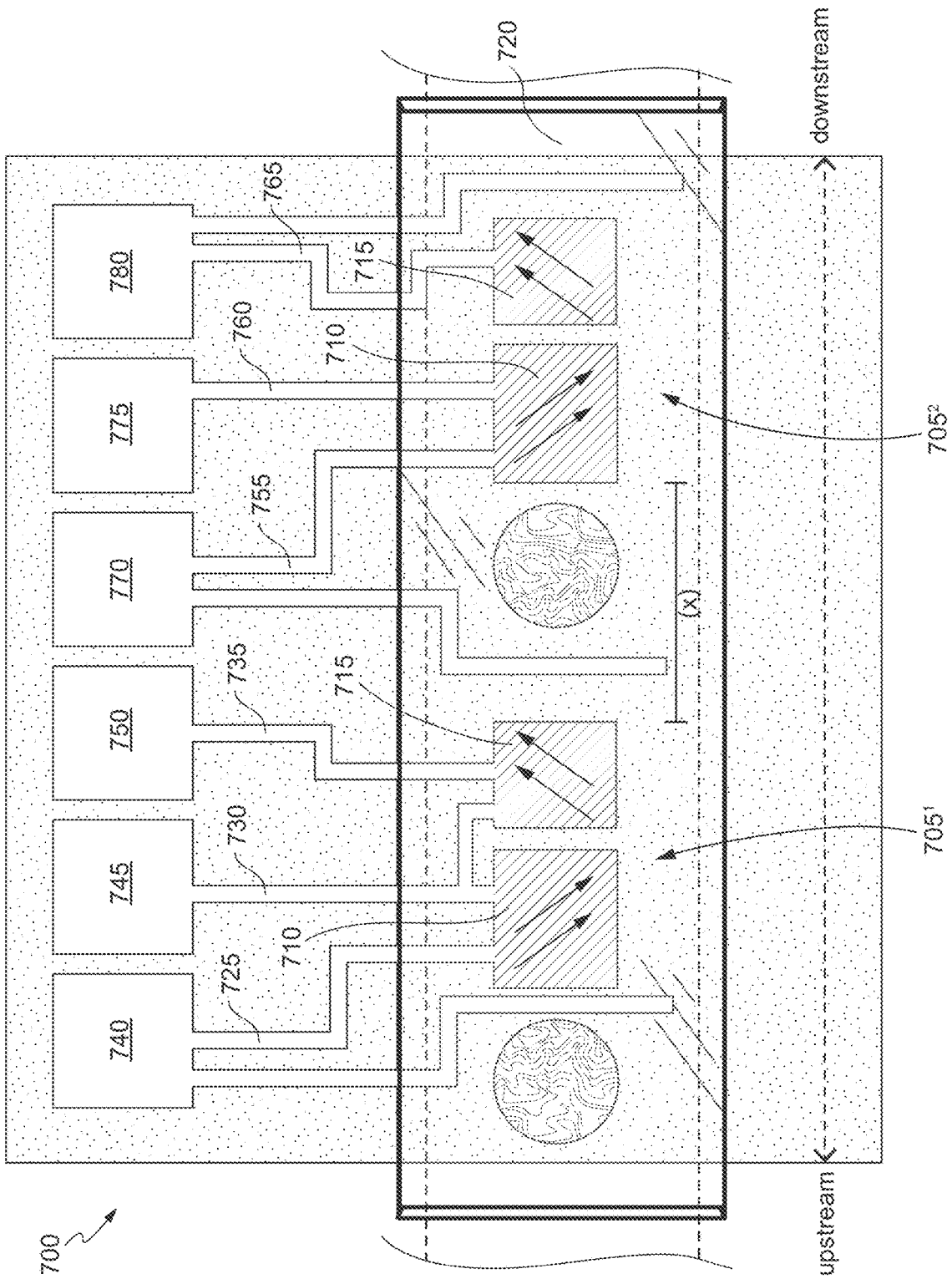
FIGS. 7A and 7B show an alternative sensor chip configuration in accordance with various embodiments.
Figure 7B:
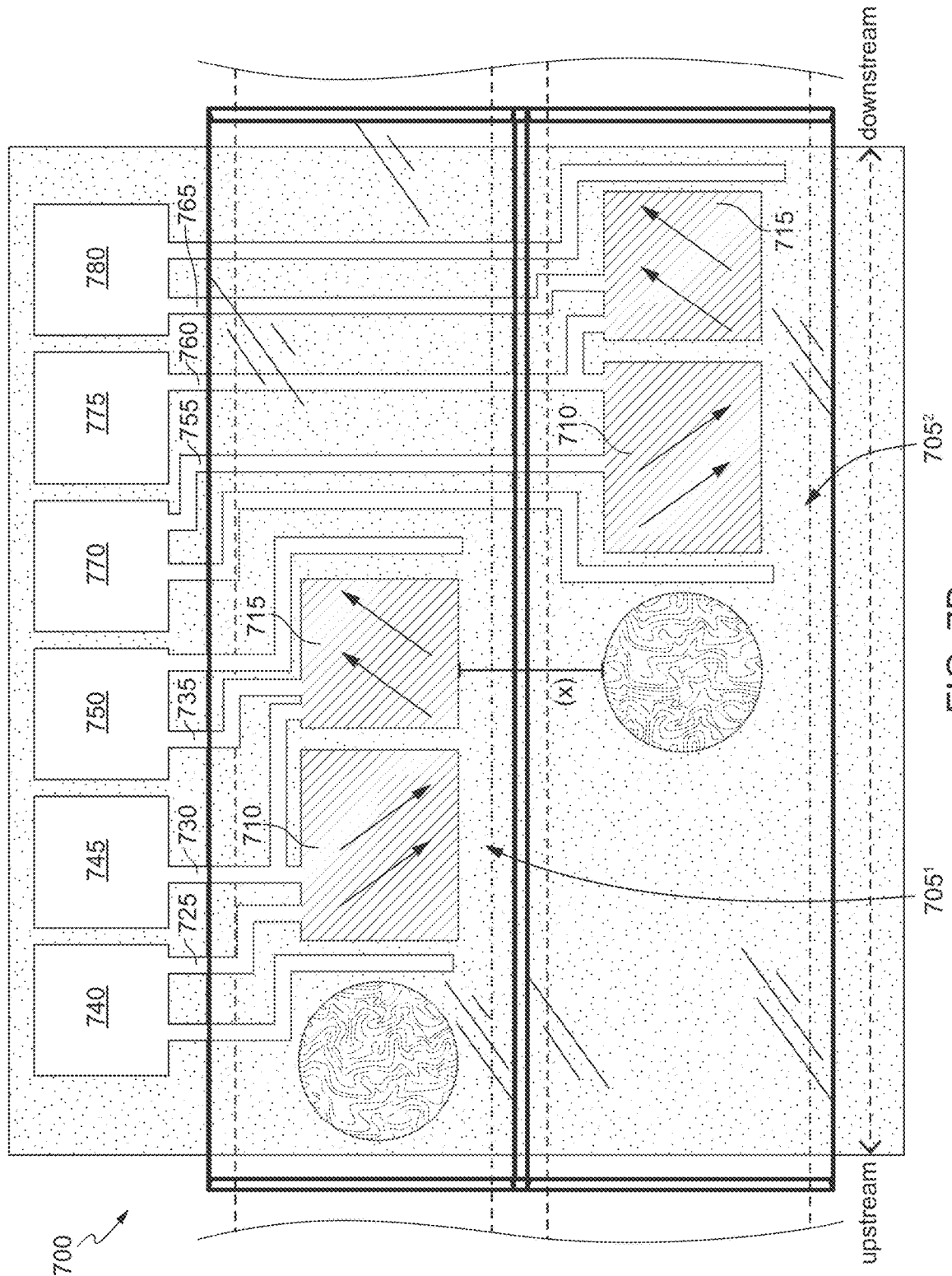

As shown in FIGS. 7A and 7B, in alternative embodiments, a microfabricated sensor chip 700 includes a plurality of optical sensors $705^1$, $705^2$, ... $705^N$. Each sensor 705 may be constructed of one or more light emitters 710 (e.g., LEDs) and one or more light detectors 715 (e.g., PDs). As shown in FIG. 7A, in some embodiments, the plurality of plurality of optical sensors $705^1$, $705^2$, ... $705^N$ may be fabricated as adjacent structures in an area of the sensor chip 700 near (e.g., below, above, or adjacent) a conduit 720. However, in order for each sensor 705 to accurately detect a qualitative, semi-quantitative, or quantitative value proportional to an amount of target analyte in the biological specimen, it may be beneficial in certain embodiments to position each sensor 705 in optically distinct regions. For example, a first sensor $705^1$ may generate light of a first wavelength using one or more light emitters $710^1$ that is detected by one or more light detectors $715^1$, and a second sensor $705^2$ may generate light of a second wavelength (same or different from the first wavelength) using one or more light emitters $710^2$ that is detected by one or more light detectors $715^2$. In order to ensure that the incident light and the transmitted light from the first sensor $705^1$ do not interfere with the second sensor $705^2$, and vice versa, the first sensor $705^1$ and the second sensor $705^2$ may be spaced apart from one another into optically distinct regions by a predetermined distance. In certain embodiments, the first sensor $705^1$ and the second sensor $705^2$ are spaced apart from one another by a predetermined distance "x", which is at least 0.3 mm, preferably at least 0.6 mm.

As shown in FIG. 7B, in other embodiments, the plurality of optical sensors $705^1$, $705^2$, . . . $705^N$ may be fabricated in separate areas of the sensor chip 700 near (e.g., below, above, or adjacent) respective conduits 720. However, in order for each sensor 705 to accurately detect a qualitative, semi-quantitative, or quantitative value proportional to an amount of target analyte in the biological specimen, it may be beneficial in certain embodiments to position each sensor 705 in optically distinct regions. For example, a first sensor $705^1$ positioned near (e.g., below, above, or adjacent) a first conduit $720^1$ may generate light of a first wavelength using one or more light emitters $710^1$ that is detected by one or more light detectors $715^1$, and a second sensor $705^2$ near (e.g., below, above, or adjacent) a second conduit $720^2$ may generate light of a second wavelength (same or different from the first wavelength) using one or more light emitters $710^2$ that is detected by one or more light detectors $715^2$. In order to ensure that the incident light and the transmitted light from the first sensor $705^1$ do not interfere with the second sensor $705^2$, and vice versa, the first sensor $705^1$ and the second sensor $705^2$ may be spaced apart from one another into optically distinct regions by a predetermined distance. In certain embodiments, the first sensor $705^1$ and the second sensor $705^2$ are spaced apart from one another by a predetermined distance "x", which is at least 0.5 mm, preferably at least 0.9 mm.

In certain embodiments, the first sensor $705^1$ may be connected via wirings 725, 730, and 735 to a first conductive contact 740, a second conductive contact 745, and a third conductive contact 750 (e.g., temporary electrical connector), respectively. Additionally, the second sensor $705^2$ may be connected via wirings 755, 760, and 765 to a first conductive contact 770, a second conductive contact 775, and a third conductive contact 780 (e.g., temporary electrical connector), respectively. The design and arrangement of the first sensor $705^1$, the second sensor $705^2$, the wirings 725, 730, 735, 755, 760, and 765, and/or conductive contacts 740, 745, 750, 770, 775, and 780 on the sensor chip 700 is preferably selected based on printing and performance characteristics (e.g., minimize interference between multiple sensors, maximize transmission of light through the conduit and biological specimen, avoidance of interfering light, size constraints, etc.). However, it should be understood to those of ordinary skill in the art that any design or arrangement for the sensors is contemplated without departing from the spirit and scope of the present invention. Furthermore, although it is shown in FIGS. 7A and 7B that the second sensor $705^2$ is placed downstream from the first sensor $705^1$, it should be understood that alternative embodiments of the present invention are contemplated, for example, having the second sensor $705^2$ placed upstream from the first sensor $705^1$.

For the sake of brevity, the additional structures and processes described with respect sensor chip 600 in FIGS. 6A and 6B are not repeated here. However, it should be understood to those of ordinary skill in the art that the additional structures and processes may be included with respect to sensor chip 700, and any design or arrangement for the additional structures and processes is contemplated without departing from the spirit and scope of the present invention.

Figure 8A:
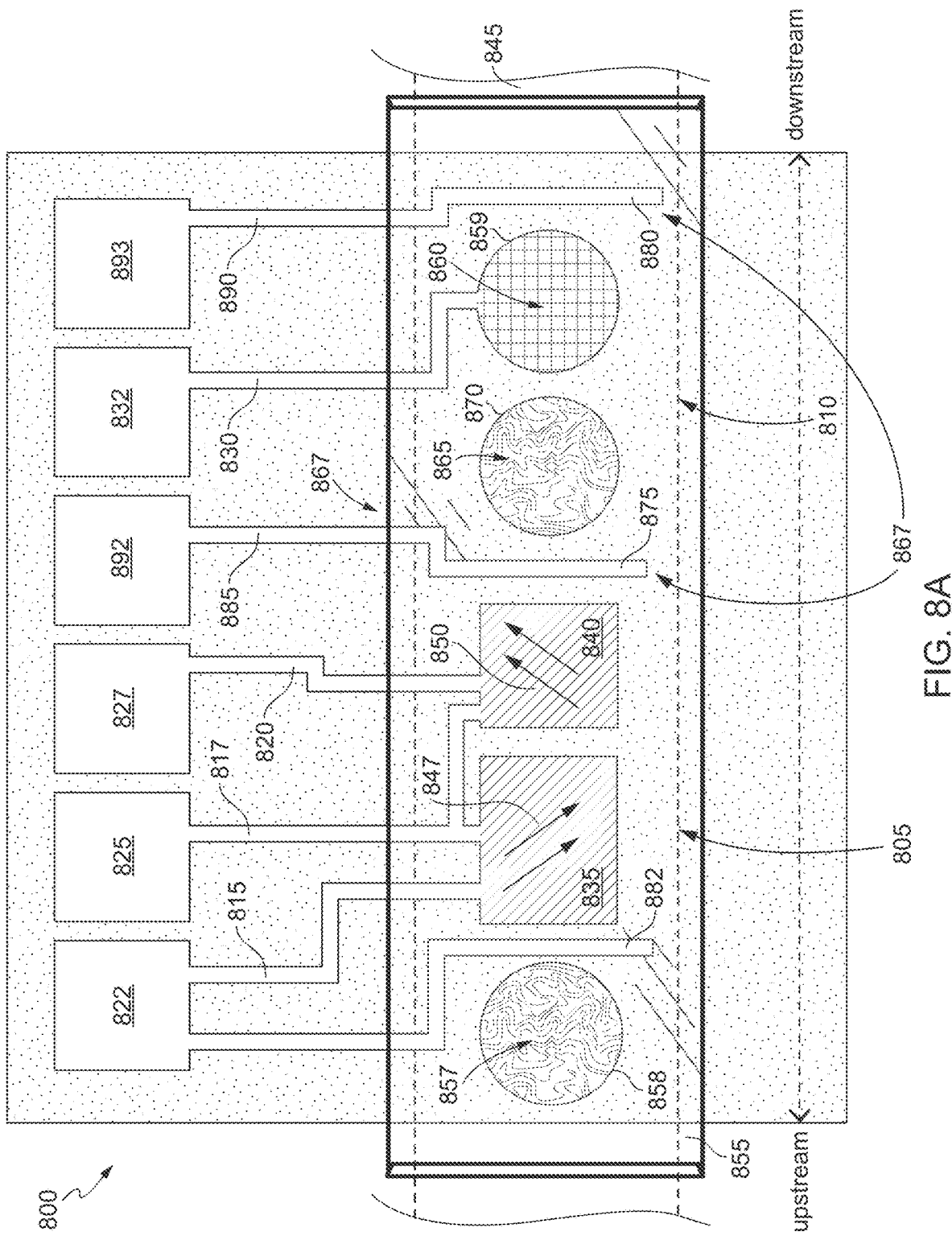
FIGS. 8A and 8B show an alternative sensor chip configuration in accordance with various embodiments.
Figure 8B:
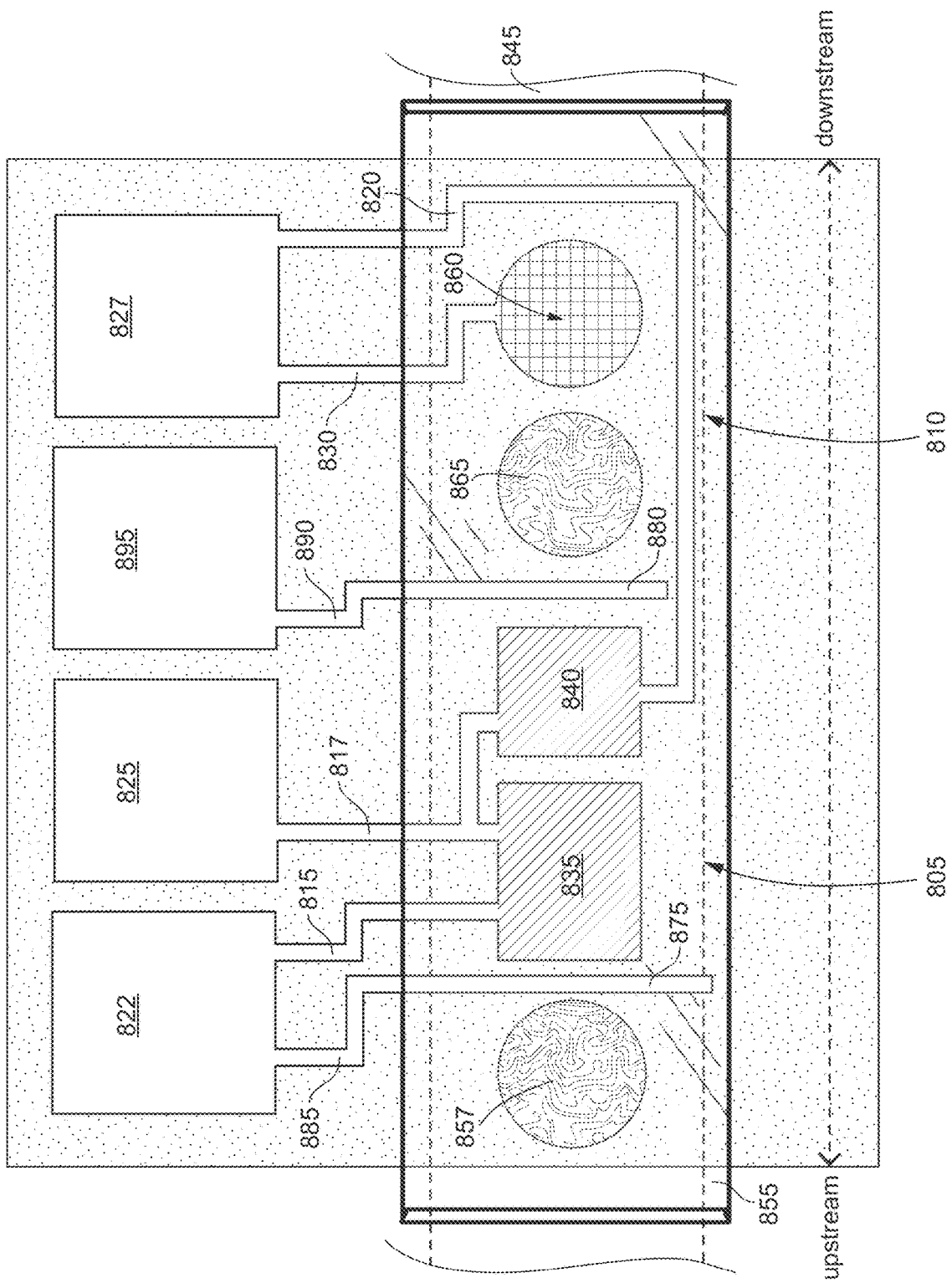

As shown in FIGS. 8A and 8B, in alternative embodiments, a microfabricated sensor chip 800 includes a first sensor 805 (e.g., an optical sensor) and optionally a second sensor 810 (e.g., an amperometric sensor). The first sensor 805 may be constructed with one or more light emitters (e.g., LEDs) and one or more light detectors (e.g., PDs) in a first area of the sensor chip 800, as similarly described with respect to FIG. 6A. The second sensor 810 may be constructed with an array of metal disks or electrodes that cover a region in a second area of the sensor chip 800. The first sensor 805 and the second 810 may be fabricated as adjacent structures, respectively, on sensor chip 800. However, in order for the sensor chip 800 to accurately detect a qualitative, semi-quantitative, or quantitative value proportional to an amount of target analyte in the biological specimen, the first sensor 805 and the second sensor 810 may be spaced apart from one another at a predetermined distance "x". For example, the first sensor 805 may be spaced at least 0.3 mm, preferably at least 0.6 mm from the second sensor 810.

As shown in FIG. 8A, in some embodiments, the first sensor 805 may be connected via wirings 815, 817, and 820 to a first conductive contact 822, a second conductive contact 825, and a third conductive contact 827 (e.g., temporary electrical connector), respectively, and the second sensor 810 may be connected via wiring 830 to a fourth conductive contact 832 (e.g., temporary electrical connector). In some embodiments, the first sensor 805 may be configured as an optical sensor and the second sensor 810 may be configured as electrochemical sensor both of which are formed on the single sensor chip 800 and positioned near or within one or more conduits of the point of care test cartridge. Although it is shown in FIG. 8A that the second sensor 810 is placed downstream from the first sensor 805, it should be understood that alternative embodiments of the present invention contemplate other arrangements such as having the second sensor 810 placed upstream from the first sensor 805.

As shown in FIG. 8B, in other embodiments, the first sensor 805 may be connected via wirings 815, 817, and 820 to a first conductive contact 822, a second conductive contact 825, and a third conductive contact 827 (e.g., temporary electrical connector), respectively, and the second sensor 810 may be connected via wiring 830 to the third conductive contact 827 (e.g., temporary electrical connector). In some embodiments, the first sensor 805 may be configured as an optical sensor and the second sensor 810 may be configured as electrochemical sensor both of which are formed on the single sensor chip 800 and positioned near or within one or more conduits of the point of care test cartridge. Although it is shown in FIG. 8B that the second sensor 810 is placed downstream from the first sensor 805, it should be understood that alternative embodiments of the present invention contemplate having the second sensor 810 placed upstream from the first sensor 805.

The first sensor 805 may be constructed of one or more light emitters 835 (e.g., LEDs) and one or more light detectors 840 (e.g., PDs) that are positioned in a first area of the sensor chip 800 and the second sensor 810 may be constructed with an array of metal disks or electrodes that cover a circular region in a second area of the sensor chip 800. The design and arrangement of the first and second sensors 805 and 810 on the sensor chip 800 are preferably selected based on printing and performance characteristics for each of the first and second sensors 805 and 810. However, it should be understood to those of ordinary skill in the art that any design or arrangement for the sensors is contemplated without departing from the spirit and scope of the present invention. Furthermore, although the first and second sensors 805 and 810 in the example in FIGS. 8A and 8B are described herein as optical and amperometric sensors, other sensors can be used. For example, a potentiometric sensor may be used for the detection of ionic species such as Na+ or K+.

In various embodiments, the first sensor 805 is an optical sensor positioned around a conduit 845. The first sensor 805 may be configured to measure the absorption of radiation (i.e., light), as a function of frequency or wavelength, due to the interaction of the radiation with a biological sample in the conduit 845. In accordance with these aspects, the first sensor 805 may be constructed of the one or more light emitters 835 arranged to transmit incident light 847 of one or more wavelengths into the conduit 845 having the biological sample. Upon the incident light 847 striking the sample, photons that match an energy gap of a target analyte or a chromatic substance related to a presence of the target analyte present in the biological specimen are absorbed. Other photons transmit through the conduit 845 and biological specimen unaffected. The first sensor 805 may be further constructed of the one or more light detectors 845 that are arranged to collect the photons of light 850 transmitted through the conduit 845 and the biological sample, and convert the transmitted photons into current. By comparing the attenuation of the transmitted light 850 with the incident light 847, an absorption spectrum can be obtained to identify the presence and/or concentration of the target analyte in the biological specimen.

The wirings 815, 817, and 820 may be formed with gold surfaces that are optionally coated with a photo defined polyimide or photoresist layer such that the wirings 815, 817, and 820 are insulated from exposure to the environment of the sensor region (e.g., the biological sample disposed within the conduit 845). The wirings 815, 817, and 820 terminate at the first conductive contact 822, the second conductive contact 825, and the third conductive contact 827, respectively (e.g., the discrete connector contacts 150 as described with respect to FIG. 1), which are used to make electrical contact with a connector (e.g., the multi-terminal connector 155 as described with respect to FIG. 1) in the analyzer (e.g., an i-STAT® cartridge reader as described in U.S. Pat. No. 4,954,087, the entirety of which is incorporated herein by reference).

In some embodiments, a light shield or reflector 855 may be provided over and/or around at least a portion of microfabricated sensor chip 800 to reflect the incident light 847 towards the one or more light detectors 840 and/or minimize or substantially block interfering environmental light (e.g., ambient t room light) from being detected by the one or more light detectors 840. In certain embodiments, the light shield or reflector 855 is positioned over and/or around the entirety of the microfabricated sensor chip 800. In other embodiments, the light shield or reflector 855 is positioned over and/or around the region of the first sensor 805 and the conduit 845. In addition, the cartridge housing described with respect to FIGS. 4A-4J may be made of a black or opaque plastic material, wholly or in part, to minimize stray ambient light reaching the conduit and striking the one or more light detectors 840. Moreover, it should be understood that inserting the cartridge 150 into the port 120 of the analyzer 110, as shown in FIG. 1, may also contribute to assuring that the first sensor 805 (e.g., optical sensor) is shielded from stray ambient light.

In some embodiments, a portion of the sensor chip 800 (e.g., a top surface of the substrate), a wall of the conduit 845 (e.g., the conduit 431 described with respect to FIGS. 4A-4J), and/or a wall of the sample chamber (e.g., the sample holding chamber 410 described with respect to FIGS. 4A-4J) can be coated with one or more dry reagents to amend the biological sample for an optical assay. For example, the sensor chip 800 may include a reagent region 857 coated with a reactant and/or substrate for an analyte of interest. The one or more dry reagents suitable for optical assays for total protein, AST, ALT, ALP, and bilirubin are described with respect to FIG. 6A.

In various embodiments, the reagent region 857 may be defined by a containment ring structure 858. In some embodiments, the containment ring structure 858 is a hydrophobic ring of polyimide or another photolithographically produced layer. A microdroplet or several microdroplets (approximately 5-40 nL in size) or a series of about a 100 nanodroplets (approximately 50 to 1000 pL in size) containing the one or more dry reagents in some form may be dispensed or printed on the surface of the sensor chip 800. The photodefined ring structure 858 contains this aqueous droplet allowing the reagent region 857 to be localized to a precision of a few microns. The reagent region 857 can be made from 0.03 to approximately 2 mm$^2$ in size. The upper end of this size is limited by the size of the conduit and sensor chip 800 in present embodiments, and is not a limitation of the invention.

In certain embodiments, the universal channel circuitry of the analyzer applies a drive current (e.g., a voltage greater than 2V and a current less than 1 mA) via the first conductive contact 822 to the one or more light emitters 835 of the sensor 805, and measures output current from the one or more light emitters 835 via the second conductive contact 825. The output current is channeled from the second conductive contact 825 into the universal channel circuitry. Feedback resistor(s) of the universal channel circuitry set a nominal range of 0.5 mA to 4 mA, for example substantially 2 mA, which can provide over 1 mA at up to 4 V. The feedback resistor(s) are able to establish a constant current to continually drive the one or more light emitters 835 via the first conductive contact 822 for a predetermined period of time. The one or more light detectors 840 channel output current (i.e., the current converted from the photons of light 850 received from the one or more light emitters 835) to the third conductive contact 827. The output current is channeled from the third conductive contact 827 into the universal channel circuitry and converted to a measurable voltage proportional to the amount of light detected by the one or more light detectors 840. The processor converts the measurable voltage to a qualitative, semi-quantitative, or quantitative value proportional to an amount of target analyte in the biological specimen.

The second sensor 810 may be formed as electrodes with gold surfaces that are exposed (e.g., no polyimide or photoresist covering) to the inside environment of the conduit 845 and configured to directly contact the biological sample disposed within the conduit 845. The wiring 830 may be formed with a gold surface that is coated with a photo defined polyimide or photoresist layer such that the wiring 830 is insulated from exposure to the biological sample disposed within the conduit 845. The wiring 830 may be formed comprising a containment ring structure 859. In some embodiments, the containment ring structure 859 may be configured to contain capture antibodies immobilized on or near the surface of the electrodes. For example, the capture antibodies may be deposited onto at least a portion of the second sensor 810 within the containment ring structure 859. As shown with respect to FIG. 8A, the wiring 830 terminates at the third conductive contact 827 (e.g., one of the discrete connector contacts 150 as described with respect to FIG. 1), which is used to make electrical contact with the connector (e.g., the multi-terminal connector 155 as described with respect to FIG. 1) in the analyzer. Alternatively, as shown with respect to FIG. 8B, the wiring 830 terminates at the fourth conductive contact 832 (e.g., one of the discrete connector contacts 150 as described with respect to FIG. 1), which is used to make electrical contact with the connector (e.g., the multi-terminal connector 155 as described with respect to FIG. 1) in the analyzer.

In various embodiments, the second sensor 810 is an immunosensor positioned in the conduit 845 for receiving a biological sample mixed with an antibody-enzyme conjugate that is configured to bind to a target analyte within the biological sample. The second sensor 810 may be configured to detect an enzymatically produced electroactive species (e.g., 4-aminophenol) from the reaction of a substrate (e.g., 4-aminophenylphosphate) with the antibody-enzyme conjugate (e.g., one or more antibodies bound to alkaline phosphatase (ALP)). In accordance with these aspects, the second sensor 810 contains a capture region or regions 860 coated with capture antibodies that are configured to bind to a target analyte bound to an antibody-enzyme conjugate. The capture region 860 may be defined by the containment ring structure 859. In some embodiments, the containment ring structure 859 is a hydrophobic ring of polyimide or another photolithographically produced layer. A microdroplet or several microdroplets (approximately 5-40 nL in size) containing capture antibodies in some form, for example bound to beads or microspheres, may be dispensed on the surface of the second sensor 810. The photodefined ring structure 859 contains this aqueous droplet allowing the capture region 860 to be localized to a precision of a few microns. The capture region 860 can be made from 0.03 to approximately 2 $mm^2$ in size. The upper end of this size is limited by the size of the conduit 845 and sensor chip 800 in present embodiments, and is not a limitation of the invention.

In some embodiments, a portion of the sensor chip 800 (e.g., a top surface of the substrate), a wall of the conduit 845 (e.g., the conduit 431 described with respect to FIGS. 4A-4J), and/or a wall of the sample chamber (e.g., the sample holding chamber 410 described with respect to FIGS. 4A-4J) can be coated with one or more dry reagents to amend the biological sample for an electrochemical assay. For example, the sensor chip 800 may include a reagent region 865 coated with an antibody-enzyme conjugate for an analyte of interest. The reagent region 865 may be defined by a containment ring structure 870. In some embodiments, the containment ring structure 870 is a hydrophobic ring of polyimide or another photolithographically produced layer. A microdroplet or several microdroplets (approximately 5-40 nL in size) or a series of about a 100 nanodroplets (approximately 50 to 1000 pL in size) containing the antibody-enzyme conjugate in some form may be dispensed or printed on the surface of the sensor chip 800. The photodefined ring structure 870 contains this aqueous droplet allowing the reagent region 865 to be localized to a precision of a few microns. The reagent region 865 can be made from 0.03 to approximately 2 $mm^2$ in size. The upper end of this size is limited by the size of the conduit and sensor chip 800 in present embodiments, and is not a limitation of the invention.

The biological sample or a fluid may be passed at least once over the dry reagent, e.g., the reagent region 865 to dissolve the reagent within the biological sample or fluid. Reagents used to amend biological samples or fluid within the cartridge may include the antibody-enzyme conjugate, magnetic beads coated with capture antibodies, or blocking agents that prevent either specific or non-specific binding reactions among assay compounds. Within a segment of the biological sample or fluid, the reagent can be preferentially dissolved and concentrated within a predetermined region of the segment. This is achieved through control of the position and movement of the segment. Thus, for example, if only a portion of a segment, such as the leading edge, is reciprocated over the reagent, then a high local concentration of the reagent can be achieved close to the leading edge. Alternatively, if a homogenous distribution of the reagent is desired, for example if a known concentration of a reagent is required for a quantitative analysis, then further reciprocation of the sample or fluid will result in mixing and an even distribution.

In certain embodiments, the universal channel circuitry of the analyzer applies a potential via the fourth conductive contact 832 (FIG. 8A) or the third conductive contact 827 (FIG. 8B) or to the second sensor 810 and a reference electrode, and measures current changes generated by oxidation current from the substrate as an electrochemical signal. The electrochemical signal being proportional to the concentration of the analyte in the biological sample. The second sensor 810 may have an applied potential of approximately +0 mV to 90 mV, e.g., 60 mV versus the reference electrode and, in another preferred embodiment, the second sensor 810 has an applied potential of approximately +40 mV versus the reference electrode. The signal generated by the enzyme reaction product at approximately +10 mV is distinguishable from the signal generated by the unreacted substrate at approximately +200 mV. It should be noted that the exact voltages used to amperometrically detect the substrate and the analyte will vary depending on the chemical structure of the substrate. It is important that the difference in the voltages used to detect the substrate be great enough to prevent interference between the readings.

In various embodiments, the sensor chip 800 may further include one or more conductometric sensors 867 (e.g., hematocrit sensors). The one or more conductometric sensors 867 are configured to determine biological sample arrival and/or departure at the reagent regions 857 and 865 and biological sample arrival and/or departure at the first and second sensors 805 and 810. More specifically, the one or more conductometric sensors 867 lie perpendicular to a length of the conduit 845 or sensor conduit, and an electrical resistance between pairs of electrodes for the sensor may be used to monitor a relative position of a fluid front of the biological sample. For example, at the extremes, an open circuit reading may indicate that the biological sample has been pushed off the reagent region 857 or 865 and a closed circuit reading may indicate the reagent region 857 or 865 is covered with the biological sample.

As shown in FIGS. 8A and 8B, the one or more conductometric sensors 867 may comprise at least two electrodes 875 and 880 (i.e., electrode pair) (optionally a third electrode 882 as shown in FIG. 8A). The electrode 875 may be positioned downstream of the first sensor 805 and upstream from the reagent region 865, and the electrode 880 may be position downstream of the reagent region 865 and upstream of the second sensor 810. As shown in FIG. 8A, the electrodes 875 and 880 may be connected via wirings 885 and 890 to a fifth conductive contact 892, which functions as a conductometric low pin, and a sixth conductive contact 893, which functions an alternating current source or conductometric high pin, respectively. Alternatively, as shown in FIG. 8B, the electrodes 875 and 880 may be connected via wirings 885 and 890 to the first conductive contact 822, which function as a conductometric low pin, and a fourth conductive contact 895, which functions as an alternating current source or conductometric high pin, respectively. The wirings 885 and 890 may be formed with a gold surface that is coated with a photo defined polyimide or photoresist layer such that the wirings 885 and 890 are insulated from exposure to the biological sample disposed within the conduits. As such, in some embodiments, the biological sample or fluid reaches the reagent region 865 after departing the first sensor 805 and passing over the electrode 875, then the biological sample subsequently arrives at the second sensor 810 after departing the reagent region 865 and passing over the electrode 880.

Figure 9A:
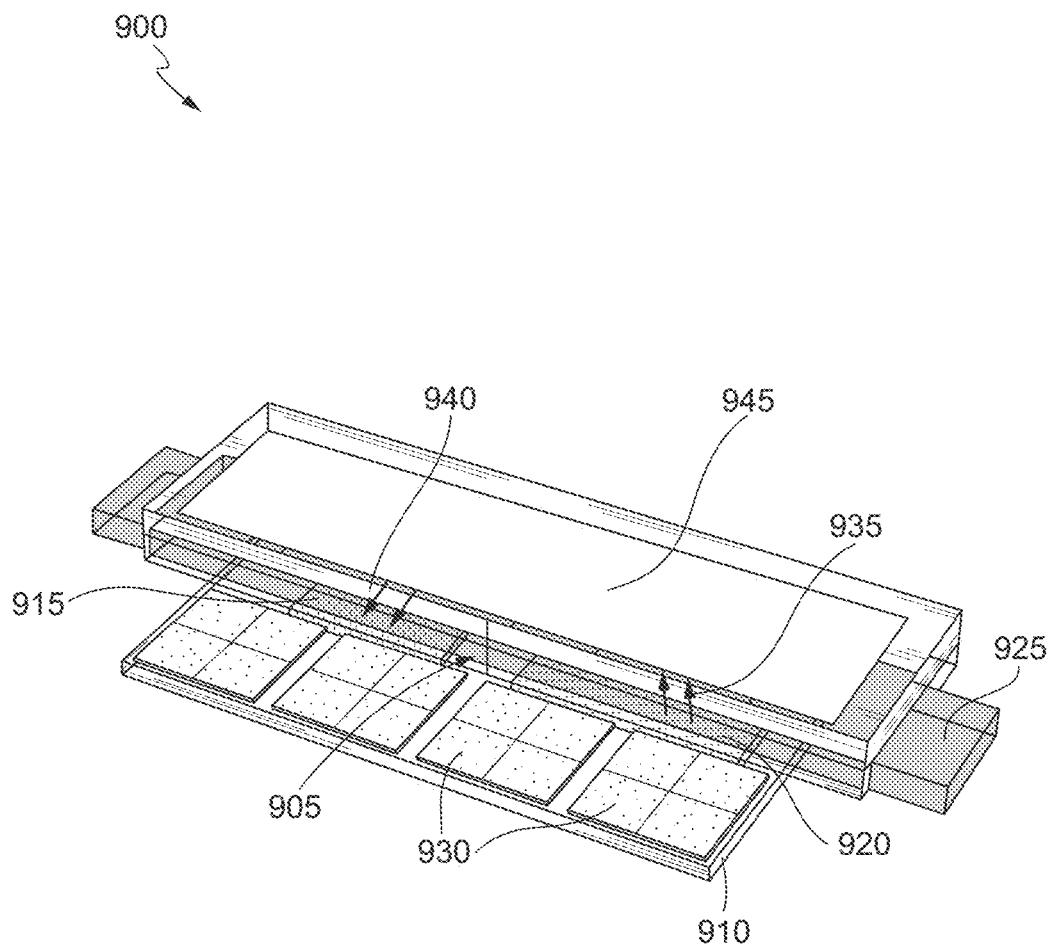
FIGS. 9A and 9B show a transparent substrate in accordance with various embodiments.
Figure 9B:
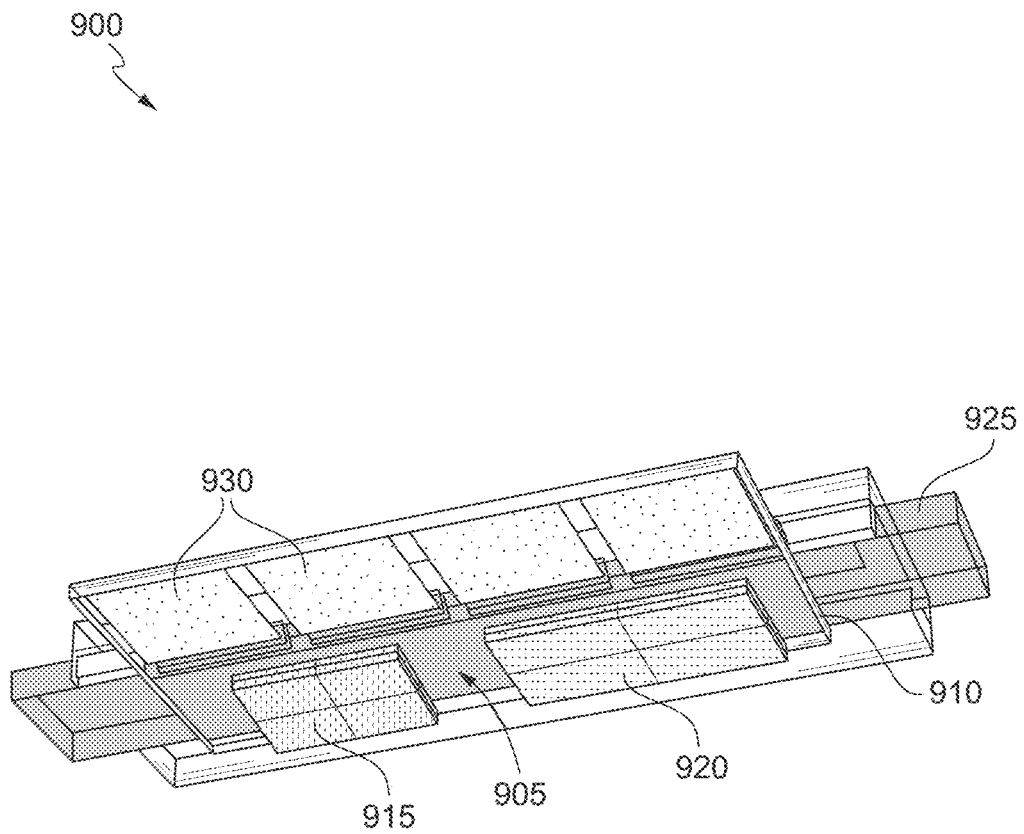

As shown in FIGS. 9A and 9B, in some embodiments, a microfabricated sensor chip 900 includes sensor 905 (e.g., an optical sensor) disposed below the substrate 910 (e.g., substrate 500 described with respect to FIG. 5B). The sensor 905 may be constructed of one or more light emitters 915 (e.g., LEDs) and one or more light detectors 920 (e.g., PDs) that are positioned in an area of the sensor chip 900 below a conduit 925. The sensor 905 may be connected via wirings to conductive contacts 930. In order for the incident light 935 generated by the one or more light emitters 915 to be transmitted into the conduit 925 having the biological sample, the substrate 910 may be formed of a transparent material, e.g., a transparent plastic or polyester substrate such as polydimethylsiloxane (PDMS), a liquid transparent silicone polymer. Upon the incident light 935 striking the sample, photons that match an energy gap of a target analyte or a chromatic substance related to a presence of the target analyte present in the biological specimen are absorbed. Other photons of light 940 transmit through the conduit 925 and biological specimen unaffected and are reflected back to the one or more detectors 920 via a light shield or reflector 945. The one or more light detectors 920 are arranged to collect the photons of light 940 transmitted through the conduit 925, the biological sample, and the substrate 910. The one or more detectors 920 converts the transmitted photons of light 940 into current.

While some embodiments are disclosed herein with respect to certain types of sensors (e.g., optical, electrochemical, and conductometric sensors) being electrically connected to certain pins, this is not intended to be restrictive. Instead, it should be understood to those of ordinary skill in the art that any design or arrangement for the sensors and pins is contemplated without departing from the spirit and scope of the present invention. For example, the universal channel circuitry is configured in such a manner that any pin and connector connection can be used as a channel for optical, amperometric, conductometric, and/or potentiometric measurements, as discussed in detail herein.

Universal Channel Circuitry

Figure 10A:
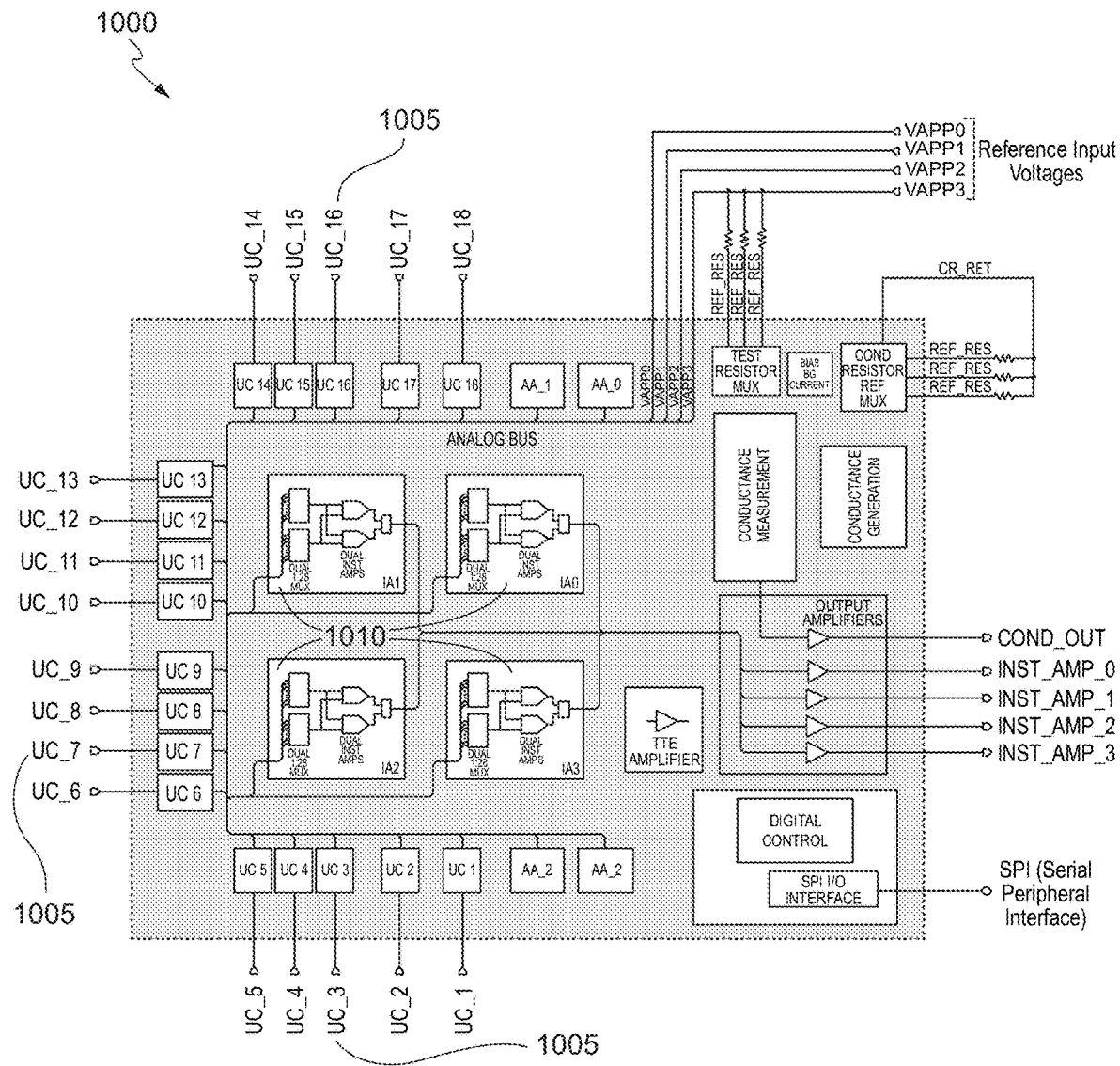
FIGS. 10A-10G show universal channel circuitry in accordance with various embodiments.

In various embodiments, the computing device (e.g., computing device 205 described with respect to FIG. 2 as being resident on a network infrastructure or within the environment of the analyzer) includes universal channel circuitry. The universal channel circuitry includes electronic switching capabilities such that any contact pin, and thus any sensor contact pad in a testing device, can be connected to one or more measurement channels (e.g., potentiometric, amperometric, conductometric, etc.). As shown in FIG. 10A, the universal channel circuitry 1000 may comprise any number n of channels 1005 (e.g., 18 channels) that can be applied to any one of a number m of contact pins on the multi-terminal connector. The channels 1005 can be applied to the contact pins in combination, activated, and/or deactivated as so desired.

Figure 10B:
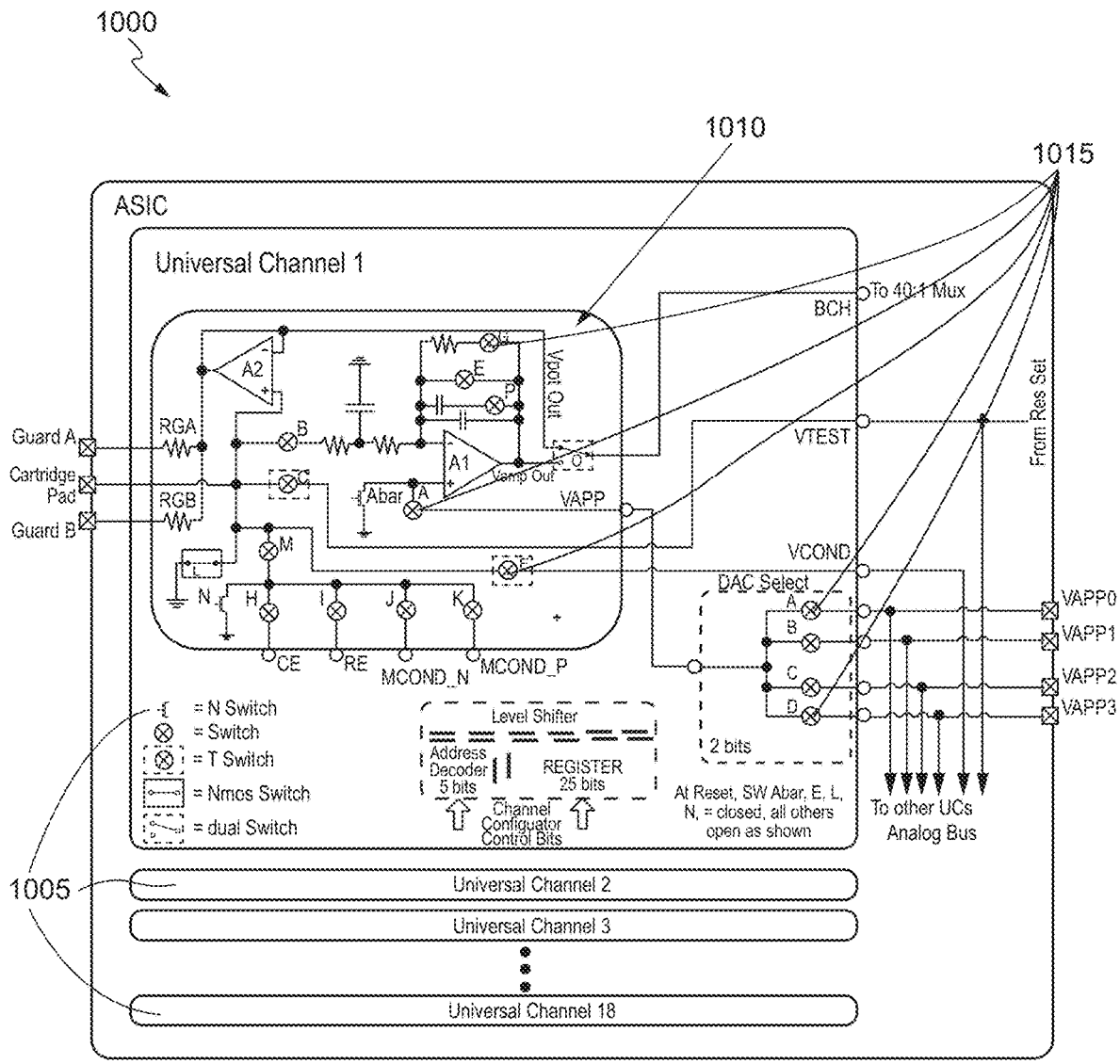
Figure 10C:
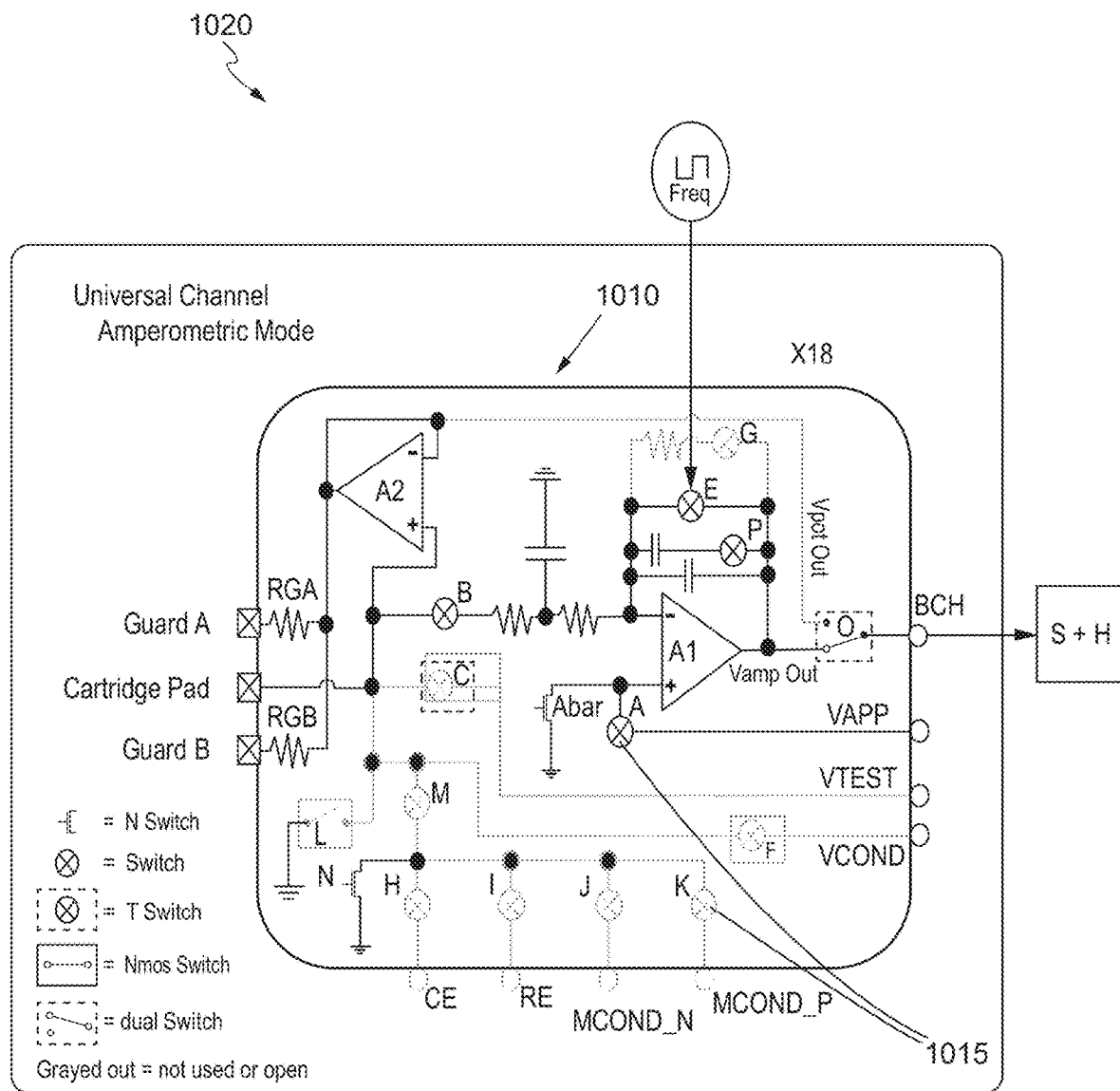
Figure 10D:
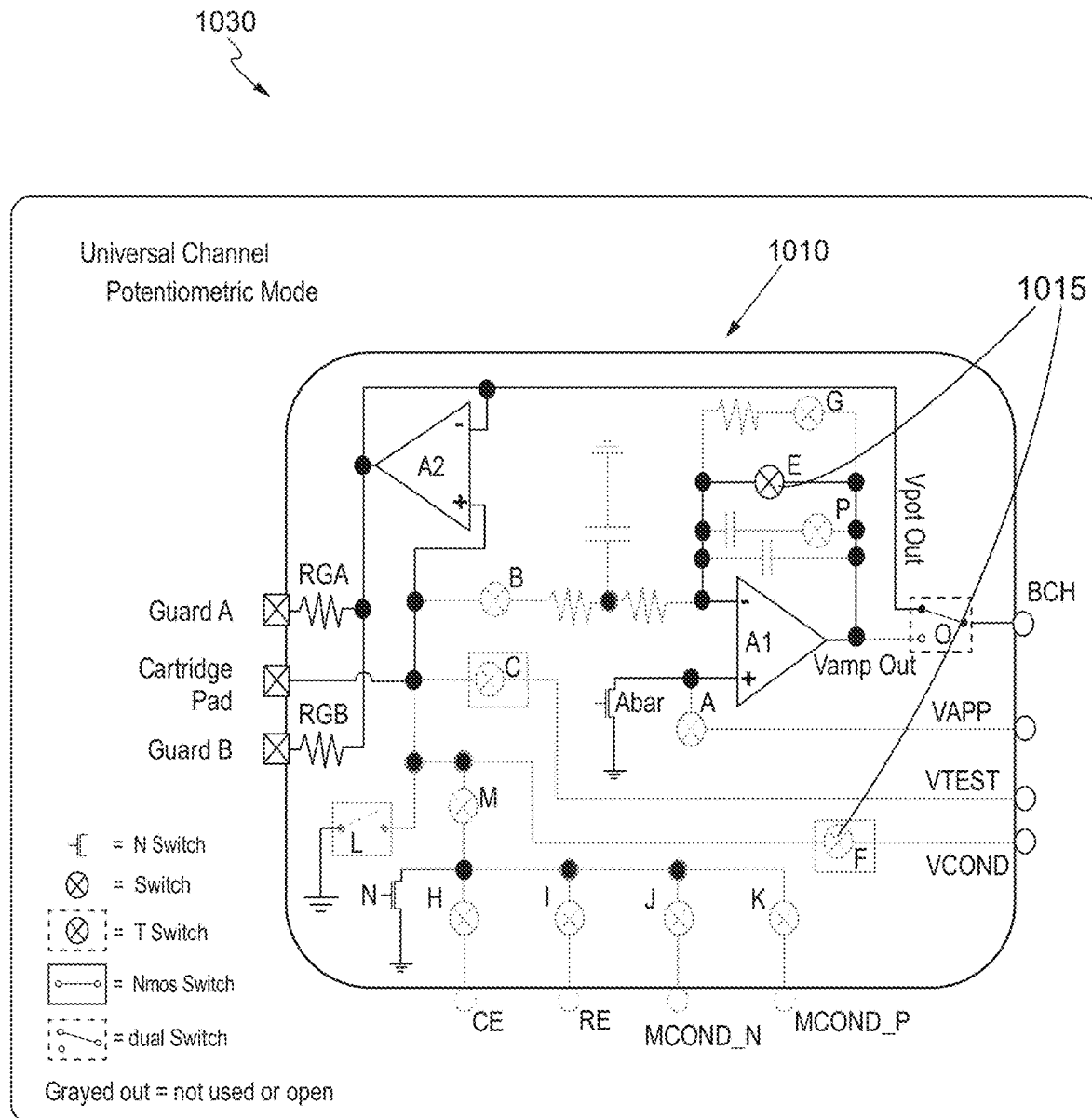

As further shown in FIGS. 10A and 10B, each channel 1005 includes circuitry 1010 that can be switched between various modes or configuration using the one or more switches 1015 and computer readable program instructions, data structures, program modules and/or other data stored within the memory (e.g., storage device 225 as described with respect to FIG. 2) of the analyzer. For example, any channel 1005 is capable of being potentiometric, amperometric, conductometric, ground etc., and in some embodiments all channels are defaulted to ground upon power-up or reset of the analyzer. In some embodiments, any channel is capable of being an amperometric channel having circuitry 1010 switched into a amperometric measurement mode as configuration 1020 (the grayed out circuitry being circuitry not used or switched off in the amperometric measurement mode), as shown in FIG. 10C. As should be understood, the amperometric measurement mode and an optical sensor current measurement mode use the same channel configuration 1020 in order to perform both amperometric assays and optical assays. Moreover, any channel is capable of being a potentiometric channel, and in some embodiments the circuitry 1010 is switched into a potentiometric measurement mode or configuration 1030 (the grayed out circuitry being circuitry not used or switched off in the potentiometric measurement mode), as shown in FIG. 10D. In these modes or configurations, the channels 1005 are primarily configured to measure currents and voltages provided by optical, amperometric, and potentiometric sensors.

Figure 10E:
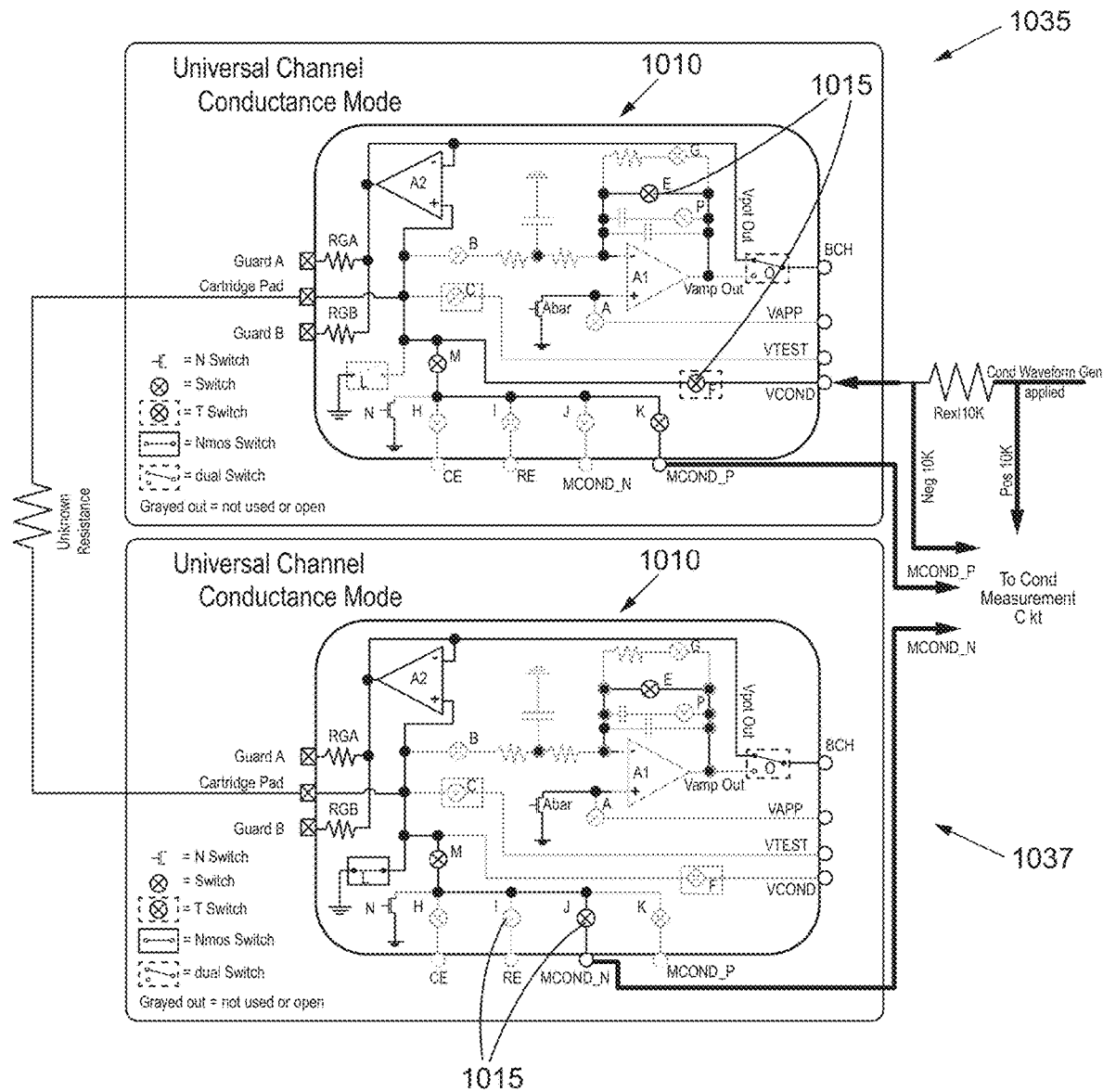

In accordance with various aspects of the present invention, the universal channel circuitry 1000 is configured to provide conductometric measurements between at least two channels. For example, any channel 1005 (A) may be assigned to a conductometric high electrode of a testing device via a first pair of pins and contacts and any other channel 1005 (B) may be assigned to a conductometric low electrode of a testing device via a second pair of pins and contacts. The circuitry 1010 of channel 1005 (A) may be switched into a high conductometric measurement mode or configuration 1035, and the circuitry 1010 of channel 1005 (B) may be switched into a low conductometric measurement mode or configuration 1037 (the grayed out circuitry being circuitry not used or switched off in the low and high conductometric measurement modes or configurations), respectively as shown in FIG. 10E. The high and low conductometric measurement modes or configurations 1035 and 1037 can be enabled or disabled from channels 1005 (A) and (B) at any time after power-up such as upon insertion and identification of a type of testing device inserted into the analyzer, or relocated to other channels as necessary. In some embodiments, the conductance functionality is designed using a synchronous detection method that is advantageously less sensitive to parasitic capacitance. For example, the alternating current stimulus may be generated from a well-controlled constant alternating current circuit that ensures high linearity with load.

Figure 10F:
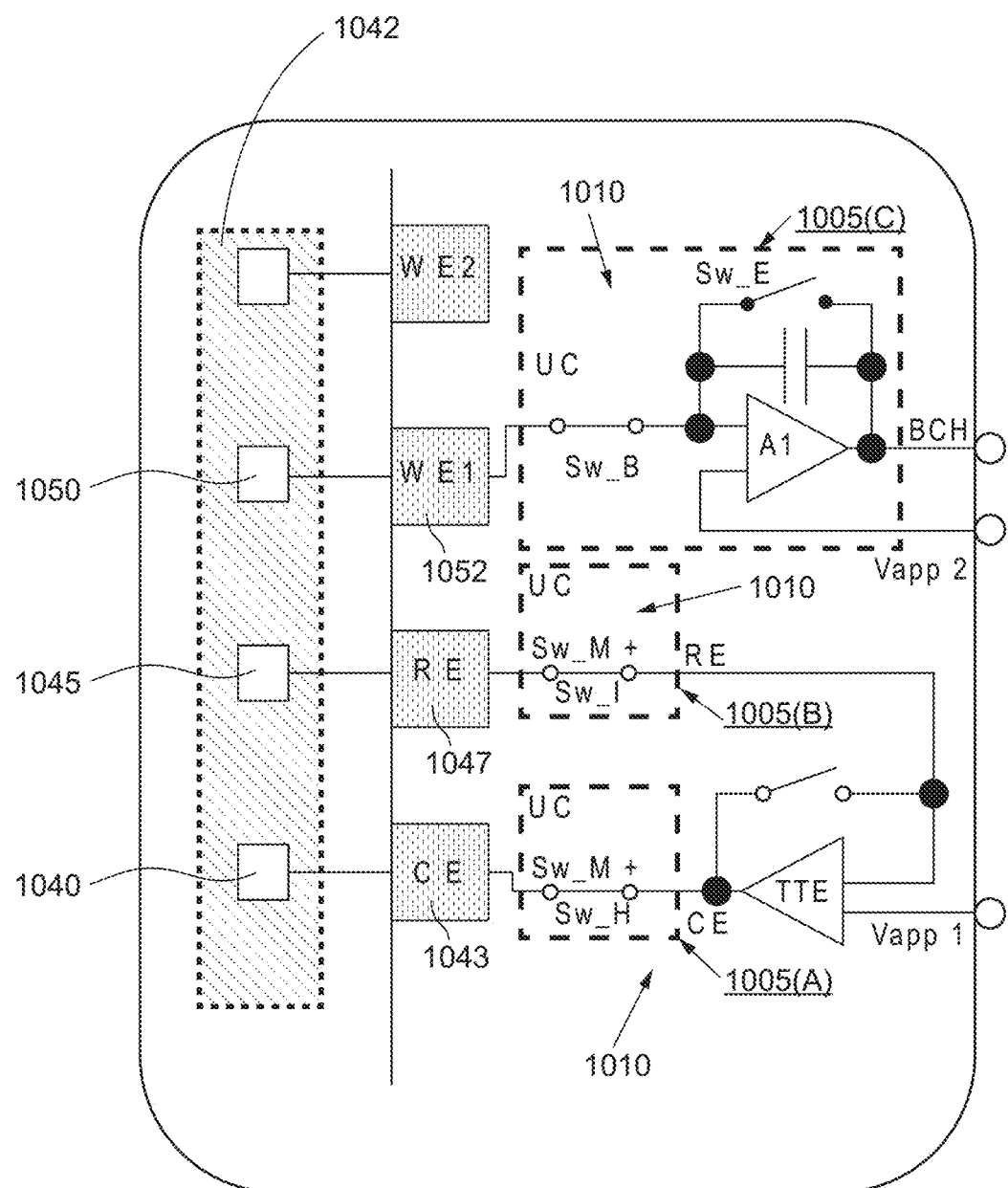

In accordance with other aspects of the present invention, the universal channel circuitry 1000 is configured to provide multiple electrode (e.g., three electrode) or sensor capability. For example, any channel 1005 (A) may be assigned to a counter electrode 1040 of a testing device 1042 via a first pair of pins and contacts 1043, any other channel 1005 (B) may be assigned to a reference electrode 1045 of the testing device 1042 via second pair of pins and contacts 1047, and any other channel 1005(C) may be assigned to a working electrode 1050 of the testing device 1042 via a third pair of pins and contacts 1052, as shown in FIG. 10F. The circuitry 1010 of channel 1005 (A) may be switched into counter measurement mode by enabling Sw_M and Sw_H and other switches disabled, the circuitry 1010 of channel 1005 (B) may be switched into reference measurement mode by enabling Sw_M and Sw_I and other switches disabled, and the circuitry 1010 of channel 1005 (C) may be switched into amperometric measurement mode or configuration 1020. The counter measurement mode, the reference measurement mode, and the amperometric measurement mode or configuration 1020 can be enabled or disabled from channels 1005 (A), (B) and (C) at any time after power-up such as upon insertion and identification of a type of testing device inserted into the analyzer, or relocated to other channels as necessary.

Figure 10G:
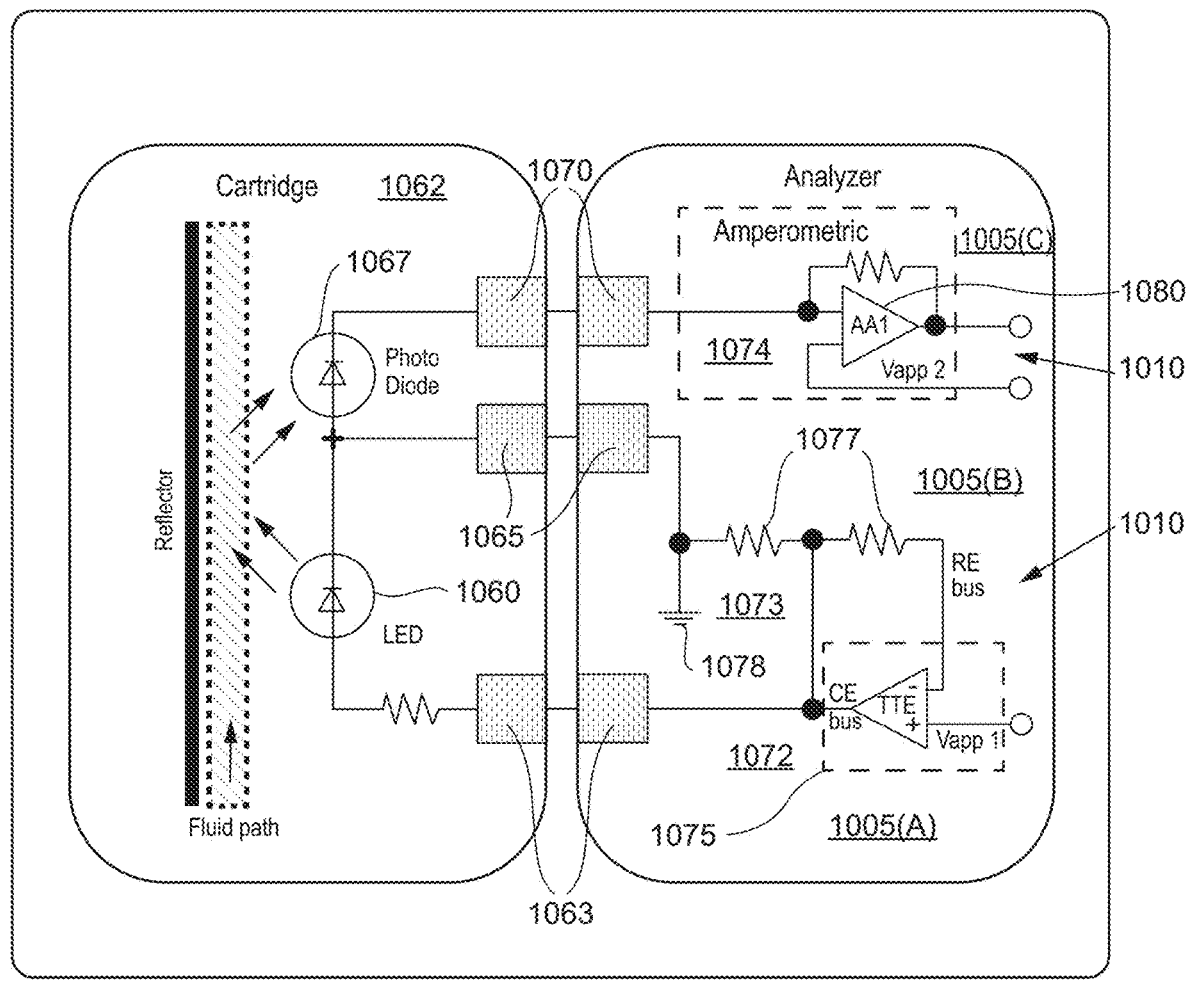

In accordance with other aspects of the present invention, the universal channel circuitry 1000 is configured to provide for optical sensor capability (e.g., as describe with reference to FIG. 6A). For example, as shown in FIG. 10G, any channel 1005 (A) may be assigned to one or more light emitters 1060 of a testing device 1062 via a first pair of pins and contacts 1063, any other channel 1005 (B) may be assigned to the to one or more light emitters 1060 and/or one or more light detectors 1067 of the testing device 1062 via a second pair of pins and contacts 1065, and any other channel 1005 (C) may be assigned to the one or more light detectors 1067 of the testing device 1062 via a third pair of pins and contacts 1070. The circuitry 1010 of channel 1005 (A) may be switched into a current driver mode or configuration 1072, the circuitry 1010 of channel 1005 (B) may be switched into a feedback mode and/or a ground mode or configuration 1073, and the circuitry 1010 of channel 1005 (C) may be switched into a current measurement mode or configuration 1074. In some embodiments, the circuitry 1010 of channel 1005 (A) comprises a first amplifier 1075 connected to one or more contacts of the one or more light emitters 1060, the circuitry 1010 of channel 1005 (B) comprises one or more feedback resistors 1077 connected to one or more contacts of the one or more light emitters 1060 and/or a ground 1078 connected to one or more contacts of the one or more light emitters 1060 and/or one or more light detectors 1067, and the circuitry 1010 of channel 1005 (C) comprises a second amplifier 1080 connected to one or more contacts of the one or more light detectors 1067. The current driver measurement mode or configuration 1072, the feedback mode and/or a ground mode or configuration 1073, and the current measurement mode or configuration 1074, can be enabled or disabled from channels 1005 (A), (B), and (C) at any time after power-up such as upon insertion and identification of a type of testing device inserted into the analyzer, or relocated to other channels as necessary.

In accordance with yet other aspects of the present invention, the universal channel circuitry is configured to provide multiple electrode or sensor capability (e.g., optical, electrochemical, and conductometric sensors, as described with reference to FIGS. 8A and 8B). For example, any channel (A) may be assigned to one or more light emitters of a testing device via a first pair of pins and contacts and a second pair of pins and contacts, any other channel 1005 (B) may be assigned to the to one or more light emitters and/or one or more light detectors of the testing device via a second pair of pins and contacts, and any other channel (C) may be assigned to one or more light detectors of the testing device via a third pair of pins and contacts, as similarly described with reference to FIG. 10G. Additionally, any other channel (D) may be assigned to a counter electrode of the testing device via a fourth pair of pins and contacts, any other channel (E) may be assigned to a reference electrode of the testing device via fifth pair of pins and contacts, and channel (C) (optionally any other channel (F)) may be assigned to a working electrode of the testing device via the third pair of pins and contacts (optionally another pair of pins and contacts), as similarly described with reference to FIG. 10F. Moreover, any channel (G) may be assigned to a conductometric low electrode of the testing device via the second pair of pins and contacts (optionally another pair of pins and contacts) and any other channel (H) may be assigned to a conductometric high electrode of a testing device via a sixth pair of pins and contacts, as similarly described with reference to FIG. 10E.

The circuitry of channel (A) may be switched into a current driver mode or configuration, the circuitry of channel (B) may be switched into a feedback mode and/or a ground mode or configuration, the circuitry of channel (C)/(F) may be switched into a current measurement mode or configuration, the circuitry of channel (D) may be switched into counter measurement mode or configuration, the circuitry of channel (E) may be switched into reference measurement mode or configuration, the circuitry of channel (G) may be switched into a low conductometric measurement mode or configuration, and the circuitry of channel (H) may be switched into a high conductometric measurement mode or configuration. The various measurement modes or configurations can be enabled or disabled from the various channels at any time after power-up such as upon insertion and identification of a type of testing device inserted into the analyzer, or relocated to other channels as necessary.

While the universal channel circuitry has been described at some length and with some particularity with respect to a specific design and/or performance need, it is not intended that the universal channel circuitry be limited to any such particular design and/or performance need. Instead, it should be understood the universal channel circuitry configurations described herein are exemplary embodiments, and that the universal channel circuitry configurations are to be construed with the broadest sense to include variations of the specific design and/or performance need described herein, as well as other variations that are not described with particularity herein. In particular, the channels, the modes or configurations, the pairs of pins and contacts, the electrodes, and the sensors discussed in the various systems and devices may be combined, connected, adjusted or modified to meet specific design and/or performance needs. Furthermore, it is to be understood that other structures illustrated in the figures may have been omitted from the description of the universal channel circuitry for clarity. The omitted structures may include, for example, logic gates, resistors, amplifiers, etc., and such omitted structures and their layout in the circuit diagrams are incorporated herein in their entireties for all purposes.

Combined Immunoassay Methods

FIGS. 11-16 show exemplary flowcharts for performing the process steps of the present invention. The steps of FIGS. 11-16 may be implemented using the computing devices and systems described above with respect to FIGS. 1-10G. Specifically, the flowcharts in FIGS. 11-16 illustrate the architecture, functionality, and operation of possible implementations of the systems, methods and computer program products according to several embodiments of the present invention. In this regard, each block in the flowcharts may represent a module, segment, or portion of code, which comprises one or more executable instructions stored on non-transitory machine readable storage medium that when executed by one or more processors (e.g., a processor of the analyzer) cause the one or more processors to perform the specified logical function(s) within the one or more executable instructions. It should also be noted that, in some alternative implementations, the functions noted in the blocks may occur out of the order noted in the figure. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts, or combinations of special purpose hardware and computer instructions.

Figure 11:
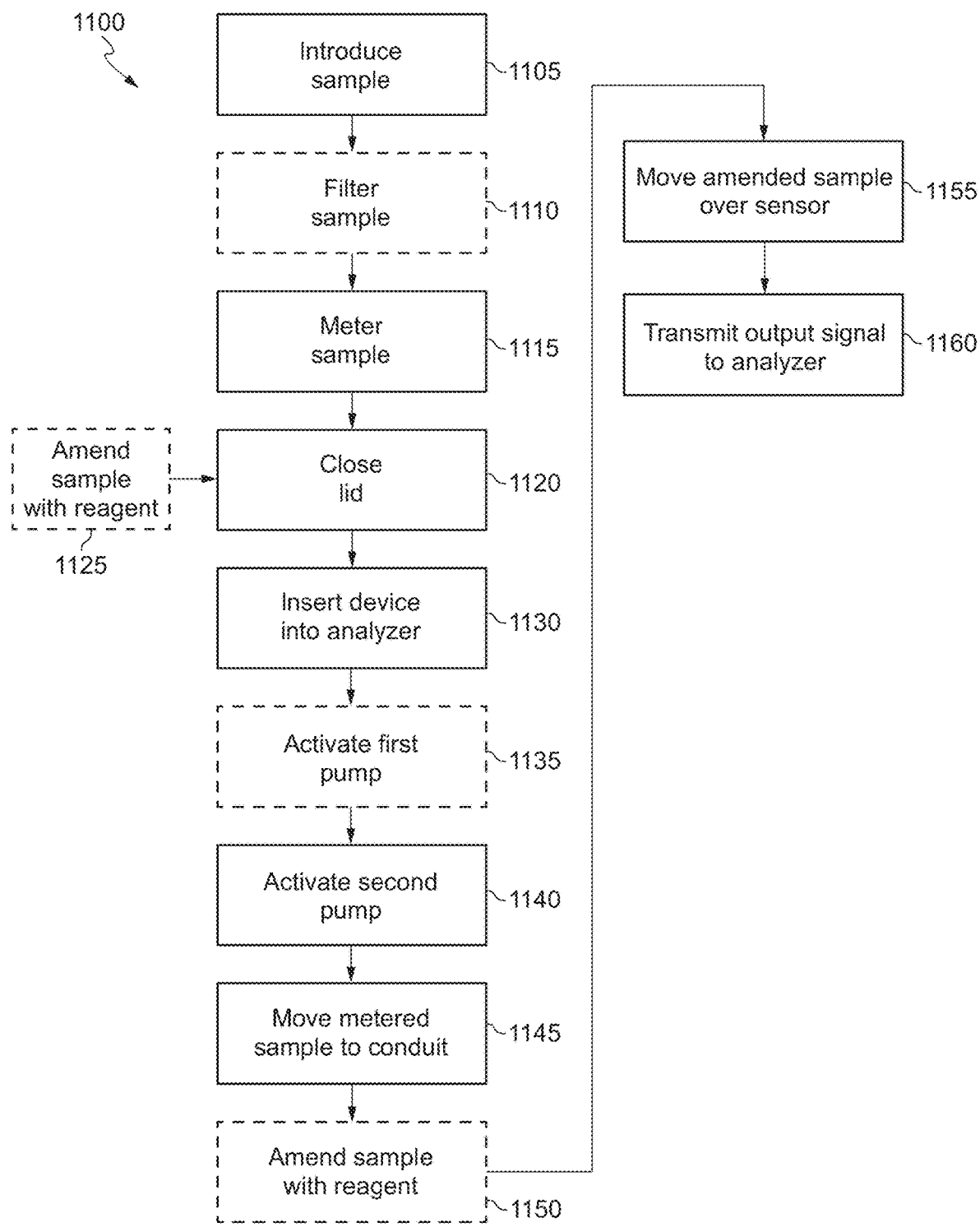
FIGS. 11-16 show processes in accordance with various embodiments.

FIG. 11 illustrates a method 1100 (with reference to the testing device 400 as illustrated in FIGS. 4A-4J) of using a testing device to perform an optical assay in accordance with one embodiment of the invention. At step 1105, an unmetered biological sample may be introduced into a sample chamber (e.g., the sample holding chamber 410 described with respect to FIGS. 4G and 4H) of a testing device, through a sample entry port (e.g., sealable sample entry port 406 described with respect to FIGS. 4B and 4C). Optionally at step 1110, the biological sample may be filtered to remove cells such that only a plasma fraction of the sample reaches the sensors (e.g., if the cells are not substantially removed they may scatter the light from the LED and affect assay performance). In some embodiments, the sample holding chamber comprises the filter material such that only the plasma fraction reaches the sample metering portion of the device. In other embodiments, a first conduit (e.g., conduit 431 described with respect to FIG. 4A) comprises the filter material such that the metered portion of the sample is filtered to remove the cells. At step 1115, a capillary stop (e.g., capillary stop 412 described with respect to FIGS. 4G and 4H) may prevent passage of the sample into the first conduit (e.g., conduit 431 described with respect to FIG. 4A) at this stage, and the sample chamber is filled with the sample. The capillary stop at the end of the sample chamber delimits a metered portion of the biological sample. At step 1120, a lid (e.g., closable sealing member 408 described with respect to FIGS. 4A and 4B) maybe closed to prevent leakage of the biological sample from the sensing device. While the biological sample is within sample chamber or the first conduit, the biological sample may be optionally amended at step 1125 with a compound or compounds (e.g., reagents such as enzymes, enzyme substrate, activators, stabilizers, buffers, enzyme-labeled antibody conjugate and the like) present initially as a dry coating on the inner surface of the sample chamber or first conduit.

At step 1130, the sensing device may be inserted into an analyzer (e.g., analyzer 105 described with respect to FIG. 1) in accordance with some aspects of the present invention. Optionally at step 1135, insertion of the sensing device into the analyzer may activate a first pump (e.g., the portion of the flexible zone 436 as described with respect to FIGS. 4A and 4B) or mechanism that punctures a fluid-containing package when the package is pressed against a spike (e.g., spike 425 as described with respect to FIGS. 4G and 4H). Fluid (e.g., a substrate) may thereby be expelled into a second conduit (e.g., conduit 422 as described with respect to FIGS. 4G and 4H) that is in fluidic communication with the first conduit. A constriction in the second conduit prevents further movement of the fluid. At step 1040, operation of a second pump (e.g., displaceable membrane 426 as described with respect to FIGS. 4A, 4B, 4G, and 4H) by the analyzer applies pressure to an air-bladder of the sensing device, forcing air through a third conduit (e.g., conduit 429 as described with respect to FIGS. 4G and 4H) and into the sample chamber at a predetermined location.

At step 1145, the metered portion of the biological sample is expelled through the capillary stop by air pressure produced within the air-bladder at step 1140 into the first conduit. Optionally at step 1150, the biological sample is moved forward within the first conduit to a portion of the first conduit (e.g., conduit 431 as described with respect to FIG. 4A) that is exposed to a sensor chip (e.g., sensor chip 600 as described with respect to FIG. 6A) by air pressure produced within the air-bladder such that the biological specimen can be amended with a compound or compounds (e.g., reagents such as enzymes, enzyme substrate, activators, stabilizers, buffers, enzyme-labeled antibody conjugate and the like) present initially as a dry coating on a portion of the sensor chip (i.e., one or more reagent regions). Additionally or alternatively, the fluid in the second conduit may be moved past the constriction into the first conduit and into contact with the biological specimen by air pressure produced by the first pump. The fluid may include a substrate that may be acted upon by the biological specimen and/or amended compounds to produce a chromatic substance. To facilitate the dissolution of the substrate, compound or compounds in the biological sample and/or promote efficient reaction, the biological sample may be oscillated by air pressure produced within the air-bladder. In one embodiment, an oscillation frequency of between about 0.2 Hz and about 5 Hz is used, most preferably about 0.7 Hz.

At step 1155, the biological sample is move forward within the first conduit to a portion of the first conduit (e.g., conduit 431 as described with respect to FIG. 4A) that is exposed to the sensor chip (e.g., sensor chip 600 as described with respect to FIG. 6A) by air pressure produced within the air-bladder such that analysis (e.g., optical analysis) of the biological specimen can be performed. In various embodiments, the biological sample is moved forward within the first conduit to a position over an optical sensor such that one or more light emitters can transmit incident light of one or more wavelengths into the portion of the first conduit and the biological specimen. Upon the incident light striking the biological sample, photons that match an energy gap of a target analyte or a chromatic substance related to a presence of the target analyte present in the biological specimen are absorbed. Other photons transmit through the first conduit and biological specimen unaffected. The one or more light detectors collect the photons of light transmitted through the first conduit and the biological sample, and convert the transmitted photons of light into current. At step 1060, the current is transmitted to the analyzer as an output signal via a conductive contact, and the analyzer compares the attenuation of the transmitted light with the incident light to obtain an absorption spectrum and converts the output signal to an analyte signal proportional to the light received from the conduit and collected by the one or more light detectors.

Figure 12:
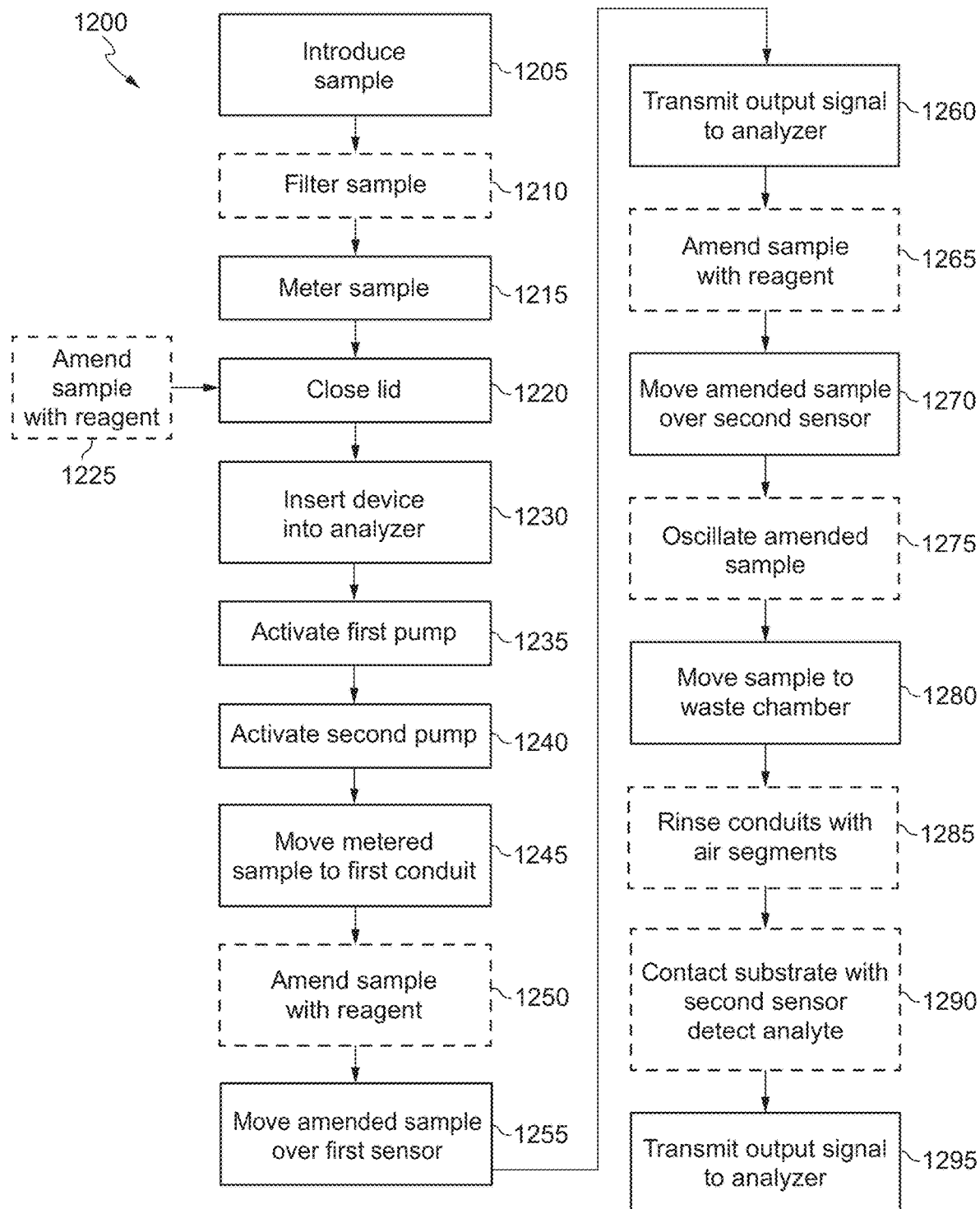

FIG. 12 illustrates a method 1200 (with reference to the testing device 400 as illustrated in FIGS. 4A-4J) of using a testing device to perform an optical assay and an electrochemical assay in accordance with one embodiment of the invention. At step 1205, an unmetered biological sample may be introduced into a sample chamber (e.g., the sample holding chamber 410 described with respect to FIGS. 4G and 4H) of a testing device, through a sample entry port (e.g., sealable sample entry port 406 described with respect to FIGS. 4B and 4C). Optionally at step 1210, the biological sample may be filtered to remove cells such that only a plasma fraction of the sample reaches the sensors (e.g., if the cells are not substantially removed they may scatter the light from the LED and affect assay performance). In some embodiments, the sample holding chamber comprises the filter material such that only the plasma fraction reaches the sample metering portion of the device. In other embodiments, a first conduit (e.g., conduit 431 described with respect to FIG. 4A) comprises the filter material such that the metered portion of the sample is filtered to remove the cells. At step 1215, a capillary stop (e.g., capillary stop 412 described with respect to FIGS. 4G and 4H) may prevent passage of the sample into the first conduit (e.g., conduit 431 described with respect to FIG. 4A) at this stage, and the sample chamber is filled with the sample. The capillary stop at the end of the sample chamber delimits a metered portion of the biological sample. At step 1220, a lid (e.g., closable sealing member 408 described with respect to FIGS. 4A and 4B) maybe closed to prevent leakage of the biological sample from the sensing device. While the biological sample is within sample chamber or the first conduit, the biological sample may be optionally amended at step 1225 with a compound or compounds (e.g., reagents such as enzymes, enzyme substrate, activators, stabilizers, buffers, enzyme-labeled antibody conjugate and the like) present initially as a dry coating on the inner surface of the sample chamber or first conduit.

At step 1230, the sensing device may be inserted into an analyzer (e.g., analyzer 105 described with respect to FIG. 1) in accordance with some aspects of the present invention. At step 1235, insertion of the sensing device into the analyzer may activate a first pump (e.g., the portion of the flexible zone 436 as described with respect to FIGS. 4A and 4B) or mechanism that punctures a fluid-containing package when the package is pressed against a spike (e.g., spike 425 as described with respect to FIGS. 4G and 4H). Fluid (e.g., a substrate) may thereby be expelled into a second conduit (e.g., conduit 422 as described with respect to FIGS. 4G and 4H) that is in fluidic communication with the first conduit. A constriction in the second conduit prevents further movement of the fluid. At step 1240, operation of a second pump (e.g., displaceable membrane 426 as described with respect to FIGS. 4A, 4B, 4G, and 4H) by the analyzer applies pressure to an air-bladder of the sensing device, forcing air through a third conduit (e.g., conduit 429 as described with respect to FIGS. 4G and 4H) and into the sample chamber at a predetermined location.

At step 1245, the metered portion of the biological sample is expelled through the capillary stop by air pressure produced within the air-bladder at step 1240 into the first conduit. Optionally at step 1250, the biological sample is moved forward within the first conduit to a portion of the first conduit (e.g., conduit 431 as described with respect to FIG. 4A) that is exposed to a sensor chip (e.g., sensor chip 600 as described with respect to FIG. 6A) by air pressure produced within the air-bladder such that the biological specimen can be amended with a compound or compounds (e.g., (e.g., reagents such as enzymes, enzyme substrate, activators, stabilizers, buffers, enzyme-labeled antibody conjugate and the like) present initially as a dry coating on a portion of the sensor chip (i.e., one or more reagent regions). Additionally or alternatively, the fluid in the second conduit may be moved past the constriction into the first conduit and into contact with the biological specimen by air pressure produced by the first pump. The fluid may include a substrate that may be acted upon by the biological specimen and/or amended compounds to produce a chromatic substance. To facilitate the dissolution of the substrate, compound or compounds in the biological sample and/or promote efficient reaction, the biological sample may be oscillated by air pressure produced within the air-bladder. In one embodiment, an oscillation frequency of between about 0.2 Hz and about 5 Hz is used, most preferably about 0.7 Hz.

At step 1255, the biological sample is moved forward within the first conduit to a position over a first sensor (e.g., an optical sensor) by air pressure produced within the air-bladder. In various embodiments, the biological sample is moved forward within the first conduit to a position over an optical sensor such that one or more light emitters can transmit incident light of one or more wavelengths into the portion of the first conduit and the biological specimen. Upon the incident light striking the biological sample, photons that match an energy gap of a target analyte or a chromatic substance related to a presence of the target analyte present in the biological specimen are absorbed. Other photons transmit through the first conduit and biological specimen unaffected. The one or more light detectors collect the photons of light transmitted through the first conduit and the biological sample, and convert the transmitted photons of light into current. At step 1260, the current is transmitted to the analyzer as an output signal via a conductive contact, and the analyzer compares the attenuation of the transmitted light with the incident light to obtain an absorption spectrum and converts the output signal to an analyte signal proportional to the light received from the conduit and collected by the one or more light detectors.

Optionally at step 1265, the biological sample is moved forward such that the biological specimen can be amended with a compound or compounds (e.g., reagents such as an enzyme and enzyme substrate-labeled antibody conjugate) present initially as a dry coating on a portion of the sensor chip (i.e., one or more reagent regions). To facilitate the dissolution of the compound or compounds in the biological sample and/or promote efficient reaction, the biological sample may be oscillated over the one or more reagent regions by air pressure produced within the air-bladder. In one embodiment, an oscillation frequency of between about 0.2 Hz and about 5 Hz is used, most preferably about 0.7 Hz. At step 1270, the biological sample is moved forward within the first conduit to a position over a second sensor (e.g., an amperometric sensor) by air pressure produced within the air-bladder. Optionally at step 1275, to promote efficient reaction product formation sandwich formation on or near the surface of the second sensor comprising a biolayer, the biological sample may be oscillated over the second sensors by air pressure produced within the air-bladder. In one embodiment, an oscillation frequency of between about 0.2 Hz and about 5 Hz is used, most preferably about 0.7 Hz At step 1280, the biological sample is displaced from the first conduit by further pressure applied to air-bladder, and the biological sample passes to a waste chamber (e.g., waste chamber 416 as described with respect to FIGS. 4A and 4G.). At optional step 1285, one or more air segments (meniscus) may be produced within the first conduit by any suitable means, including a passive means, an embodiment of which is described in detail in U.S. Pat. No. 7,682,833, which is incorporated herein by reference in its entirety, or an active means including a transient lowering of the pressure within the first conduit using the second pump whereby air is drawn into the first conduit through a flap or valve. The one or more air segments are extremely effective at clearing or rinsing the biological sample-contaminated fluid from the first conduit. For example, a leading and/or trailing edge of the one or more air segments may be passed a number of times over the first and second sensors to rinse and resuspend extraneous material that may have been deposited from the biological sample. Extraneous material includes any material other than specifically bound analyte or analyte/antibody-enzyme conjugate complex. However, in accordance with various embodiments, the clearing or rinsing step 1285 using the one or more air segments is not sufficiently protracted or vigorous so as to promote substantial dissociation of specifically bound analyte or analyte/antibody-enzyme conjugate complex from a biolayer.

Optionally at step 1290, the fluid in the second conduit is moved past the constriction into the first conduit and into contact with the second sensor by air pressure produced by the first pump. The fluid may include an optical calibrator, e.g. a known concentration of a dye with a known extinction coefficient, substrate or signal agent and the enzyme remaining within the first conduit and immobilized on or near the second sensor either produces an electroactive species from an electro-inactive substrate or destroys an electroactive substrate. In some embodiments, the fluid may be applied to the second sensor to wash the biological sample from the second sensor. At step 1295, a change in current or potential generated by the production or destruction of the electroactive species at the second sensor and the change is transmitted as a function of time to the analyzer via a conductive contact, and the analyzer performs analysis of the change in current or potential to identify the presence and/or concentration of the target analyte in the biological specimen.

As should be understood, the previous steps could be split up into two or more processes for using two or more testing devices to perform an optical assay and an electrochemical assay in accordance with alternative embodiments of the invention. For example, the steps pertaining to the optical assay could be performed via an optical testing device and subsequently the steps pertaining to the electrochemical assay could be performed via an electrochemical testing device, or vice versa.

Figure 13:
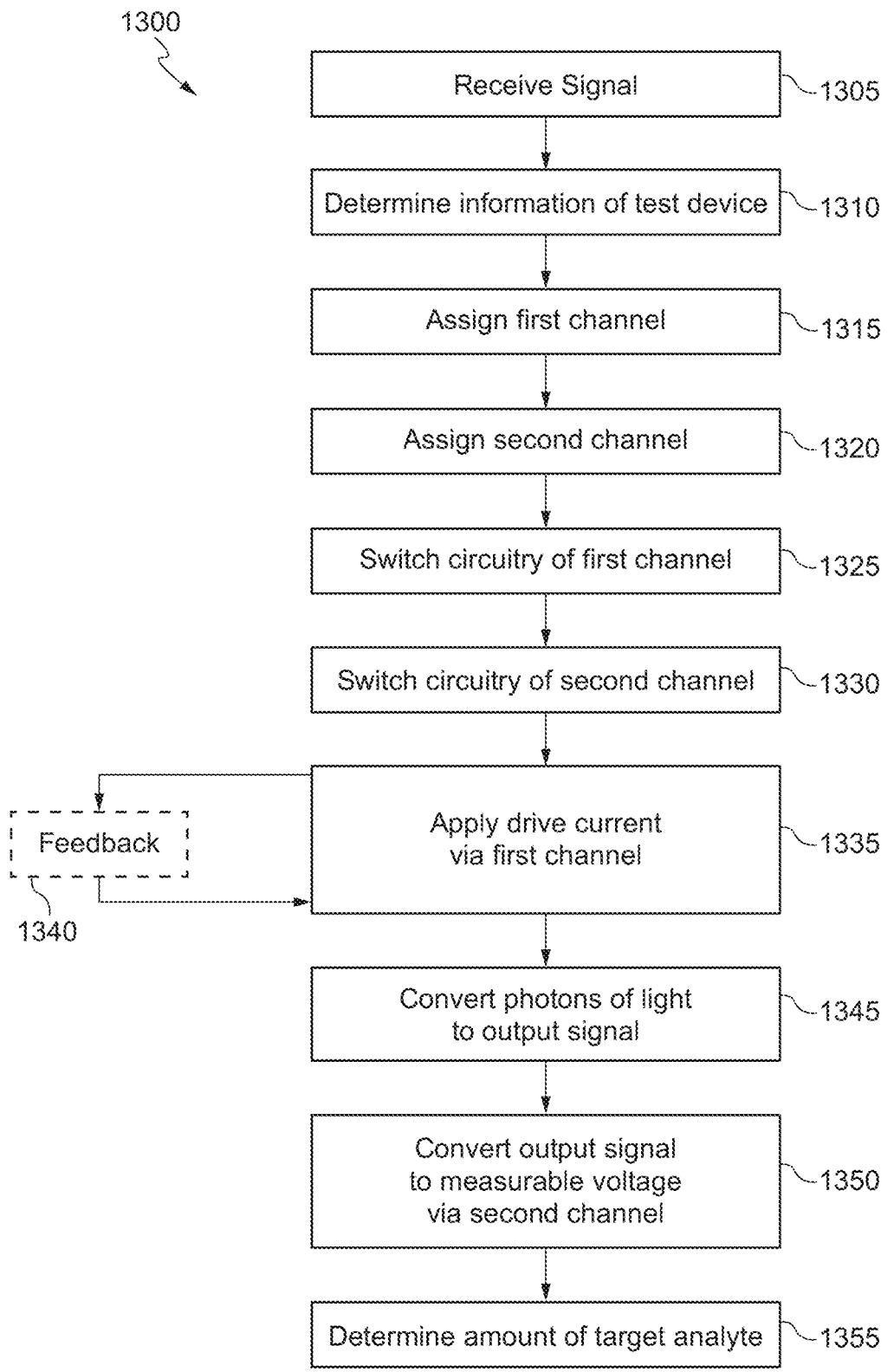

FIG. 13 illustrates a method 1300 of performing an optical assay for determining the presence and/or concentration of an analyte in a biological sample (e.g., whole blood) in accordance with various embodiments of the invention. At step 1305, an operating state signal is received that is indicative of a type of test cartridge inserted into an analyzer. In some embodiments, the operating state signal comprises a value of a measured resistance between contacts of the test cartridge and a shorting bar. For example, in order to impart cartridge identification functionality into a test cartridge, an additional mechanism or means may be included in the sensor chip arrangement for cartridge identification. In certain embodiments, a resistor can be implemented between contacts. The resistance of the resistor may be measured by a detector (e.g., processor) by applying a small voltage, e.g., 1 mV, between the contacts, subsequent to (e.g., immediately after) the cartridge being inserted into the analyzer. The value of the measured resistance can then be used for cartridge identification. For example, each cartridge type (e.g., i-STAT® cartridges EC8+, CG8+, EG7+, CHEM8+, etc.) may be associated with a certain resistance or resistance range such that a measured resistance of the cartridge may be used to identify the type of cartridge using a look-up table.

In alternative embodiments, the operating state signal comprises a value obtained from a barcode located on the test cartridge or a package of the test cartridge. For example, an imaging area of the test cartridge may be used to scan a barcode to obtain a value using the barcode reader of the instrument 110, as described with respect to FIG. 1. The value of barcode can then be used for cartridge identification. For example, each cartridge type (e.g., i-STAT® cartridges EC8+, CG8+, EG7+, CHEM8+, etc.) may be associated with a certain value such that a scanned value of the cartridge may be used to identify the type of cartridge using a look-up table retained in the instrument.

At step 1310, information regarding sensors of the test cartridge are determined based on the identified type of cartridge. In certain embodiments, determining the information comprises: identifying, based on a value of the operating state signal, the type of test cartridge using a look-up table, and obtaining, based on the type of test cartridge, the information regarding the sensors from a database, where the database has information for each type of test cartridge. In various embodiments, the information indicates the type of sensors of the test cartridge (e.g., one or more optical sensors, one or more reference electrode, one or more electrochemical sensors, etc) and the position of conductive contacts connected to the sensors of the test cartridge In addition or alternative to obtaining information regarding the type of sensors and the position of conductive contacts from the database via the identified type of testing cartridge, the type of sensors and position of the conductive contacts may be identified using information obtained regarding the connector pins in contact with the various conductive contacts of the testing cartridge. For example, the analyzer connector may be a linear array of connector pins, e.g., pins one to twenty. The type of sensors and position of the conductive contacts may be identified via the position of each pin relative to the contacts. For example, a light emitter of an optical sensor may be connected via a contact to a pin "x" (e.g., pin 11) and a light detector of the optical sensor may be connected via another contact to a pin "y" (e.g., 12), and thus since both pins 11 and 12 are being used, the type of sensor (optical) and components (e.g., light emitter and light detector) connected to the contacts can be identified via the database. Consequently, as described herein, the analyzer may then assign channels of the universal circuitry to the appropriate pins for the types of sensors determined to be in the identified testing cartridge. As should be understood, once a test cycle is run and the testing cartridge is removed from the instrument or analyzer, the channels of the universal circuitry can be reassigned to the same or different connector pins when a new testing cartridge is inserted into the analyzer.

At step 1315, a first channel is assigned to the light emitter via: (i) the first contact and a corresponding first pin, and optionally, (ii) the second contact and a corresponding second pin. At step 1320, a second channel is assigned to the light detector via the third contact and a corresponding third pin.

At step 1325, the circuitry of the first channel is switched to a current driver mode. In some embodiments, the switching the circuitry of the first channel comprises modifying switching elements of the circuitry such that the first channel is configured to apply the drive current via the first contact and the corresponding first pin to the light emitter. At step 1330, the circuitry of the second channel is switched to a current measurement mode. In some embodiments, the switching the circuitry of the second channel comprises modifying switching elements of the circuitry such that the second channel is configured to convert output current received from the light detector to a measurable voltage proportional to an amount light detected by the light detector.

At step 1335, a drive current is applied to the light emitter using the first channel. The applying the drive current to the light emitter causes the light emitter to generate output current and light comprising a predetermined wavelength that is projected into a portion of a conduit. Optionally at step 1340, the output current generated by the light emitter is received at the first channel from the second contact and the corresponding second pin, and the output current is applied to a feedback resistor to establish a constant current for the drive current.

At step 1345, the light detector converts the photons of light received from the light emitter to an output current and sends the output current to the third contact as an output signal. At step 1350, the output signal from the light detector is received at the second channel via the third contact and the corresponding third pin. The output signal may be converted, using the second channel, to a measurable voltage or analyte signal proportional to an amount light received from the portion of the conduit and detected by the light detector. At step 1355, a qualitative, semi-quantitative, or quantitative value that is proportional to an amount of target analyte in the biological specimen is determined based on the measurable voltage or analyte signal.

Figure 14:
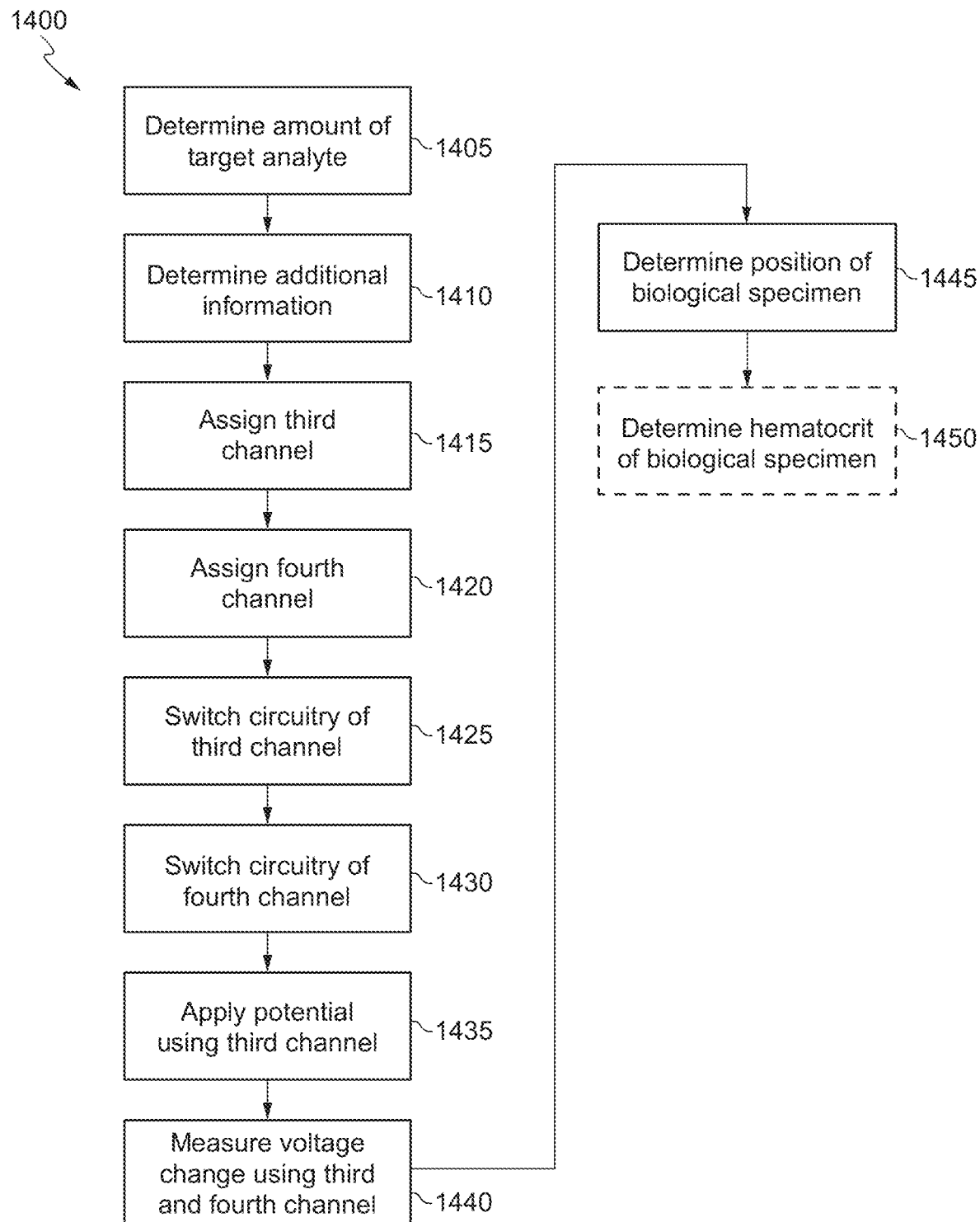

FIG. 14 illustrates a method 1400 of performing an optical assay and using a conductometric sensor to determine a location of a biological sample in a test cartridge and/or determine a hematocrit level of the biological specimen. At step 1405, a qualitative, semi-quantitative, or quantitative value is determined based on a measurable voltage that is proportional to an amount of target analyte in the biological specimen in accordance with steps 1305-1355 of method 1300. At step 1410, additional/alternative information regarding sensors of the test cartridge is determined based on the type of the test cartridge and/or the pins being used. In various embodiments, the information indicates that one of the first contact, the second contact, the third contact, or a fourth contact is connected to a first conductometric electrode, and one of the first contact, the second contact, the third contact, or the fourth contact is connected to a second conductometric electrode.

At step 1415, a third channel is assigned to the first conductometric electrode via the first contact, the second contact, the third contact, or a fourth contact and the corresponding first pin, the second pin, the third pin, or a fourth pin. At step 1420, a fourth channel is assigned to the second conductometric electrode via the first contact, the second contact, the third contact, or a fourth contact and the corresponding first pin, the second pin, the third pin, or a fourth pin. At step 1425, the circuitry of the third channel is switched to a high conductometric mode. In some embodiments, the switching the circuitry of the third channel comprises modifying switching elements of the circuitry such that the third channel is configured to apply a potential to the first conductometric electrode and measure a voltage change across the biological specimen that is proportional to conductivity of the biological specimen. At step 1430, the circuitry of the fourth channel is switched to a low conductometric mode. In some embodiments, the switching the circuitry of the fourth channel comprises modifying switching elements of the circuitry such that the fourth channel is configured to apply a potential to the second conductometric electrode and measure a voltage change across the biological specimen that is proportional to conductivity of the biological specimen.

At step 1435, a potential is applied to the to the first conductometric electrode using the third channel. At step 1440, a voltage change across the biological specimen is measured, using, using the third channel and the fourth channel, that is proportional to conductivity of the biological specimen. At step 1445, a position of the biological specimen is determined within the testing device based on the voltage change across the biological specimen. Optionally at step 1450, a hematocrit level of the biological specimen is determined by comparing the voltage change to known values of hematocrit on a calibration curve and converting the value of the hematocrit to a rating for the hematocrit level.

Figure 15:
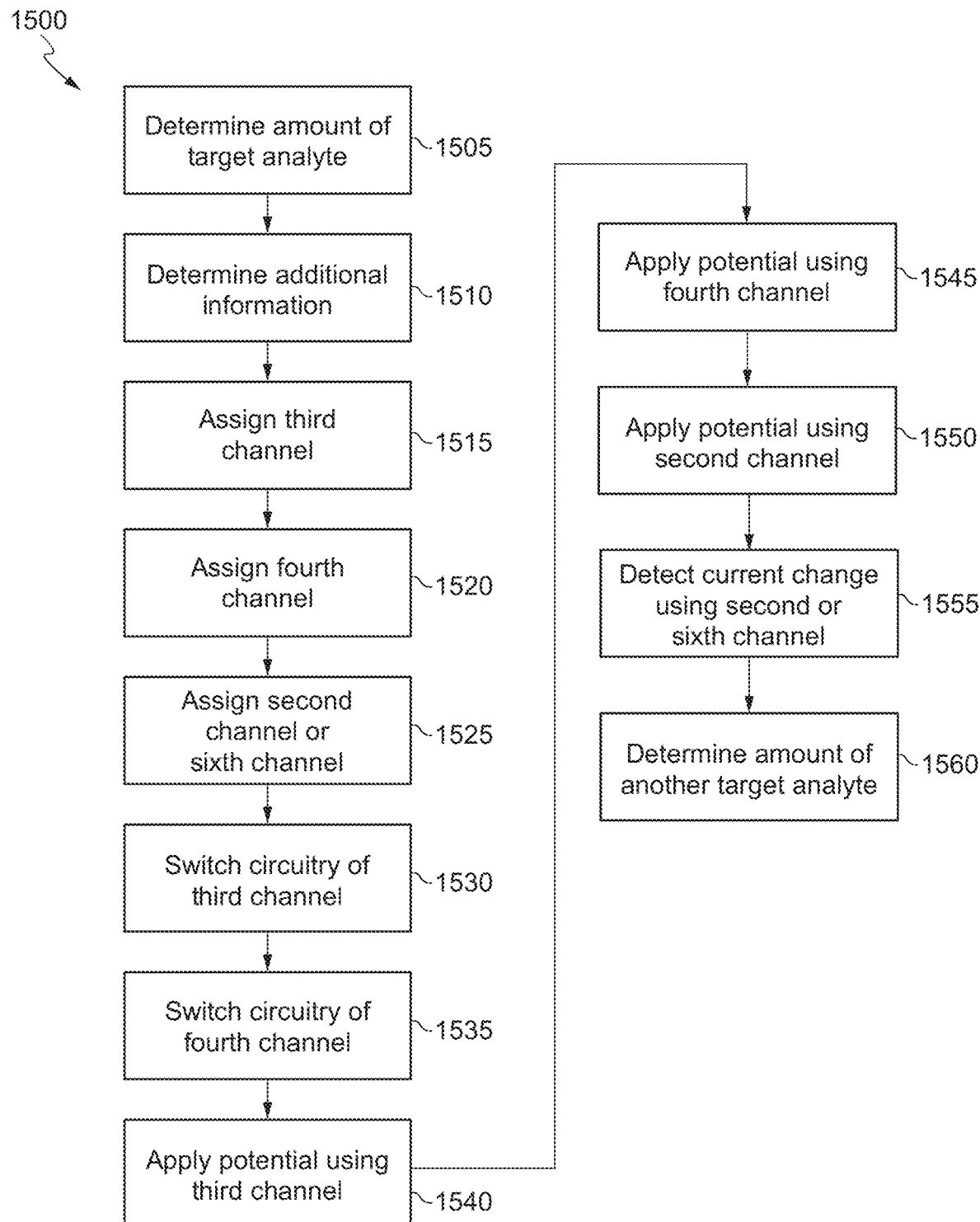

FIG. 15 illustrates a method 1500 of performing an optical assay and electrochemical assay using a same testing device. At step 1505, a qualitative, semi-quantitative, or quantitative value is determined based on a measurable voltage that is proportional to an amount of target analyte in the biological specimen in accordance with steps 1305-1355 of method 1300. At step 1510, additional/alternative information regarding sensors of the test cartridge is determined based on the type of the test cartridge and/or the pins being used. In various embodiments, the information indicates that a fourth contact is connected to a counter electrode, a fifth contact is connected to a reference electrode, and the third contact or a sixth contact is connected to a working electrode (e.g., an amperometric electrode).

At step 1515, a third channel is assigned to the counter electrode via the fourth contact and a corresponding fourth pin. At step 1520, a fourth channel is assigned to the reference electrode via the fifth contact and a corresponding fifth pin. At step 1525, the second channel is assigned to the working electrode via the third contact and the corresponding third pin or the sixth contact and a corresponding sixth pin. At step 1530, the circuitry of the third channel is switched to a counter measurement mode. In some embodiments, the switching the circuitry of the third channel comprises modifying switching elements of the circuitry such that the third channel is configured to apply a potential that is optionally not measured and is adjusted so as to balance the reaction occurring at the working electrode. This configuration allows the potential of the working electrode to be measured against a known electrode (i.e., the counter electrode) without compromising the stability of the reference electrode by passing current over the reference electrode. At step 1535, the circuitry of the fourth channel is switched to a reference measurement mode. In some embodiments, the switching the circuitry of the fourth channel comprises modifying switching elements of the circuitry such that the fourth channel is configured to apply a stable potential to the reference electrode, which may be used as a reference for measurements made by the working electrode.

At step 1540, a potential is applied to the counter electrode using the third channel. At step 1545, a potential is applied to the reference electrode using the fourth channel. At step 1550, a potential is applied to the working electrode using the second channel. At step 1555, a current change across the biological specimen is measured, using the second channel, that is proportional to a concentration of another target analyte within the biological specimen. In various embodiments, the counter electrode and the reference electrode are used in conjunction with the working electrode to measure the current change across the biological specimen. At step 1560, the concentration of another target analyte within the biological specimen is determined based on the current change across the biological specimen.

Figure 16:
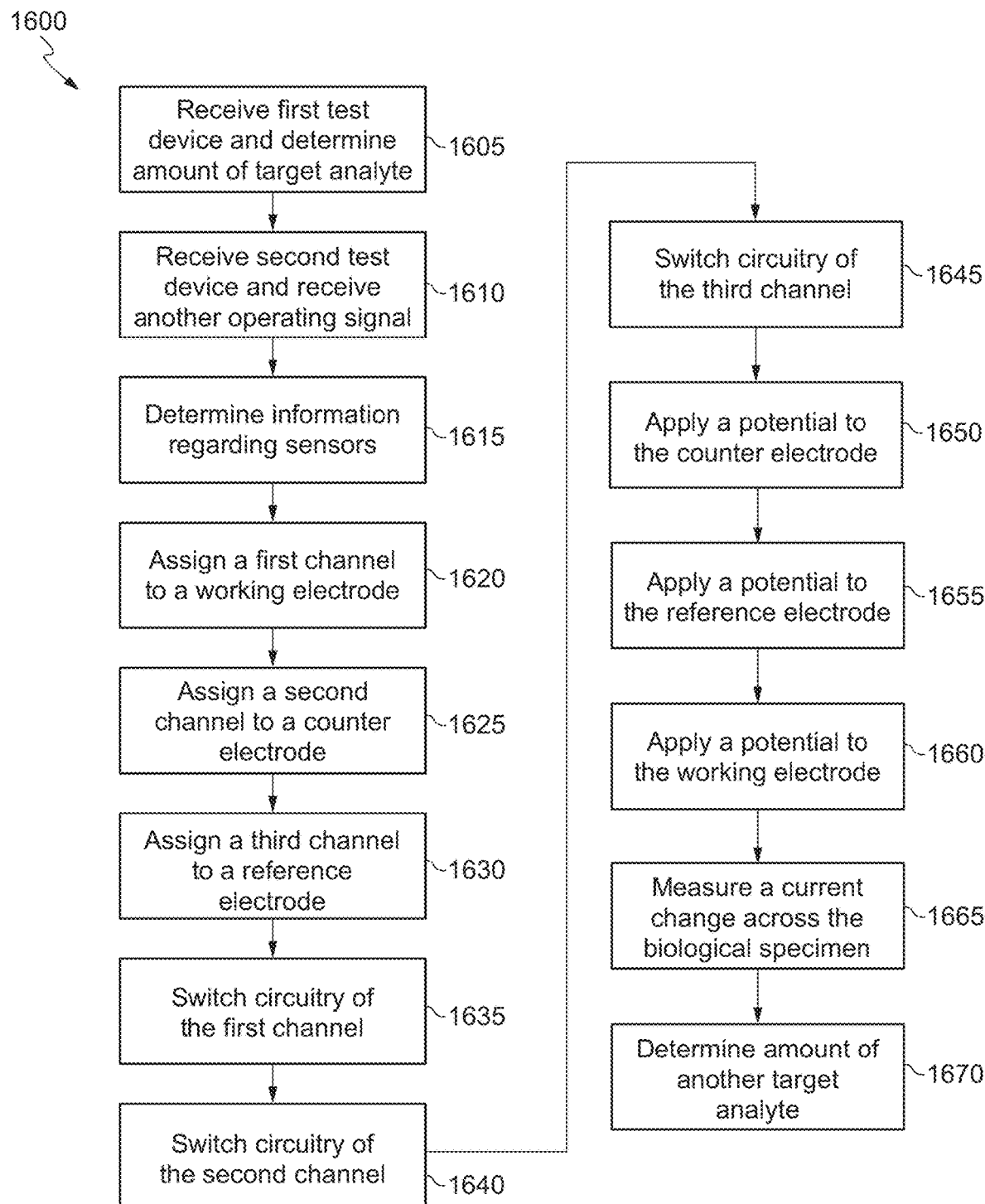

FIG. 16 illustrates a method 1600 of performing an optical assay and electrochemical assay using different testing devices. At step 1605, a first test device (e.g., an optical testing device) is received and a qualitative, semi-quantitative, or quantitative value is determined based on a measurable voltage that is proportional to an amount of target analyte in the biological specimen in accordance with steps 1305-1355 of method 1300. At step 1610 (subsequent to step 1605), a second test device (e.g., an electrochemical testing device) is inserted into the analyzer and another operating state signal is received that is indicative of a type of test cartridge inserted into the analyzer. In some embodiments, the operating state signal comprises a value of a measured resistance between contacts of the test cartridge and a shorting bar, as described with respect to FIG. 13. In alternative embodiments, the operating state signal comprises a value obtained from a barcode located on the test cartridge or a package of the test cartridge, as described with respect to FIG. 13.

At step 1615, information regarding sensors of the test cartridge are determined based on the identified type of cartridge, as described with respect to FIG. 13. For example, the analyzer connector may be a linear array of connector pins, e.g., pins one to twenty. The type of sensors and position of the conductive contacts may be identified via the position of each pin relative to the contacts. For example, an amperometric electrode may be connected via a contact to a pin "x" (e.g., pin 5) and reference electrode may be connected via another contact to a pin "y" (e.g., 6), and thus since both pins 5 and 6 are being used, the type of sensor (amperometric) and components (e.g., amperometric electrode and reference electrode) connected to the contacts can be identified via the database. Consequently, as described herein, the analyzer may then assign channels of the universal circuitry to the appropriate pins for the types of sensors determined to be in the identified testing cartridge. As should be understood, once a test cycle is run and the testing cartridge is removed from the instrument or analyzer, the channels of the universal circuitry can be reassigned to the same or different connector pins when a new testing cartridge is inserted into the analyzer.

At step 1620, a first channel is assigned to a working electrode via a first contact and a corresponding first pin. At step 1625, a second channel is assigned to a counter electrode via a second contact and a corresponding second pin. At step 1630, a third channel is assigned to the reference electrode via the third contact and a corresponding third pin. At step 1635, the circuitry of the first channel is switched to a measurement mode (e.g., an amperometric measurement mode). In some embodiments, the switching the circuitry of the first channel comprises modifying switching elements of the circuitry such that the first channel is configured to apply a potential via the first contact and the corresponding first pin to working electrode. At step 1640, the circuitry of the second channel is switched to a counter measurement mode. In some embodiments, the switching the circuitry of the second channel comprises modifying switching elements of the circuitry such that the second channel is configured to apply a potential that is optionally not measured and is adjusted so as to balance the reaction occurring at the working electrode. This configuration allows the potential of the working electrode to be measured against a known electrode (i.e., the counter electrode) without compromising the stability of the reference electrode by passing current over the reference electrode. At step 1645, the circuitry of the third channel is switched to a reference measurement mode. In some embodiments, the switching the circuitry of the third channel comprises modifying switching elements of the circuitry such that the third channel is configured to apply a stable potential to the reference electrode, which may be used as a reference for measurements made by the working electrode.

At step 1650, a potential is applied to the counter electrode using the second channel. At step 1655, a potential is applied to the reference electrode using the third channel. At step 1660, a potential is applied to the working electrode using the first channel. At step 1665, a current change across the biological specimen is measured, using the first channel, that is proportional to a concentration of another target analyte within the biological specimen. In various embodiments, the counter electrode and the reference electrode are used in conjunction with the working electrode to measure the current change across the biological specimen. At step 1670, the concentration of another target analyte within the biological specimen is determined based on the current change across the biological specimen.

As should be understood, the first test device and the second test device could be received in reverse order with an electrochemical testing device received first and an optical testing device received second. Moreover, it should be understood that more than two cartridges could be received subsequent to one another and the analyzer is contemplated to perform analytical tests on tens to hundreds of various testing cartridges per day.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

We claim:

1. A system for performing an optical assay on a biological sample, comprising:
   an analyzer comprising: a port, a multi-terminal connector, a processor, memory coupled to the processor, and universal channel circuitry, wherein the universal channel circuitry comprises one or more electronic switches and is electrically connected to the multi-terminal connector; and
   a test cartridge comprising:
      a plurality of discrete connector contacts,
      a sample receiving chamber fluidically connected to a conduit, and
      an analyte assay region comprising: a portion of the conduit, a light emitter, and a light detector,
   wherein the test cartridge is insertable into the port such that the multi-terminal connector is in electrical contact with the plurality of discrete connector contacts;
   wherein the memory is encoded with a set of instructions to perform the optical assay and at least one of: an amperometric analyte assay, a potentiometric analyte assay, and a conductometric assay;
   wherein the set of instructions comprises instructions to arrange the one or more electronic switches of the universal channel circuitry in an optical sensor current measurement mode to perform the optical assay, and at least one of: an amperometric measurement mode to perform the amperometric analyte assay, a potentiometric measurement mode to perform the potentiometric analyte assay, and a conductometric measurement mode to perform the conductometric assay;

wherein to perform the optical assay using the optical sensor current measurement mode, the electronic switches of the universal channel circuitry are arranged to (i) electrically connect the universal channel circuitry to the light emitter via at least one of the plurality of discrete connector contacts of the test cartridge and the multi-terminal connector, (ii) electrically connect the universal channel circuitry to the light detector via at least one of the plurality of discrete connector contacts of the test cartridge and the multi-terminal connector, (iii) drive the light emitter to generate light projected into the portion of the conduit, and (iv) to convert an output signal of the light detector to an analyte signal proportional to the light received from the portion of the conduit; and wherein to perform the amperometric analyte assay using the amperometric measurement mode, the electronic switches of the universal channel circuitry are arranged to connect the universal channel circuitry to an amperometric electrode, to perform the potentiometric analyte assay using the potentiometric measurement mode, the electronic switches of the universal channel circuitry are arranged to connect the universal channel circuitry a to potentiometric electrode, and to perform the conductometric assay using the conductometric measurement mode, the electronic switches of the universal channel circuitry are arranged to connect the universal channel circuitry to a conductometric electrode.

2. The system of claim 1, wherein the light emitter is a light emitting diode (LED) and the light detector is a photodiode (PD), and the test cartridge comprises a plurality of LEDs and a plurality of PDs.

3. The system of claim 1, wherein the light emitter is a light emitting diode (LED) and the light detector is a photodiode (PD), and the test cartridge comprises a plurality of paired LEDs and PDs.

4. The system of claim 3, wherein the plurality of paired LEDs and PDs are located at discrete positions with respect to the conduit.

5. The system of claim 4, wherein each pair of LEDs and PDs is substantially optically isolated from the other pairs of LEDs and PDs.

6. The system of claim 1, wherein the processor is configured to determine a qualitative, semi-quantitative, or quantitative value proportional to an amount of a target analyte in the biological sample based on the analyte signal.

7. The system of claim 6, wherein the target analyte is selected from the group consisting of: human chorionic gonadotropin, glucose, lactate, creatinine, urea, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac troponin (cTnI), human chorionic gonadotropin, troponin T, troponin C, myoglobin, neutrophil gelatinase-associated lipocalin (NGAL), galectin-3, prostate-specific antigen (PSA), parathyroid hormone (PTH), galectin-3, aspartate aminotransferase (AST), alanine aminotransferase (ALT), albumin, total protein, bilirubin, and alkaline phosphatase (ALP).

8. The system of claim 1, wherein the test cartridge further comprises a mirrored reflector that reflects light from the light emitter through the conduit to the light detector.

9. The system of claim 8, wherein the mirrored reflector is at least a portion of a surface of the conduit.

10. The system of claim 1, wherein the test cartridge further comprises a filter between the sample receiving chamber and the conduit, and the filter is configured to retain blood cells from the biological sample and permit passage of plasma.

11. The system of claim 1, wherein the light emitter emits the light at a wavelength or range of wavelengths selected in a range of 405 nm to 850 nm.

12. The system of claim 1, wherein the light detector detects the light at a wavelength or range of wavelengths selected in a range of 400 nm to 1000 nm.

13. The system of claim 1, wherein the test cartridge further comprises a neutral density light filter.

14. The system of claim 1, wherein, to perform the optical assay using the optical sensor current measurement mode, the universal channel circuitry comprises a first channel electrically connected to the light emitter via the at least one of the plurality of discrete connector contacts of the test cartridge and the multi-terminal connector, and a second channel electrically connected to the light detector via the at least one of the plurality of discrete connector contacts of the test cartridge and the multi-terminal connector.

15. The system of claim 14, wherein the first channel includes circuitry configured in a current driver mode and the second channel includes circuitry configured in a current measurement mode.

16. The system of claim 15, wherein the circuitry of the first channel comprises a first amplifier connected to a contact of the light emitter, and the circuitry of the second channel comprises a second amplifier connected to a contact of the light detector.

17. The system of claim 16, wherein the universal channel circuitry further comprises a third channel electrically connected to the light emitter and/or the light detector via the at least one of the plurality of discrete connector contacts of the test cartridge and the multi-terminal connector, the third channel includes circuitry configured in a feedback mode and/or a ground mode, and the circuitry of the third channel comprises a one or more resistors connected to the light emitter and/or ground connected to the light emitter and/or the light detector.

18. A system for performing an optical assay for a target analyte in a biological sample, comprising:
an analyzer comprising: a port, a multi-terminal connector, a processor, memory coupled to the processor, and universal channel circuitry, wherein the universal channel circuitry comprises one or more electronic switches, a first channel, and a second channel; and
a test cartridge comprising:
a sample receiving chamber, and
a sensor region comprising: a conduit fluidically connected to the sample receiving chamber, a light emitter connected to a first contact, and a light detector connected to a second contact,
wherein the memory is encoded with a set of instructions to perform the optical assay and at least one of: an amperometric analyte assay, a potentiometric analyte assay, and a conductometric assay;
wherein the set of instructions comprises instructions to arrange the one or more electronic switches of the universal channel circuitry in an optical sensor current measurement mode to perform the optical assay for the target analyte, and at least one of: an amperometric measurement mode to perform the amperometric analyte assay, a potentiometric measurement mode to perform the potentiometric analyte assay, and a conductometric measurement mode to perform the conductometric assay;

wherein the first contact of the test cartridge is electrically connected to a first pin of the multi-terminal connector and the second contact of the test cartridge is electrically connected to a second pin of the multi-terminal connector;

wherein the first pin is electrically connected to the first channel and the second pin is electrically connected to the second channel;

wherein the first channel comprises electronic switches of the universal channel circuitry that are arranged in the optical sensor current measurement mode to configure the first channel a current driver mode;

wherein the second channel comprises circuitry including electronic switches of the universal channel circuitry that are arranged in the optical sensor current measurement mode to configure the second channel in a current measurement mode; and wherein electronic switches of the universal channel circuitry in the first channel are arrangeable such that the first channel is configured in at least one of: the amperometric measurement mode, the potentiometric measurement mode, and the conductometric measurement mode.

19. The system of claim 18, wherein, to perform the optical assay using the optical sensor current measurement mode, the electronic switches of the universal channel circuitry are arranged to:

in the first channel, to drive the light emitter to generate light projected into a portion of the conduit, and, in the second channel, to convert a current output of the light detector to a measurable voltage proportional to the light received from the portion of the conduit.

20. The system of claim 19, wherein the processor is configured to determine a qualitative, semi-quantitative, or quantitative value proportional to an amount of target analyte in the biological sample based on the measurable voltage.

21. The system of claim 18, wherein the universal channel circuitry further comprises a third channel, the light emitter and/or the light detector is connected to a third contact, the third contact is electrically connected to a third pin of the multi-terminal connector, the third pin is electrically connected to the third channel, and the third channel comprises circuitry including switches that are arranged such that the third channel is configured in a feedback mode and/or a ground mode.

22. A system for performing an optical analyte assay on a biological sample, comprising:

an analyzer comprising: a multi-terminal connector, a processor, and universal channel circuitry that is electrically connected to the multi-terminal connector and comprises one or more electronic switches arrangeable to configure the universal channel circuitry in an optical sensor current measurement mode to perform the optical analyte assay, and at least one of: an amperometric measurement mode to perform an amperometric analyte assay, a potentiometric measurement mode to perform a potentiometric analyte assay, and a conductometric measurement mode, and a test cartridge comprising: a plurality of discrete connector contacts, a sample receiving chamber fluidically connected to a conduit, and an analyte assay region comprising: a portion of the conduit, a light emitter, and a light detector, wherein the universal channel circuitry comprises a first channel connected to a first pin of the multi-terminal connector and a second channel connected to a second pin of the multi-terminal connector, wherein the electronic switches of the universal channel circuitry are arranged to connect the first channel of the analyzer to: (i) the light emitter in the optical sensor current measurement mode, to drive the light emitter to generate light projected into the portion of the conduit, (ii) an amperometric electrode in the amperometric measurement mode, (iii) a potentiometric electrode in the potentiometric measurement mode, or (iv) a first conductometric electrode in the conductometric measurement mode, and wherein the electronic switches of the universal channel circuitry are arranged to connect the second channel of the analyzer to: (i) the light detector in the optical sensor current measurement mode, to convert an output signal of the light detector to an analyte signal proportional to the light received from the portion of the conduit, (ii) a reference electrode in the amperometric measurement mode, (iii) the reference electrode in the potentiometric measurement mode, or (iv) a second conductometric electrode in the conductometric measurement mode.

23. The system of claim 22, wherein the test cartridge further comprises at least one reagent for dissolving into the biological sample.

24. The system of claim 22, wherein the test cartridge further comprises at least one reagent for dissolving into the biological sample and reacting with an analyte in the biological sample and causing a change in optical absorbance.

25. The system of claim 22, wherein the light emitter is a light emitting diode (LED) and the light detector is a photodiode (PD), and the LED and PD are mounted on a silicon substrate.

26. The system of claim 22, wherein the light emitter is a light emitting diode (LED) and the light detector is a photodiode (PD), and the LED and PD are mounted on a transparent plastic substrate.

27. The system of claim 22, wherein the light emitter is a light emitting diode (LED) and the light detector is a photodiode (PD), and the LED and PD are mounted on a polyester substrate.

28. The system of claim 22, wherein the portion of the conduit includes a uniform width dimension in a range of about 0.1 mm to about 4 mm.

29. The system of claim 22, wherein the portion of the conduit includes a uniform height dimension in a range of about 0.1 mm to about 4 mm.

30. The system of claim 22, wherein the test cartridge further comprises a fluid pouch connected to the conduit.

31. The system of claim 30, wherein the fluid pouch comprises a wash fluid, a calibration fluid, or a sample dilution fluid.

32. The system of claim 22, wherein the first channel comprises circuitry including switches that are arranged, to perform the optical analyte assay using the optical sensor current measurement mode, such that the first channel is configured in a current driver mode, and the second channel comprises circuitry including switches that are arranged such that the second channel is configured in a current measurement mode.

33. The system of claim 22, wherein the universal channel circuitry further comprises a third channel, and, wherein to perform the optical analyte assay using the optical sensor current measurement mode, the light emitter and/or the light detector is connected to a third contact, the third contact is electrically connected to a third pin of the multi-terminal connector, the third pin is electrically connected to the third channel, and the third channel comprises circuitry including switches that are arranged such that the third channel is configured in a feedback mode and/or a ground mode.

34. The system of claim 22, wherein the analyzer is portable or stationary.

35. The system of claim 22, wherein the analyzer further comprises a thermal controller for controlling a temperature of the biological sample in the portion of the conduit.

36. The system of claim 22, wherein the light emitter is a light emitting diode (LED) and the light detector is a photodiode (PD), and the LED and PD are mounted a polyimide substrate or printed circuit board.

37. The system of claim 22, wherein the analyzer is battery powered or line powered.

38. An analyzer for performing an optical assay on a biological sample, comprising:
a multi-terminal connector;
a processor;
memory coupled to the processor;
universal channel circuitry, wherein the universal channel circuitry comprises one or more electronic switches and is electrically connected to a multi-terminal connector; and
a port for receiving a test cartridge comprising: a plurality of discrete connector contacts connectable to the multi-terminal connector,
wherein the memory is encoded with a set of instructions to perform the optical assay and at least one of: an amperometric analyte assay, a potentiometric analyte assay, and a conductometric assay;
wherein the set of instructions comprises instructions to arrange the one or more electronic switches of the universal channel circuitry in an optical sensor current measurement mode to perform the optical assay, and at least one of: an amperometric measurement mode to perform the amperometric analyte assay, a potentiometric measurement mode to perform the potentiometric analyte assay, and a conductometric measurement mode to perform the conductometric assay;
wherein to perform the optical assay using the optical sensor current measurement mode, the electronic switches of the universal channel circuitry are arranged to (i) electrically connect the universal channel circuitry to a light emitter via at least one of the plurality of discrete connector contacts of the test cartridge and the multi-terminal connector, (ii) electrically connect the universal channel circuitry to a light detector via at least one of the plurality of discrete connector contacts of the test cartridge and the multi-terminal connector, (iii) drive the light emitter to generate light projected into a portion of a conduit of the test cartridge, (iv) to convert an output signal of the light detector to an analyte signal proportional to the light received from the portion of the conduit; and
wherein to perform the amperometric analyte assay using the amperometric measurement mode, the electronic switches of the universal channel circuitry are arranged to connect the universal channel circuitry to an amperometric electrode, to perform the potentiometric analyte assay using the potentiometric measurement mode, the electronic switches of the universal channel circuitry are arranged to connect the universal channel circuitry a to potentiometric electrode, and to perform the conductometric assay using the conductometric measurement mode, the electronic switches of the universal channel circuitry are arranged to connect the universal channel circuitry to a conductometric electrode.

39. The analyzer of claim 38, wherein the processor is configured to determine a qualitative, semi-quantitative, or quantitative value proportional to an amount of a target analyte in the biological sample based on the analyte signal.

40. The analyzer of claim 39, wherein the target analyte is selected from the group consisting of: human chorionic gonadotropin, glucose, lactate, creatinine, urea, prothrombin time (PT), activated partial thromboblastin time (APTT), activated clotting time (ACT), D-dimer, prostate-specific antigen (PSA), creatine kinase-MB (CKMB), brain natriuretic peptide (BNP), troponin I (TnI), cardiac troponin (cTnI), human chorionic gonadotrophin, troponin T, troponin C, myoglobin, neutrophil gelatinase-associated lipocalin (NGAL), galectin-3, prostate-specific antigen (PSA), parathyroid hormone (PTH), galectin-3, aspartate aminotransferase (AST), alanine aminotransferase (ALT), albumin, total protein, bilirubin, and alkaline phosphatase (ALP).

* * * * *